US009907812B2

(12) United States Patent
Bapat et al.

(10) Patent No.: US 9,907,812 B2
(45) Date of Patent: Mar. 6, 2018

(54) CONJUGATE-BASED ANTIFUNGAL AND ANTIBACTERIAL PRODRUGS

(75) Inventors: Abhijit S. Bapat, Delhi (IN); Gauthami Mahesh, East Delhi (IN); Rajesh S. Gokhale, New Delhi (IN); Sayali S. Shah, East Delhi (IN); Shiladitya Sengupta, Waltham, MA (US); Sudhanand Prasad, Uttar Pradesh (IN); Sumana Ghosh, New Delhi (IN); Suresh R. Chawrai, Delhi (IN); Nidhi Arora, New Delhi (IN); D. Sreedhar Reddy, Andhra Pradesh (IN); Mallika Mishra, Ghaziabad (IN); Kirti Bajaj, Haryana (IN)

(73) Assignee: VYOME BIOSCIENCES PVT. LTD., Delhi (IN)

(*) Notice: Subject to any disclaimer, the term of this patent is extended or adjusted under 35 U.S.C. 154(b) by 140 days.

(21) Appl. No.: 14/128,281

(22) PCT Filed: Jun. 22, 2012

(86) PCT No.: PCT/US2012/043717
§ 371 (c)(1),
(2), (4) Date: Aug. 21, 2014

(87) PCT Pub. No.: WO2012/177986
PCT Pub. Date: Dec. 27, 2012

(65) Prior Publication Data
US 2014/0364595 A1 Dec. 11, 2014

Related U.S. Application Data

(60) Provisional application No. 61/514,305, filed on Aug. 2, 2011.

(30) Foreign Application Priority Data

Jun. 22, 2011 (IN) .......................... 1770/DEL/2011

(51) Int. Cl.
*A61K 31/7056* (2006.01)
*A61K 47/48* (2006.01)
*A61K 31/085* (2006.01)
*A61K 31/496* (2006.01)
*A61K 8/37* (2006.01)
(Continued)

(52) U.S. Cl.
CPC .......... *A61K 31/7056* (2013.01); *A01N 37/46* (2013.01); *A61K 8/0241* (2013.01); *A61K 8/347* (2013.01); *A61K 8/361* (2013.01); *A61K 8/362* (2013.01); *A61K 8/368* (2013.01); *A61K 8/37* (2013.01); *A61K 8/375* (2013.01); *A61K 8/39* (2013.01); *A61K 8/49* (2013.01); *A61K 8/4933* (2013.01); *A61K 8/602* (2013.01); *A61K 8/8129* (2013.01); *A61K 31/085* (2013.01); *A61K 31/496* (2013.01); *A61K 47/54* (2017.08); *A61K 47/542* (2017.08); *A61K 47/552* (2017.08); *A61K 47/60* (2017.08); *A61Q 5/006* (2013.01); *A61Q 17/005* (2013.01); *A61K 2800/412* (2013.01); *A61K 2800/413* (2013.01); *A61K 2800/57* (2013.01)

(58) Field of Classification Search
CPC .............. A61K 31/7056; A61K 31/496; A61K 47/48023; A61K 47/48215; A61K 31/085
USPC .................. 536/17.4; 544/370, 366; 560/129
See application file for complete search history.

(56) References Cited

U.S. PATENT DOCUMENTS 3,784,694 A  1/1974  Model et al.
4,204,065 A  5/1980  Bodor
(Continued)

FOREIGN PATENT DOCUMENTS

AU  2009331526 B2  7/2010
EP    0178152 A2    4/1986
(Continued)

OTHER PUBLICATIONS

Bossche, H. V., Marichal, P., Gorrens, J., Geerts, H. and Janssen, P. A. J. (1988), Mode of Action Studies: Basis for the Search of New Antifungal Drugs. Annals of the New York Academy of Sciences, 544: 191-207. doi:10.1111/j.1749-6632.1988.tb40404.x.*
Guiotto et al., "PEGylation of the antimicrobial peptide nisin A: problems and perspectives" Il Farmaco, Elsevier France Editions Scientifiques et Medicales, IT 58:45-50 (2003).
Muszanska et al., "Pluroniclysozyme conjugates as anti-adhesive and antibacterial bifunctional polymers for surface coatings" Biomaterials, Elsevier Science Publishers BV., Barking, GB, 32:6333-6341 (2011).
Yang et al., "Penicillin V-conjugates PEG-PANAM star polymers" Journal of Biomaterials Science. Polymer Edition, VSP, Utrecht, NL, 14:1043-1056 (2003).
(Continued)

Primary Examiner — Yih-Horng Shiao
(74) Attorney, Agent, or Firm — Nixon Peabody LLP; David S. Resnick

(57) ABSTRACT

The invention provides conjugate-based antifungal or antibacterial prodrugs formed by coupling at least one antifungal agent or antibacterial agent with at least one linker and/or carrier. The prodrugs are of formula: (i) $(AFA)_m\text{-}X\text{-}(L)_n$; (ii) $[(AFA)_{m'}\text{-}X]_p\text{-}L$; (iii) $AFA\text{-}[X\text{-}(L)_n]_q$; or (iv) $(AFA)_{m''}\text{-}X$, wherein: AFA is an antifungal agent or an antibacterial agent; L is a carrier; X is a linker; m ranges from 1 to 10; n ranges from 2 to 10; m' is 1 to 10; p is 1 to 10; n' is 1 to 10; and q is 1 to 10, provided that q' and n are not both 1; and m" is 1 to 10. The invention also provides nanoparticles comprising the conjugate-based prodrugs. Additionally, the invention also provides non-conjugated antifungal and antibacterial agents in the form of nanoparticles.

16 Claims, 52 Drawing Sheets

(51) Int. Cl.

| | | |
|---|---|---|
| A61Q 17/00 | (2006.01) | |
| A61K 8/34 | (2006.01) | |
| A61K 8/36 | (2006.01) | |
| A61K 8/362 | (2006.01) | |
| A61K 8/368 | (2006.01) | |
| A61K 8/39 | (2006.01) | |
| A61K 8/49 | (2006.01) | |
| A61Q 5/00 | (2006.01) | |
| A61K 8/60 | (2006.01) | |
| A61K 8/81 | (2006.01) | |
| A61K 8/02 | (2006.01) | |
| A01N 37/46 | (2006.01) | |
| A61K 47/60 | (2017.01) | |
| A61K 47/54 | (2017.01) | |
| A61K 47/55 | (2017.01) | |

(56) References Cited

U.S. PATENT DOCUMENTS

| | | | |
|---|---|---|---|
| 4,313,889 A * | 2/1982 | Bodor | C07D 213/20 |
| | | | 552/544 |
| 4,431,809 A | 2/1984 | Hoehn et al. | |
| 4,587,262 A | 5/1986 | Arnould et al. | |
| 4,588,525 A | 5/1986 | Arnold et al. | |
| 5,607,685 A | 3/1997 | Cimbollek et al. | |
| 6,359,141 B2 | 3/2002 | Hudyma et al. | |
| 6,448,401 B1 | 9/2002 | Chen et al. | |
| 7,151,182 B2 | 12/2006 | Fukuda et al. | |
| 2004/0091443 A1 | 5/2004 | Niemiec et al. | |
| 2004/0209954 A1* | 10/2004 | Lukacsko | A61K 31/14 |
| | | | 514/554 |
| 2007/0292404 A1 | 12/2007 | Walsh et al. | |
| 2009/0105352 A1 | 4/2009 | Bezwada | |
| 2010/0119529 A1 | 5/2010 | Furgeson et al. | |
| 2011/0053848 A1 | 3/2011 | Cleemann et al. | |
| 2011/0123631 A1 | 5/2011 | Walzade et al. | |

FOREIGN PATENT DOCUMENTS

| | | |
|---|---|---|
| EP | 0829478 A2 | 3/1998 |
| EP | 1908770 A1 | 4/2008 |
| FR | 2839448 A | 5/2002 |
| GB | 2191483 A | 12/1987 |
| JP | 02-204413 A | 8/1990 |
| JP | 11-228548 A | 8/1999 |
| WO | 90/15628 | 12/1990 |
| WO | 94/26252 A1 | 11/1994 |
| WO | 98/03204 A1 | 1/1998 |
| WO | 99/31036 A2 | 6/1999 |
| WO | 00/64486 A2 | 11/2000 |
| WO | 02/069930 A1 | 9/2002 |
| WO | 03/070254 A1 | 8/2003 |
| WO | 2007/023398 | 3/2007 |
| WO | 2008/034019 | 3/2008 |
| WO | 2008/089185 A2 | 7/2008 |
| WO | 2008/089195 | 7/2008 |
| WO | 2009/129301 A2 | 10/2009 |
| WO | 2009/132342 A1 | 10/2009 |
| WO | 2011084846 A1 | 7/2011 |
| WO | 2011084849 A1 | 7/2011 |

OTHER PUBLICATIONS

Sloan, K., Prodrugs for Dermal Delivery, Advanced Drug Delivery Reviews, 3, 1989, pp. 67-101.
Ohwada, J., et al., Synthesis of Novel Water Soluble Benzylazolium Prodrugs of Lipophilic Azole Antifungals, Bioorganic & Medicinal Chemistry Letters, 12, 2002, pp. 2775-2780.
Ohwada, J., et al., Design, Synthesis and Antifungal Activity of a Novel Water Soluble Prodrug of Antifungal Triazole, Bioorganic & Medicinal Chemistry Letters, 13, 2003, pp. 191-196.
Kagoshima, Y., et al., Synthesis, Cleavage, and Antifungal Activity of a Number of Novel, Water-Soluble Ester Prodrugs of Antifungal Triazonle CS-758, Bioorganic & Medicinal Chemistry Letters, 19, 2009, pp. 3559-3563.
Knipe, J., et al., Nonclinical Pharmacokinetics of BMS-292655, a Water-Soluble Prodrug of the Antifungal Ravuconazole; Biopharmaceutics & Drug Disposition, 29, 2008, pp. 270-279.
Ichikawa, T., et al., Optically Active Antifungal Azoles. XII.1) Synthesis and Antifungal Activity of the Water-Soluble Prodrugs of 1-[(1R,2R)-2-(2,4-Difluorophenyl)-2-hydroxy-l-methyl-3-(1H-1,2,4-triazol-1-yl) propyl]-3[44-(1H-1-tetrazolyl)phenyl]-2-imidazolidinone, Chemical Pharmacy Bulletin, 49 (9) 2001, pp. 1102-1109.
Thorsteinsson, T., et al., Cycloserine Fatty Acid Derivatives as Prodrugs: Synthesis, Degradation and in Vitro Skin Permeability, Chemical Pharmacy Bulletin, 50, (4), 2002, pp. 554-557.
Fang, J., et al., Prodrug Strategy for Enhancing Drug Delivery via Skin; Current Drug Discovery Technologies, 3, 2006, pp. 211-224.
Jin, Y., et al., Self-assembled Drug Delivery Systems. Part 5: Self-assemblies of a Bolaamphiphilic Prodrug Containing Dual Zidovudine, International Journal of Pharmaceutics, 386, 2010, pp. 268-274.
Koch, S., et al., N-Mannich Base Derivatives of 5-Fluorocytosine: A Prodrug Approach to Improve Topical Delivery, International Journal of Pharamaceutics, 35, 1987, pp. 243-252.
Deangelis, Y., et al., Isolation and Expression of a Malassezia Globosa Lipase Gene, LIP1, Journal of Investigative Dermatology, vol. 127, 2007, pp. 2138-2146.
Dawson, Jr., T., Malassezia Globosa and Restricta: Breakthrough Understanding of the Etiology and Treatment of Dandruff and Seborrheic Dermatitis through Whole-Genome Analysis, Journal of Investigative Dermatology Symposium Proceedings, 12, 2007, pp. 15-19.
Ro, B., et al., The Role of Sebaceous Gland Activity and Scalp Microfloral Metabolism in the Etiology of Seborrheic Dermatitis and Dandruff, Journal of Investigative Dermatology Symposium Proceedings, 10, 2005, pp. 194-197.
Brunke, S., et al., MfLIP1, a Gene Encoding an Extracellular Lipase of the Lipid-dependent Fungus *Malassezia furfur*, Microbiology, 152, 2006, pp. 547-554.
Lee, B., et al., Nanoprodrugs of NSAIDs: Preparation and Characterization of Flufenamic Acid Nanoprodrugs, Journal of Drug Delivery, vol. 2011, Article ID 980720, 13 pages.
Ben-Shabat, S., et al., Vitamin D3-Based Conjugates for Topical Treatment of Psoriasis: Synthesis, Antiproliferative Activity, and Cutaneous Penetration Studies, Pharmaceutical Research, vol. 22, No. 1, Jan. 2005, pp. 50-57.
Wasdo, S., et al., Topical Delivery of a Model Phenolic Drug: Alkyloxycarbonyl Prodrugs of Acetaminophen, Pharmaceutical Research, vol. 21, No. 6, Jun. 2004, pp. 940-946.
www.suite101.com/content/malessezia-globoas-a36678?template=article_print.cfm.
Vemula, P., Self-assembled Prodrugs: An Enzymatically Triggered Drug-Delivery Platform; Biomaterials, 30, 2009, pp. 383-393.
Murray et al., "Nicotinamide: An Oral Antimicrobial Agent with Activity against Both *Mycobacterium tuberculosis* and Human Immunodeficiency Virus", Nicotinamide Therapy 36(4):453-460 (2003).
Yacoby et al., "Antibacterial nanomedicine", Nanomedicine 3(3):329-341 (2008).
Lauer et al., "Targeted delivery to the pilosebaceous unit via lipsomes", Advanced Drug Delivery Review 18:311-324 (1996).
Mishra et al., "Design, synthesis, and application of novel triclosan prodrugs as potential antimalarial and antibacterial agents", Bioorganic & Medicinal Chemistry 16:5536-5546 (2008).
Ohwada et al., "Synthesis of Novel Water Soluble Benzylazolium Prodrugs of Lipophilic Azole Antifungals", Bioorganic & Medicinal Chemistry 13:2775-2780 (2002).
Ohwada et al., "Design, Synthesis and Antifungal Activity of a Novel Water Soluble Prodrug of Antifungal Triazole", Bioorganic & Medicinal Chemistry Letters 13:191-196 (2003).
Sinkula et al., "Chemical Modification of Clindamycin: Synthesis and Evaluation of Selected Esters", Journal of Pharmaceutical Sciences 62(7):1106-1111 (1973).

(56) References Cited

OTHER PUBLICATIONS

Bharathi et al., "Identification, isolation and characterization of impurities of clindamycin palmitate hydrochloride", Journal of Pharmaceutical and Biomedical Analysis 48:1211-1218 (2008).
Contreras et al., "The Practice of Medicinal Chemistry: Identical and Non-Identical Twin Drugs", Edition 2:251-273 (2003).
Gollnick et al., "Management of Acne: A Report From a Global Alliance to Improve Outcomes in Acne", Journal of the American Academy of Dermatology 49(1):S1-S37 (2003).
Gupta et al., "Skin diseases associated with *Malassezia* species", Journal of the American Academy of Dermatology 51(5):785-798 (2004).
Wermuth C., "The Practice of Medicinal Chemistry", Edition 1:297-301 (1998).
Wermuth C., "The Practice of Medicinal Chemistry", Edition 2:275-276 (1999).
Wermuth C., "The Practice of Medicinal Chemistry: Designing Prodrugs and Bioprecursors", Edition 2:561-585 (2003).

\* cited by examiner

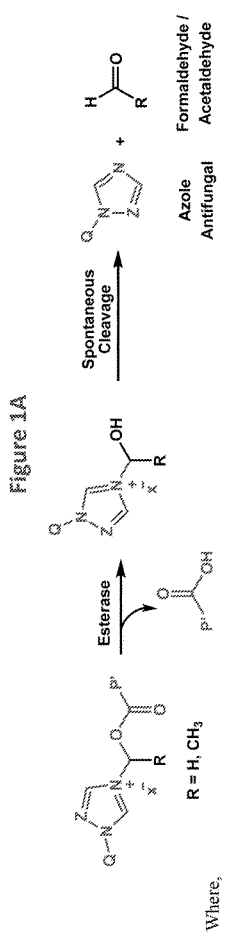
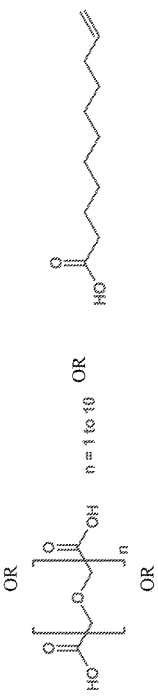
Figure 1A

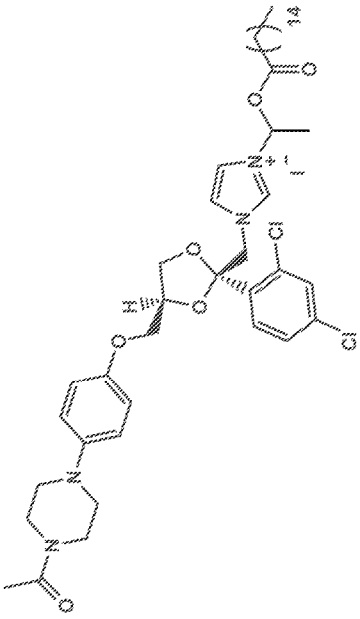
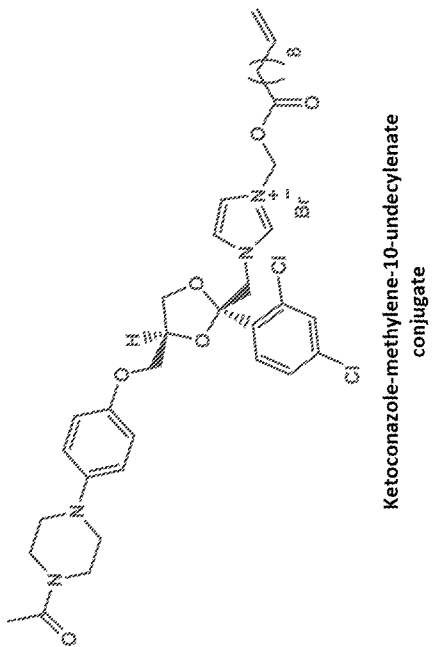
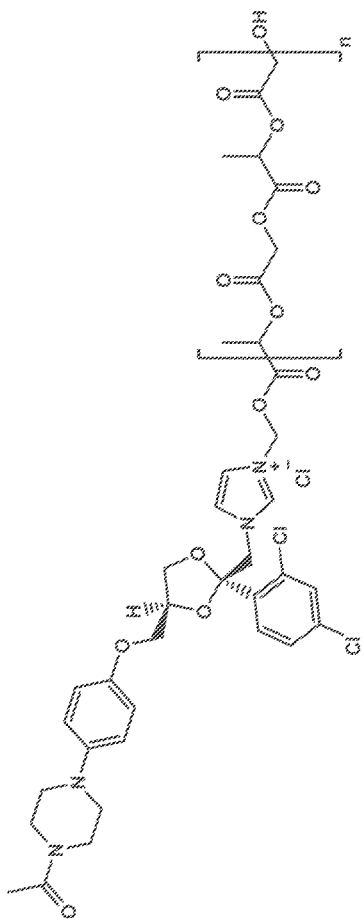
Figure 1B
Ketoconazole-1-ethylene-palmitate conjugate
Ketoconazole-methylene-10-undecylenate conjugate
Ketoconazole-methylene-PLGA conjugate

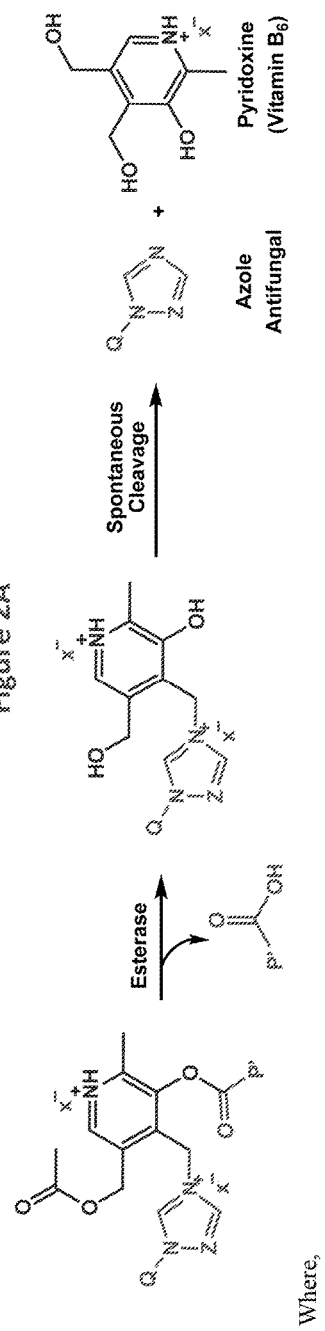

Figure 2A

Where,

Q = the reminder of an azole based antifungal agent known in the literature

Z = Nitrogen or methine; X = Cl-, Br-, I- or any pharmaceutically acceptable anion P' = non-carboxylated P P = any saturated or unsaturated fatty acid, varying from $C_8$ to $C_{26}$ carbon chain any suitable polymer known in literature with terminal -$CO_2H$ functionality. E.g., PLGA, PLA, $HO_2C$-PEG-$CO_2H$ etc $HO_2C$-$(AA)_n$-$NH_2$; where n = 1-10, AA = is L- or D-amino acid independently selected from Lys, Arg or His Ketoconazole-Pyridoxine-undecylenic acid conjugate

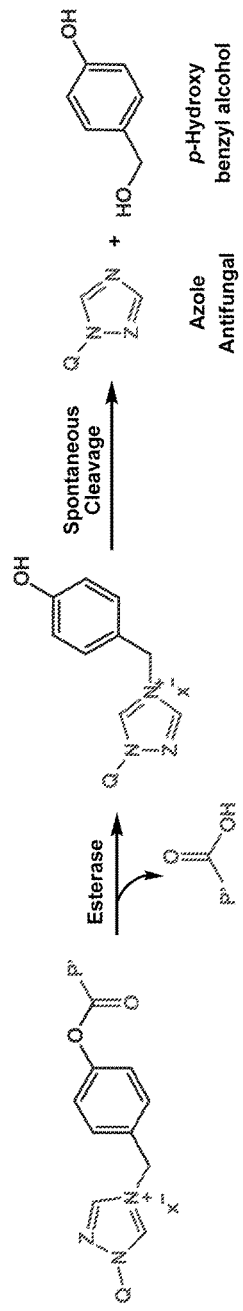

Figure 3A

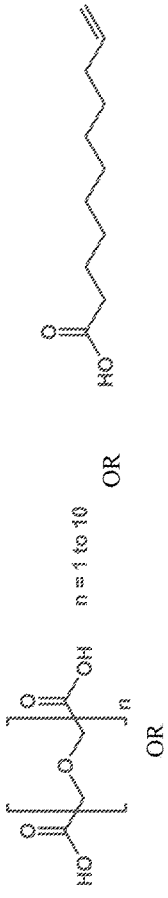

Where,

Q = the reminder of an azole based antifungal agent known in the literature

Z = Nitrogen or methine; X = Cl-, Br-, I- or any pharmaceutically acceptable anion P' = non-carboxylated P P = any saturated or unsaturated fatty acid, varying from $C_8$ to $C_{26}$ carbon chain

OR

OR any suitable polymer known in literature with terminal -$CO_2$H functionality. E.g., PLGA, PLA, $HO_2C$-PEG-$CO_2$H etc

OR $HO_2C$-(AA)$_n$-$NH_2$; where n = 1-10, AA = is L- or D-amino acid independently selected from Lys, Arg or His Ketoconazole-PLGA conjugate Ketoconazole-Linker-PLGA conjugate L = reagent(s) that would be used to incorporate L' in the conjugate Ketoconazole-methylene-oxaacid-chitosan conjugate

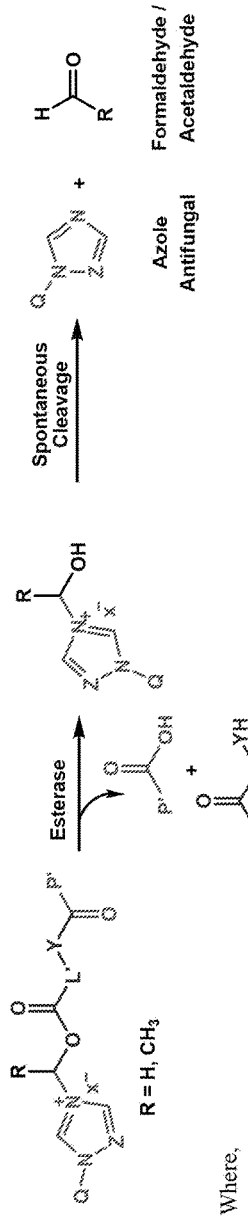

Figure 6A

Where,

Q = the reminder of an azole based antifungal agent known in the literature

Z = Nitrogen or methine; X = Cl⁻, Br⁻, I⁻ or any pharmaceutically acceptable anion Y = O or S P' = non-carboxylated P P = any saturated or unsaturated fatty acid, varying from $C_8$ to $C_{26}$ carbon chain

any suitable polymer known in literature with terminal -$CO_2H$ functionality. E.g., PLGA, PLA, $HO_2C$-PEG-$CO_2H$ etc

OR $HO_2C$-$(AA)_n$-$NH_2$; where n = 1-10, AA = is L- or D-amino acid independently selected from Lys, Arg or His

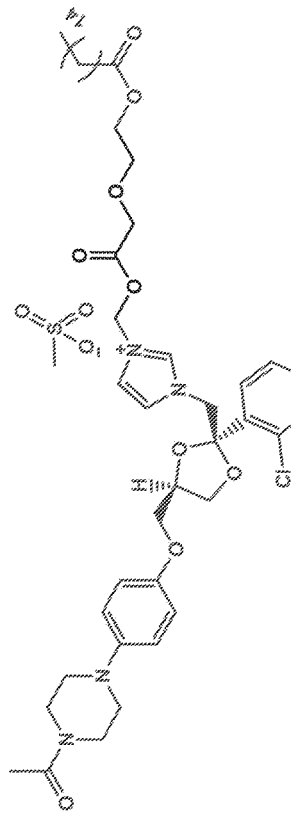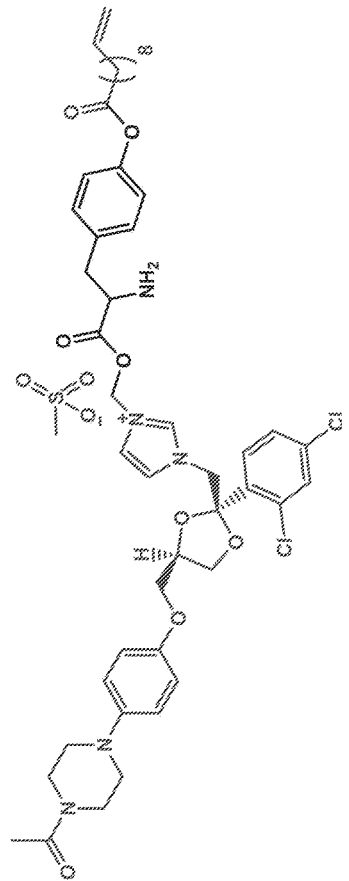
Figure 6C
Ketoconazole-methylene-linker-palmitate conjugate
Ketoconazole-methylene-linker-10-undecylenate conjugate

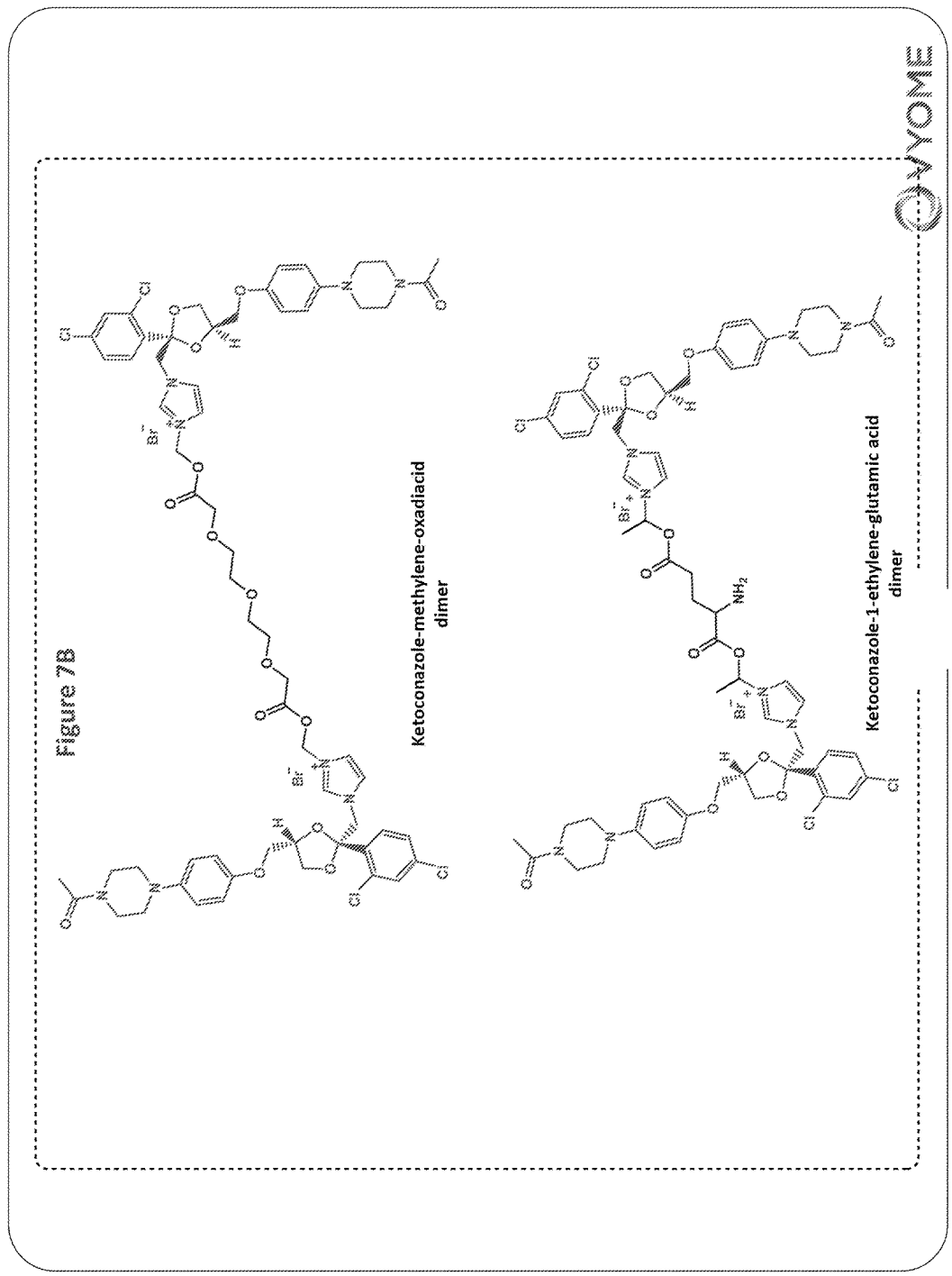

Figure 8A

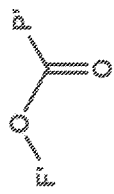

Where,

F = any antifungal agent (azole and non-azole based) known in the literature with at least one secondary or tertiary hydroxyl group F' = non-hydroxy portion of F P = any saturated or unsaturated fatty acid, varying from $C_8$ to $C_{26}$ carbon chain

OR any suitable polymer known in literature with terminal $-CO_2H$ functionality

OR

OR $HO_2C-(AA)_n-NH_2$; where n = 1-10, AA = is L- or D-amino acid independently selected from Lys, Arg or His P' = non-carboxylated P

Figure 9A

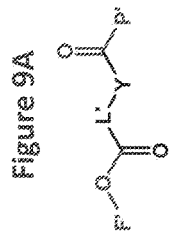

Where,

F = any antifungal agent (azole and non-azole based) known in the literature with at least one secondary or tertiary hydroxyl group F' = non-hydroxy portion of F Y = O or S P = any saturated or unsaturated fatty acid, varying from $C_8$ to $C_{26}$ carbon chain

OR any suitable polymer known in literature with terminal -$CO_2H$ functionality

OR

OR $HO_2C$-$(AA)_n$-$NH_2$; where n = 1-10, AA = is L- or D-amino acid independently selected from Lys, Arg or His P' = non-carboxylated P Figure 10A
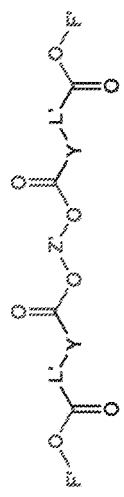
Where,
F = any antifungal agent (azole and non-azole based) known in the literature with at least one secondary or tertiary hydroxyl group
F' = non-hydroxy portion of F
Y = O or S
Z =   OR 
Where, R = H or P (connected from -CO$_2$H terminal);

and,

P = any saturated or unsaturated fatty acid, varying from $C_8$ to $C_{26}$ carbon chain

OR any suitable polymer known in literature with terminal -$CO_2H$ functionality

OR

OR $HO_2C-(AA)_n-NH_2$; where n = 1-10, AA = is L- or D-amino acid independently selected from Lys, Arg or His P' = non-carboxylated P

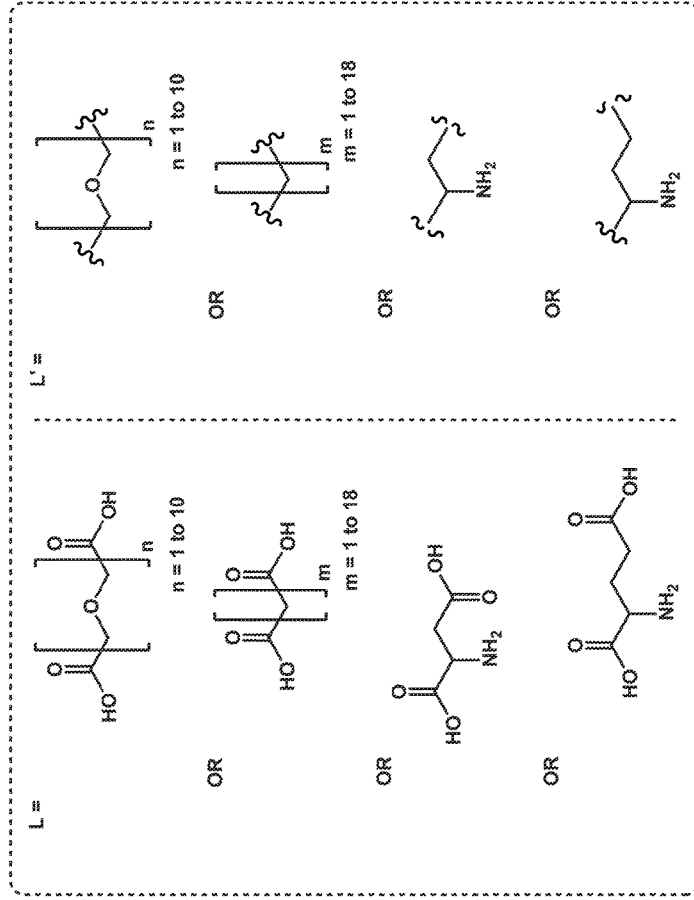

Where,

F = any antifungal agent (azole and non-azole based) known in the literature with at least one secondary or tertiary hydroxyl group F' = non-hydroxy portion of F

Figure 12A

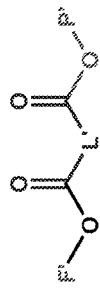

Where,

F = any antifungal agent (azole and non-azole based) known in the literature with at least one secondary or tertiary hydroxyl group F' = non-hydroxy portion of F p = any suitable polymer known in literature with terminal -OH functionality

OR

Chitosan, Pullulan, PEG

OR

L- or D-amino acid independently selected from Tyr, Ser or Thr

OR

Peptide of 2-10 residues with terminal L- or D-amino acid independently selected from Tyr, Ser or Thr as the point of attachement to the parent molecule p' = non-carboxylated p Figure 19
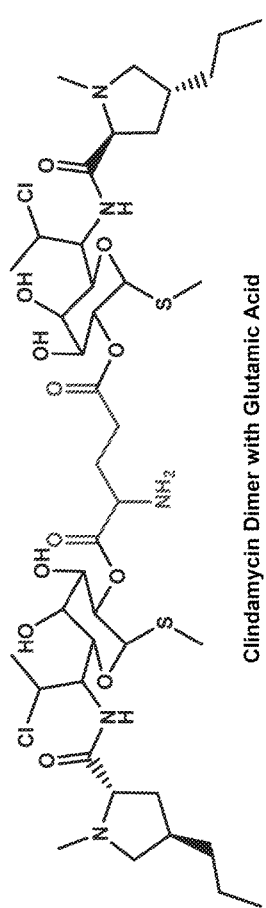
Clindamycin Dimer with Glutamic Acid
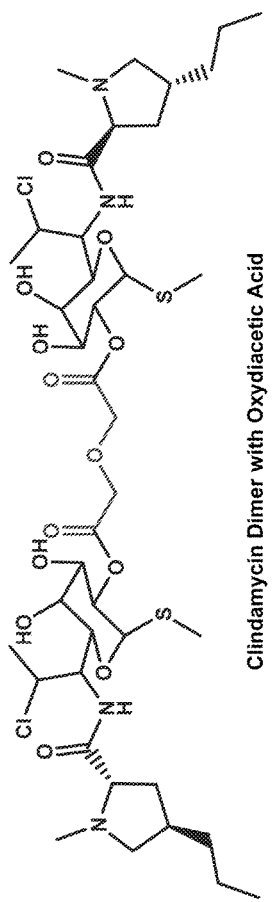
Clindamycin Dimer with Oxydiacetic Acid Figure 21
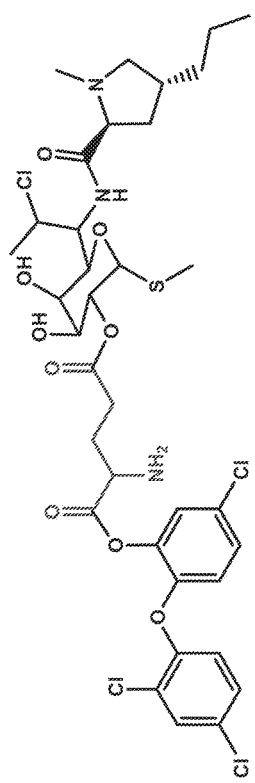
Clindamycin Triclosan with Glutamic Acid
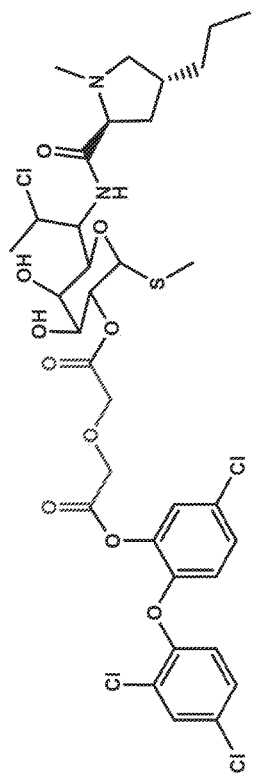
Clindamycin Triclosan with Oxydiacetic Acid

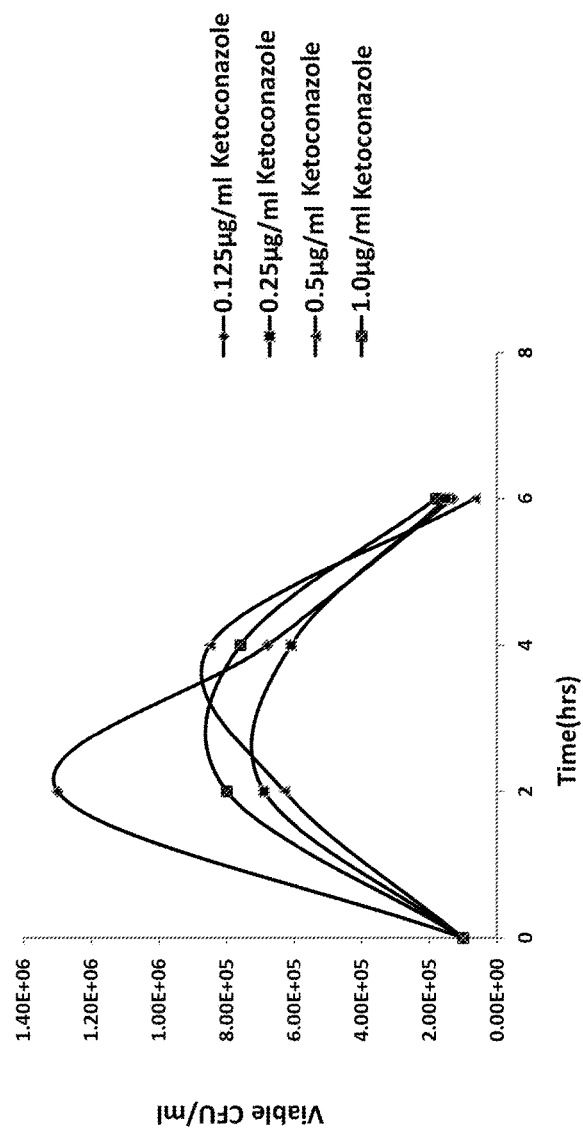

CONJUGATE-BASED ANTIFUNGAL AND ANTIBACTERIAL PRODRUGS

CROSS REFERENCE TO RELATED APPLICATIONS

This application is a 35 U.S.C. § 371 National Phase Entry Application of International Application No. PCT/US2012/043717 filed Jun. 22, 2012, which designates the U.S., and which claims benefit under one or more of 35 U.S.C. § 119(a)-119(d) of Indian Patent Application No. IN 1770/DEL/2011, filed Jun. 22, 2011 and under 35 U.S.C. § 119(e) of the U.S. Provisional Application No. 61/514,305, filed Aug. 2, 2011, the content of both applications are incorporated herein by reference in their entirety.

FIELD OF THE INVENTION

The invention relates to the field of personal care products. More specifically, the invention relates to conjugate-based antifungal and antibacterial prodrugs formed by coupling an antifungal agent or an antibacterial agent with linker(s) or carrier(s) and nanoparticles comprising the conjugate based prodrugs. The invention also relates to conjugated prodrugs in the form of nanoparticles. The invention also relates tonon-cojugated antifungal and antibacterial agents in the form of nanoparticles along one or more lipids.

BACKGROUND OF THE INVENTION

Dandruff is a chronic scalp condition that causes scaling and flaking of the skin. The causes of dandruff are not entirely known. Currently, fungi of the genus *Malassezia*, are believed to be the likely responsible agents (Dawson, Thomas L., *J. Investig. Dermatol. Symp. Proc.* (2007), 12:1519). These fungi are highly dependent on external lipids for in vitro growth (Chen T A, Hill P V 2005, *Vet Dermatol* 16:4). The lipid dependence of *Malassezia* can be explained by the apparent absence of fatty acid synthase gene (Jun Xu, et al *PNAS,* 2007, 104:18730). Further, the inability to synthesize fatty acids may be complimented by the presence of multiple secreted lipases to aid in harvesting host lipids. Consequently, these fungi metabolize triglycerides present in sebum through these lipases resulting in lipid byproducts. Penetration of the top layer of the epidermis, the stratum corneum, by some of these lipid byproducts results in an inflammatory response in susceptible persons, which disturbs homeostasis causing erratic cleavage of stratum corneum cells. The primary treatment for dandruff is the topical application of antifungal agents that reduce the level of *Malassezia* on the scalp. Typically, the antifungal agent is applied to the scalp as a component of a shampoo or other hair care composition. However, the antidandruff agents are in contact with the scalp for a short period of time, necessitating long, repeated use of the hair care composition. A long-lasting, durable dandruff treatment would represent an advance in the art.

In view of the above, a need exists for antidandruff agents that provide improved durability for long lasting effects and are easy and inexpensive to prepare.

SUMMARY OF THE INVENTION

Described herein are novel conjugate-based antifungal or antibacterial prodrugs formed by coupling at least one antifungal agent or antibacterial agent with at least one linker and/or carrier. In some embodiments the conjugate-based prodrug has the general structure:

$(AFA)_m$-X-$(L)_n$, wherein:

AFA is an antifungal agent or an antibacterial agent;
L is a carrier;
X is a linker;
m ranges from 2 to 10; and
n ranges from 2 to 10.
Typically, m is 2, 3, 4, or 5. And, n is 2, 3, 4, or 5.
In some embodiments, the conjugate-based prodrug has the general formula:

$[(AFA)_{m'}\text{-}X]_p$-L, wherein:

AFA is an antifungal agent or an antibacterial agent;
L is a carrier;
X is a linker;
m' is 1 to 10; and
p is 1 to 10.
Typically, m is 1, 2, 3, 4, or 5. And, p is 1, 2, 3, 4, or 5.
In some embodiments, m' and p are both 1.
In some embodiments, the conjugate-based prodrug has the general formula:

AFA-$[X\text{-}(L)_{n'}]_q$, wherein:

AFA is an antifungal agent or an antibacterial agent;
L is a carrier;
X is a linker;
n' is 1 to 10; and
q is 1 to 10, provided that that q' and n are not both 1.
Typically, n' is 1, 2, 3, 4, or 5. Generally q is 1, 2, 3, 4, or 5. In some embodiments, q is 1 and n' is 2.

In some embodiments, the conjugate-based antifungal prodrug has the general formula:

$(AFA)_{m''}$-X, wherein:

AFA is an antifungal agent or an antibacterial agent;
X is a linker; and
m" is 1 to 10.
Typically, m" is 1, 2, 3, 4, or 5. In some embodiments, m" is 2.

When a conjugate comprises two or more antifungal and/or antibacterial agents, such agents can be the same or different. Similarly, when a conjugate comprises two or more carrier, such agents can be the same or different Described herein also are personal care compositions comprising an effective amount of a conjugate-based antifungal or antibacterial prodrug described herein.

In another aspect, the invention provides a method for treating or preventing dandruff comprising applying a personal care composition described herein to the scalp of a subject in need thereof.

In yet another aspect, the invention provides a method for treating or preventing acne comprising applying a personal care compositions described herein to the skin of a subject in need thereof.

BRIEF DESCRIPTION OF THE DRAWINGS

FIGS. 1A-21 show exemplary conjugated prodrugs, carriers and linkers. In FIGS. 13 and 14, $RC_2OH$ can be selected from, but is not limited to, a carboxylic acid selected from a saturated or unsaturated fatty acid, comprising a $C_8$ to $C_{26}$ carbon chain; a polymer with terminal —$CO_2H$ functionality (e.g., PLGA, PLA, $HO_2C$-PEG-$CO_2H$, and the like); an antibacterial agent having a —CO₂H functionality, an alpha-hydroxy acid; a beta-hydroxy acid; azelaic acid; adapalene; a glycolic acid or derivative thereof of formula

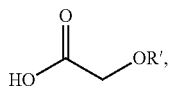

wherein R' can be an antibacterial agent with —CO₂H functionality or a carboxylic acid that can be used to modulate the 'Hydrophilic-Lypophilic-Balance' of the conjugate (e.g., PLGA); salicyclic acid or derivative thereof of formula

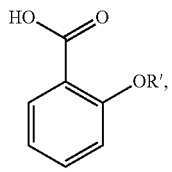

wherein R' can be an antibacterial agent with —CO₂H functionality or a carboxylic acid that can be used to modulate the 'Hydrophilic-Lypophilic-Balance' of the conjugate (e.g., PLGA); an amino acid or peptide, 10-undecenopic acid, succinic acid or derivative thereof of formula

Figure 17:
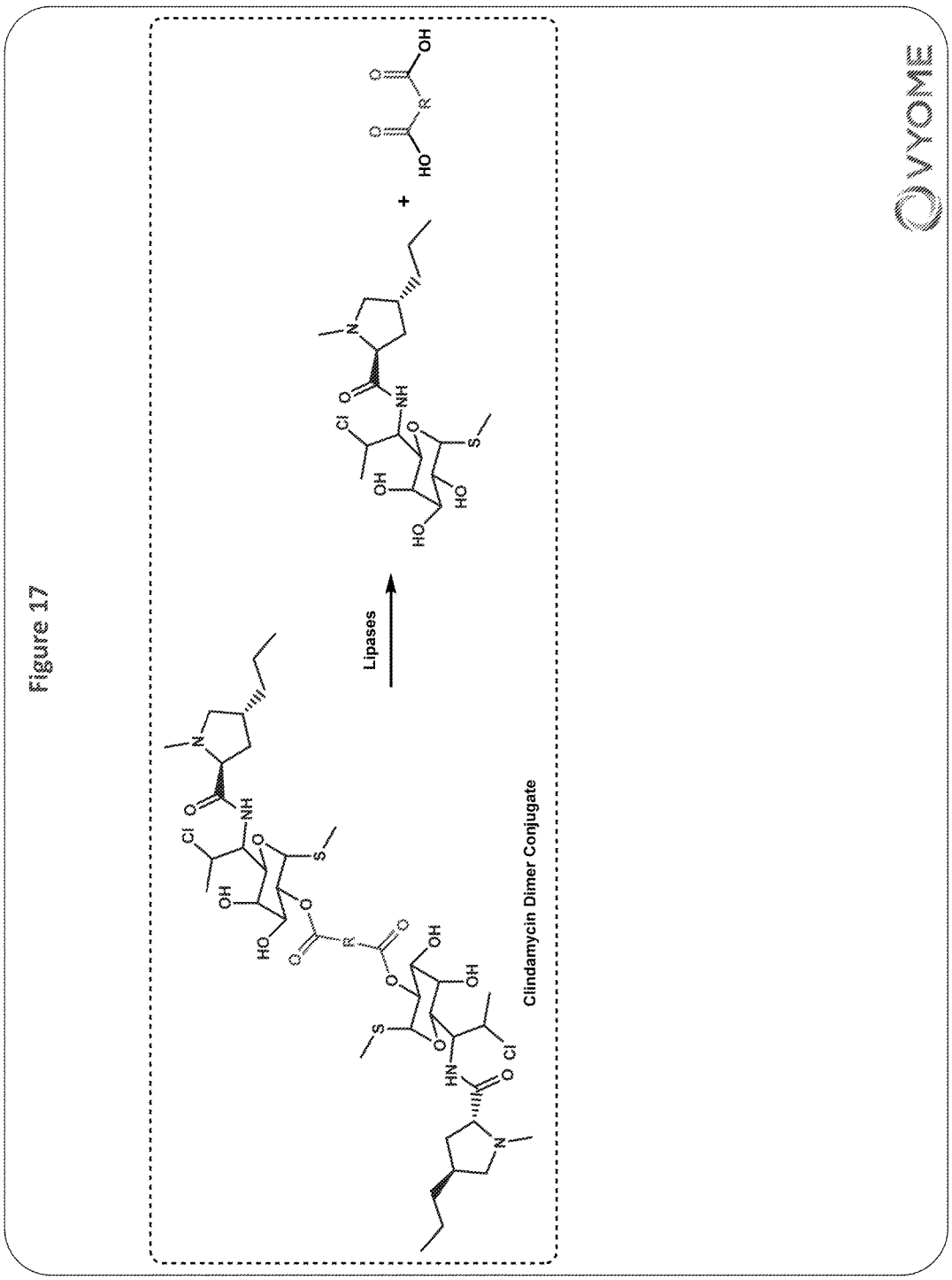
Figure 18:
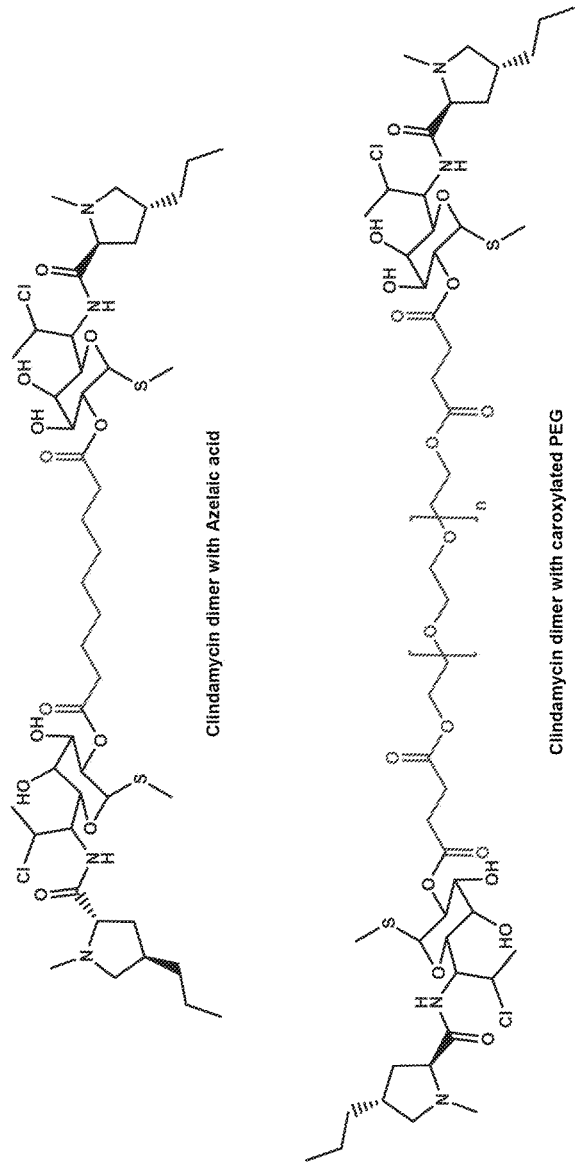
Figure 20:
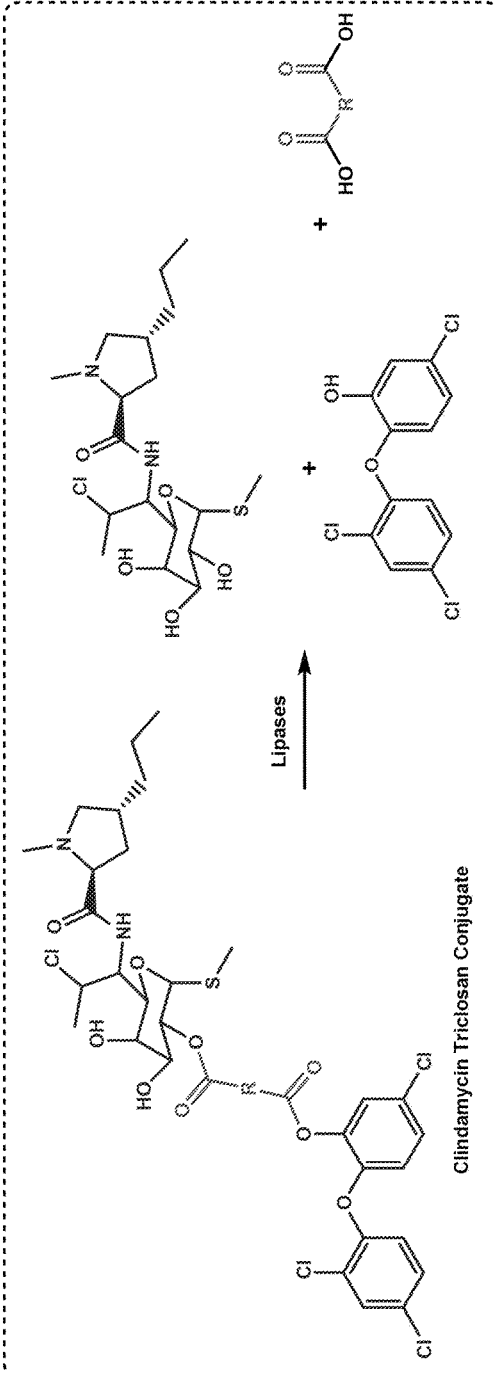

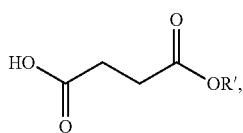

wherein R" is an antibacterial agent with —OH functionality or an alcohol that can be used to modulate the 'Hydrophilic-Lypophilic-Balance' of the conjugate (e.g., HO-PEG-OH). In FIGS. 17 and 20, R(CO₂H)₂ can be any dicarboxylic acid, for example, R(CO₂H)₂ can be selected from azelaic acid, oxadiacids of formula

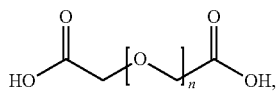

wherein n is 1 to 500, a PEG-disuccinate of formula

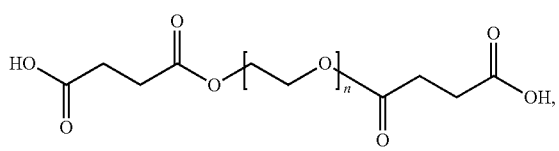

wherein n is 1 to 500; a diacid of formula

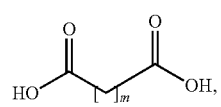

wherein m is 1 to 28; aspartic acid, glutamic acid, a polymer with —CO₂H functionality on both termini (e.g., HO₂C-PEG-CO₂H); or a natural or synthetic linker with —CO₂H functionality on both termini.

Figure 22:
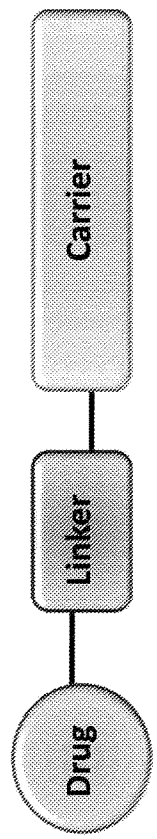

FIG. 22 is a schematic of the conjugated prodrugs of the invention.

Figure 23:
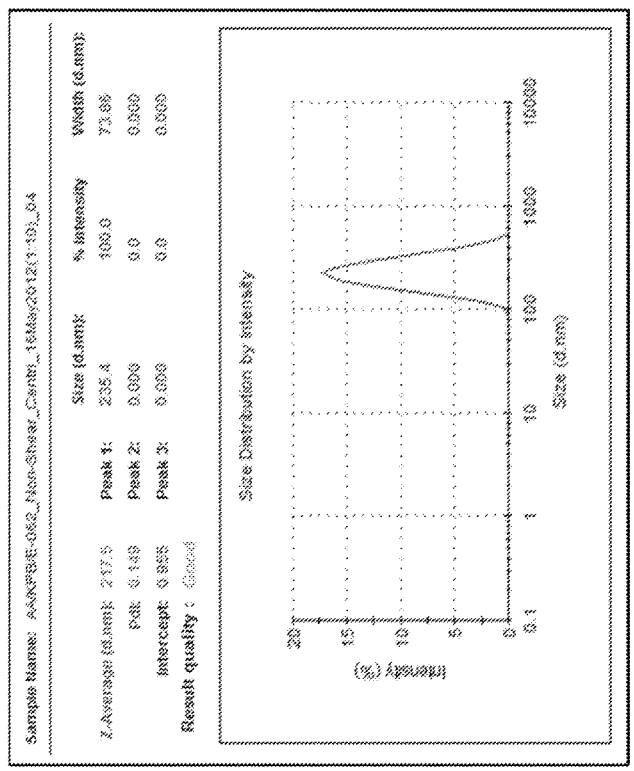
Figure 24:
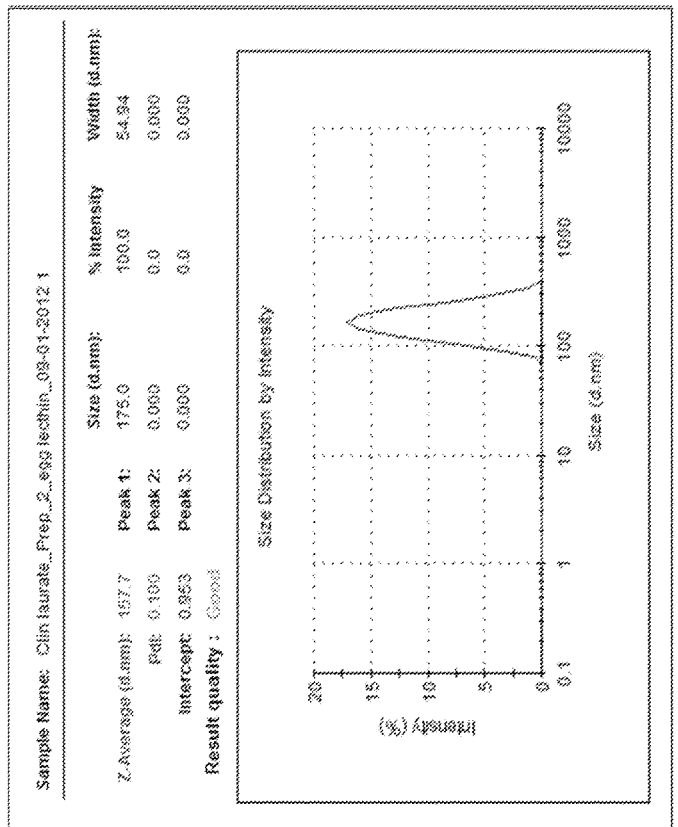

FIGS. 23 and 24 show size distribution of nanoparticles comprising clindamycin undecylene (FIG. 23) and clindamycin laurate (FIG. 24) described herein.

Figure 25:
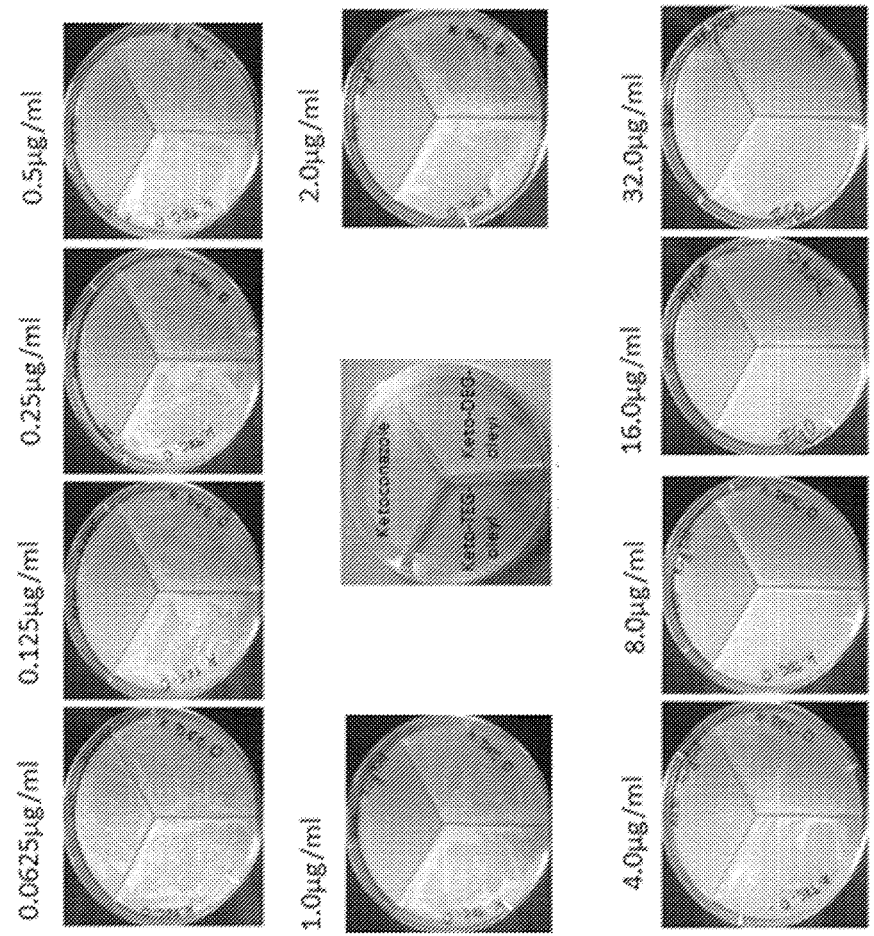
Figure 26:
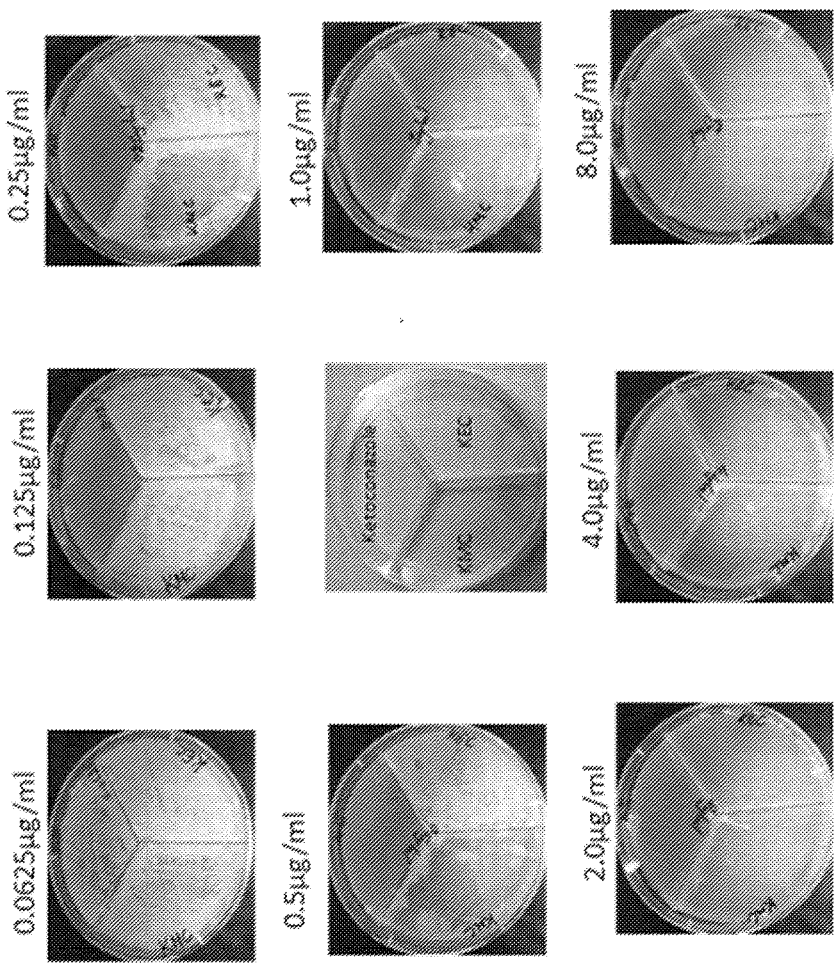
Figure 27:
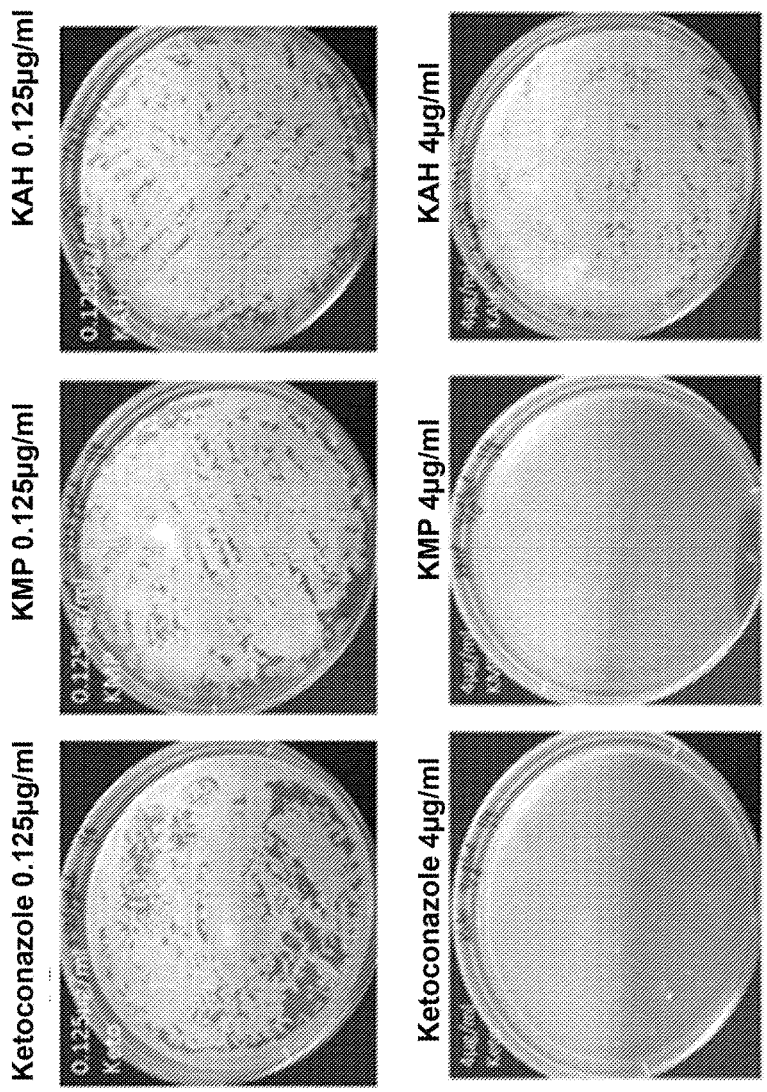

FIGS. 25-27 are photographs of MIC Agar plate assay for the TEG based conjugates (FIG. 25), methylene and ethylene based conjugates (FIG. 26), KMP and KAH conjugates (FIG. 27). Concentrations of drugs used were 0.0625 μg/ml to 16 μg/ml (FIG. 25), 0.0625 μg/ml to 8 μg/ml along with growth controls, normal saline and 1% DMSO (FIG. 26), and 0.125 μg/ml and 4 μg/ml (FIG. 27

Figure 28:
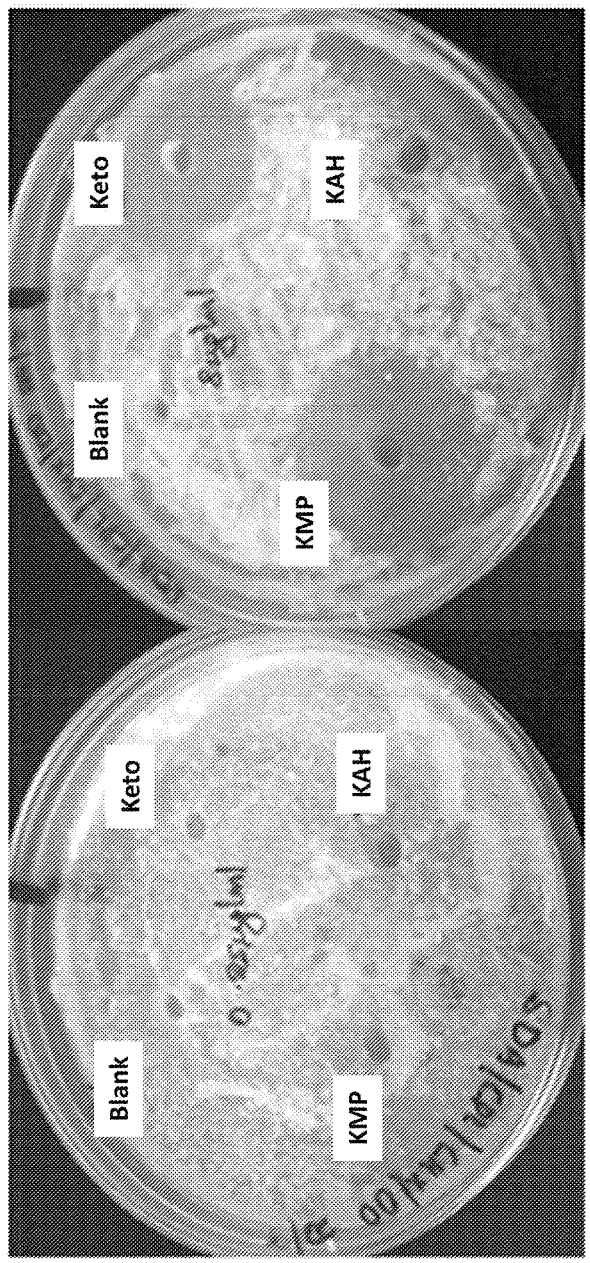

FIG. 28 is photograph of a representative Zone of Inhibition as determined by agar well diffusion method.

Figure 29:
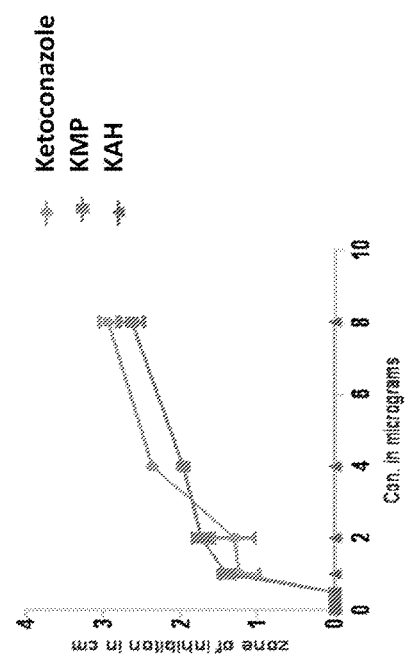

FIG. 29 is a line graph showing biological efficacy comparison between control ketoconazole, ketoconazole methylene palmitate (KMP), and negative control Keto-N-hexadecylacetamide (KAH) by Zone of inhibition. The prodrug conjugates comprised ester linkages while the negative control KAH comprised an amide linkage.

Figure 30:
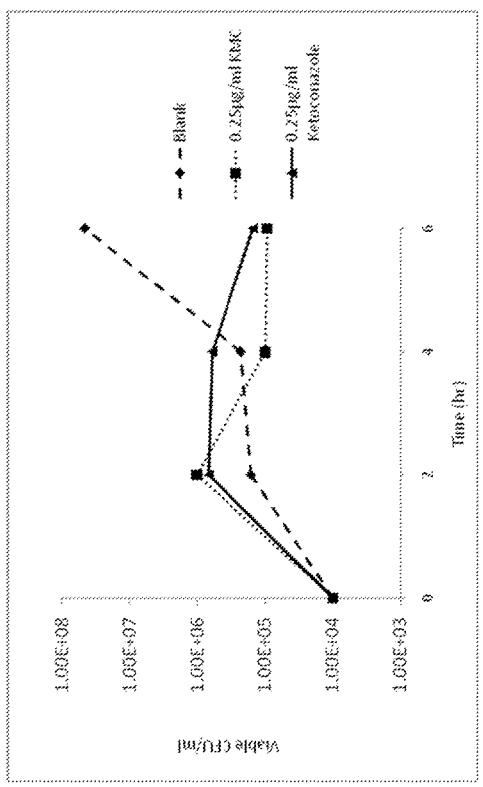

FIG. 30 is a line graph showing the Time kill assay of *M. furfur* with ketoconazole and ketoconazole-methylene-caprylate (KMC) at 0.25 μg/ml concentration.

Figure 31A:
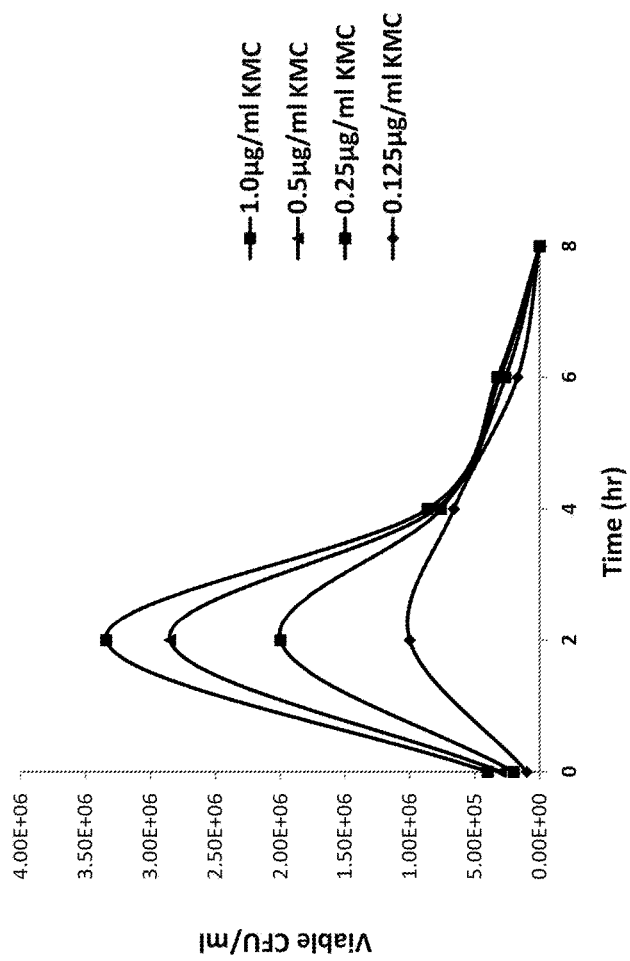

FIG. 31A is a line graph showing the Time kill assay of *M furfur* with different concentrations of prodrug KMC. Concentation of the prodrug KMC ranged from 0.125 μg/ml to 1.0 μg/ml.

FIG. 31B is a line graph showing the Time kill assay of *M furfur* with different concentrations of unconjugated ketoconazole. Concentration of the ketoconazole ranged from 0.125 μg/ml to 1.0 μg/ml.

FIGS. 32A-32C are a schematic representation of intra-follicular retention of NPs and enhanced uptake of drug by fungi or bacteria. FIG. 32A is schematic representation of cross-section of a hair follicle showing presence of microbes onto stratum corneum. It also shows NPs retained into the intra-follicular space towards epidermis, which ooze out slowly and continuously with sweat and sebum. FIG. 32B is a schematic representation showing interaction of intact NPs, released drug and released lipidic part with microbes. Presence of lipidic part (which acts a food for the lipophilic microbes) enhances uptake of the intact nanoparticles and/or released drug, eventually leading to cell death. FIG. 32C is a schematic representation of an embodiment of a nanoparticle described herein.

DETAILED DESCRIPTION OF THE INVENTION

Described herein are novel conjugate-based antifungal and/or antibacterial prodrugs formed by coupling at least one antifungal agent or antibacterial agent with at least one carrier, either directly or through a linker. Also described herein in nanoparticles comprising a non-conjugated antifungal or antibacterial agent and a lipid.

The compositions described herein (e.g., conjugate-based antifungal or antibacterial compositions, nanoparticles comprising same, and nanoparticles comprising a non-conjugated antifungal or antibacterial agent and a lipid), can be used for treatment of fungal or bacterial infections. The compositions described herein can be applied locally (e.g., topically) or administered systemically.

The compositions described herein can be used in personal care compositions, such as hair care compositions and skin care compositions. These personal care compositions can be used to treat or prevent dandruff. Compositions described herein can also be used in skin care compositions to treat or prevent acne. In some embodiments, the composition described herein can be used to treat a fugal or bacterial infection. For example, the composition described herein can be used to treat oral/vaginal candidiasis, ring worm, (tinea infections of the body, scalp, beard, jock itch, and athlete's foot), nail infections, ear infections, and the like.

In some embodiments the conjugate-based prodrug has the general structure:

AFA-X-L, wherein:

AFA is an antifungal agent or an antibacterial agent;
L is a carrier; and
X is a linker.

In some embodiments, the conjugate-based antifungal or antibacterial prodrug has the general formula:

AFA-X-AFA, wherein:

AFA is an antifungal agent or an antibacterial agent; and
X is a linker.

Without wishing to be bound by a theory, the conjugated prodrugs of the invention provide a number of advantages compared to an unconjugated antifungal and/or antibacterial agent. For example, formulation of the conjugated prodrugs into nanoparticle, allows better entrapment in skin or scalp microcracks. This in turn can allow enhanced retention time on the skin and/or scalp; allowing lower amounts of the active agent and improving bioavailability. The linker and/or the carrier can provide a synergistic effect. Additionally, the linker and/or the carrier can provide penetration enhancement. The conjugated prodrugs can also provide sustained release of the antifungal or antibacterial agent, thus providing better pharmacokinetics.

Nanoparticles

The conjugate-based prodrugs and unconjugated antifungal or antibacterial agents can be formulated into particles, e.g. nano- or microparticles. Formulation of the conjugate-based prodrugs or the unconjugated drugs into particles can be advantageous. For example, particles can be better trapped into microcracks of skin or scalp, thus providing a durable, long lasting effect. Accordingly, it can be possible to use lower concentrations of the antifungal or antibacterial agents compared to conventional antifungal and antibacterial agents.

As used herein, the term "nanoparticle" refers to particles that are on the order of $10^{-9}$ or one billionth of a meter and below $10^{-6}$ or 1 millionth of a meter in size. The term "nanoparticle" includes nanospheres; nanorods; nanoshells; and nanoprisms; and these nanoparticles may be part of a nanonetwork. The term "nanoparticles" also encompasses liposomes and lipid particles having the size of a nanoparticle. The particles may be, e.g., monodisperse or polydisperse and the variation in diameter of the particles of a given dispersion may vary, e.g., particle diameters of between about 0.1 to 100's of nm.

Without limitation, there are at least seven types of nanoparticles that can be formulated: (1) nanoparticles formed from a polymer or other material to which a conjugate-based prodrug absorbs/adsorbs or forms a coating on a nanoparticle core; (2)) nanoparticles formed from a core formed by the conjugate-based prodrug, which is coated with a polymer or other material; (3) nanoparticles formed from a polymer or other material to which a conjugate-based prodrug is covalently linked; (4) nanoparticles formed from conjugate-based prodrug and other molecules; (5) nanoparticles formed so as to comprise a generally homogeneous mixture of a conjugate-based prodrug with a constituent of the nanoparticle or other non-drug substance; (6) nanoparticles of pure drug or drug mixtures with a coating over a core of a conjugate-based prodrug; and (7) nanoparticles composed entirely of a conjugate-based prodrug. While the above is discussed with reference to conjugated prodrugs, similar types nanoparticles with unconjugated anti-bacterial or anti-fungal agents can also be prepared.

In some embodiments, the nanoparticle is of size about 1 nm to about 1000 nm, about 50 nm to about 500 nm, about 100 nm to about 250 nm, or about 200 nm to about 350 nm. In one embodiment, the nanoparticle is of about 100 nm to about 1000 nm. In another embodiment, the nanoparticle is of size about 80 nm to about 200 nm. In one embodiment, nanoparticle is of size about 50 nm to about 500 nm. In some embodiments, nanoparticle is of size about 158 nm, about 218 nm, or about 305 nm. In some embodiments, nanoparticle is of size about 337 nm, about 526 nm, about 569 nm, about 362 nm, about 476 nm, about 480 nm, about 676 nm, about 445 nm, about 434 nm, about 462 nm, about 492 nm, about 788 nm, about 463 nm, or about 65 nm Nanoparticles described herein usually have a narrow size distribution as measured by Polydispersity Index (PdI). As used herein, the term "polydispersity index" is a measure of the distribution broadness of a sample, and is typically defined as the relative variance in the correlation decay rate distribution, as is known by one skilled in the art. See B J. Fisken, "Revisiting the method of cumulants for the analysis of dynamic light-scattering data," Applied Optics, 40(24), 4087-4091 (2001) for a discussion of cumulant diameter and polydispersity. Generally, the polydispersity of the nanoparticles described herein is less than about 0.8. In some embodiments, the polydispersity of the nanoparticles is less than about 0.5, less than about 0.4, less than about 0.3, less than about 0.25, less than about 0.2, less than about 0.15, less than about 0.1, or less than about 0.05. In some embodiments, the polydispersity of the nanoparticles is about 0.072, about 0.1, about 0.149, or about 0.236, about 0.165, about 0.221, about 0.177, about 0.213, about 0.264, about 0.241, about 0.251, about 0.273, about 0.211, about 0.181, about 0.249, about 0.298, about 0.348, or about 0.282.

Without limitations, the nanoparticle can comprise other components in addition to the prodrug conjugate described herein or the unconjugated drug. For example, the nanoparticle can comprise one or more of polymers, anionic polymers, cationic polymers, amphiphilic polymers, surfactants, lipids, phospholipids, cationic lipids, amphiphilic lipids, excipients and the like. If present in nanoparticle, each of the additional component can be present in an amount ranging from about 0.01% to about 90%, e.g., from about 0.01% to about 80%, from about 0.01% to about 70%, from about 0.01% to about 60%, from about 0.01% to about 50%, from about 0.01% to about 40%, from about 0.01% to about 30%, from about 0.01% to about 25%, of the total weight of the nanoparticle. It is to be understood that amount of a component is independent from the amount of a second component in the liposome or the emulsion.

In some embodiments, the additional component is stearic acid-PEG-stearic acid or lecithin.

A surfactant that can be added to the nanoparticle can be any of anionic, cationic, ampholytic and nonionic surfactants. Examples anionic surfactants include fatty esters such as sodium stearate, potassium oleate and semicurable tallow fatty acid sodium; alkyl sulfates such as sodium dodecyl sulfate, tri(2-hydroxyethyl) ammonium dodecyl sulfate and sodium octadecyl sulfate; benzenesulfonates such as sodium nonyl benzenesulfonate, sodium dodecyl benzenesulfonate, sodium otadecyl benzenesulfonate and sodium dodecyl diphenylether disulfonate; naphthalenesulfonates such as sodium dodecyl naphthalenesulfonate and naphthalenesulfonic acid formalin condensates; sulfosuccinates such as sodium didodecyl sulfosuccinate and sodium dioctadocecyl sulfosuccinate; polyoxyethylene sulfates such as sodium polyoxyethylenedodecylether sulfate, tri(2-hydroxyethyl) ammonia polyoxyethylene dodecylether sulfate, sodium polyoxyethylene octadecylether sulfate and sodium polyoxyethylene dodecylphenylether sulfate; and phosphates such as potassium dodecyl phosphate and sodium octadecyl phosphate. Examples of cationic surfactants include alkyl amine salts such as octadecyl ammonium acetate and coconut oil amine acetate; and fourth ammonia salts such as dodecyl trimethyl ammonium chloride, octadecyl trimethyl ammonium chloride, dioctadecyl dimethyl ammonium chloride and dodecyl benzyl dimethyl ammonium chloride. Examples of ampholytic surfactants include alkyl betains such as dodecyl betain and octadodecyl betain; and amine oxides such as dodecyl dimethyl amine oxide. Examples of nonionic surfactants include polyoxyethylene alkyl ethers such as polyoxyethylene dodecyl ether, polyoxyethylene hexadecyl ether, polyoxyethylene octadecyl ether and polyoxyethylene (9-octadecenyl) ether; polyoxyethylene phenyl ethers such as polyoxyethylene octylphenyl ether and polyoxyethylene nonylphenyl ether; oxirane polymers such as polyethylene oxide and copolymer of ethylene oxide and propylene oxide; sorbitan fatty esters such as sorbitan dodecanoic ester, sorbitan hexadecanoic ester, sorbitan octadecanoic ester, sorbitan (9-octadecenoic) ester, sorbitan (9-octadecenoic) triester, polyoxyethylene sorbitan dodekanoic ester, polyoxyethylene sorbitan hexadecanoic ester, polyoxyethylene sorbitan octadecanoic ester, polyoxyethylene sorbitan octanoic triester, polyoxyethylene sorbitan (9-octadecenoic) ester and polyoxyethylene sorbitan (9-octadecenoic) triester; sorbitol fatty esters such as polyoxyethylene sorbitol (9-octadecenoic)tetraester; glycerin fatty esters such as glycerin octadecanoic ester and glycerin (9-octadecenoic) ester; polyalkylene oxide block copolymers such poloxomers (commercially available under the trademark PLURONIC® (BASF)).

Suitable commercially available amphoteric surfactants include, but are not limited to, MIRANOL® HMA sodium lauroampho acetate (38% solids) and MIRANOL® ULTRA L32 sodium lauroampho acetate available from Rhodia Novecare (Cranbury, N.J.). Suitable commercially available linear alcohol ethoxylates include, but are not limited to, SURFONIC® L12-6 six-mole ethoxylate of linear, primary 10-12 carbon number alcohol available from Huntsman Performance Products (The Woodlands, Tex.). Suitable commercially available alkyl sulfates include, but are not limited to, POLYSTEP® B-29 sodium octyl sulfate available from Stepan Company (Northfield, 111.). Suitable commercially available nonionic surfactants include, but are not limited to, oxo-alcohol polyglycol ethers such as GENAPOL® UD 070 CI 1-oxo-alcohol polyglycol ether (7 EO) available from Clariant Corporation (Cranbury, N.J.). Suitable commercially available linear alkylbenzene sulfonic acids and their salts include, but are not limited to, NAXSOFT® 98S dodecyl Benzene Sulfonic Acid and NAXSOFT® 40S Sodium dodecyl Benzene sulfonate available from Nease Corporate (Cincinnati, Ohio).

In some embodiments, surfactant is PEG-35 hydrogenated castor oil, Poloxamer 188, or sodium laureth sulphate.

Some examples of materials which can serve as excipients include: (1) sugars, such as mannitol, lactose, maltose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations.

In some embodiments, excipient is mannitol.

Without limitations, the conjugate can be formulated in any type of nanoparticle, including, but not limited to, liposomes, emulsions, microemulsions, nanoemulsions, self-microemulsifying drug delivery systems (SMEDDS), polymeric nanoparticles, solid-lipid nanoparticles, nanostructured liquid crystals, and the like.

In some embodiments, the conjugated prodrug or the unconjugated drug can be formulated in liposomes. As used herein, the term "liposome" encompasses any compartment enclosed by a lipid layer, which can be a monolayer or a bilayer. Liposomes may be characterized by membrane type and by size. Liposomes are also referred to as lipid vesicles in the art. In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae or self arranged vesicles. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane.

The liposomes that are used in the present invention are preferably formed from lipids which when combined form relatively stable vesicles. An enormous variety of lipids are known in the art which can be used to generate such liposomes. Preferred lipids include, but are not limited to, neutral and negatively charged phospholipids or sphingolipids and sterols, such as cholesterol. The selection of lipids is generally guided by consideration of, e.g., liposome size and stability in the personal care composition.

Liposomes include unilamellar vesicles which are comprised of a single lipid layer and generally have a diameter of 20 to 100 nanometers; large unilamellar vesicles (LUVS) are typically larger than 100 nm, which can also be produced by subjecting multilamellar liposomes to ultrasound. In some embodiments, liposomes have a diameter in the range of 20 nm to 400 nm.

Liposomes can further comprise one or more additional lipids and/or other components such as sterols, e.g., cholesterol. Additional lipids can be included in the liposome compositions for a variety of purposes, such as to prevent lipid oxidation, to stabilize the bilayer, to reduce aggregation during formation or to attach carriers onto the liposome surface. Any of a number of additional lipids and/or other components can be present, including amphipathic, neutral, cationic, anionic lipids, and programmable fusion lipids. Such lipids and/or components can be used alone or in combination.

Liposome compositions can be prepared by a variety of methods that are known in the art. See e.g., U.S. Pat. Nos. 4,235,871; 4,737,323; 4,897,355 and 5,171,678; published International Applications WO1996/14057 and WO1996/37194; Feigner, P. L. et al., *Proc. Natl. Acad. Sci.*, USA (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757, content of all of which is incorporated herein by reference.

In some embodiments, the conjugated prodrug or the unconjugated drug can be formulated in an emulsion. As used herein, "emulsion" is a heterogenous system of one liquid dispersed in another in the form of droplets. Emulsions are often biphasic systems comprising two immiscible liquid phases intimately mixed and dispersed with each other. Either of the phases of the emulsion can be a semisolid or a solid, as is the case of emulsion-style ointment bases and creams. The conjugate can be present as a solution in the aqueous phase, oily phase or itself as a separate phase.

In some embodiments, the compositions are formulated as nanoemulsions. The term "nanoemulsion" means an emulsion wherein the particles are of sized in the nanometer scale. Nanoemuslions also include thermodynamically stable, isotropically clear dispersions of two immiscible liquids that are stabilized by interfacial films of surface-active molecules. The application of emulsion formulations via dermatological, oral and parenteral routes and methods for their manufacture have been reviewed in the literature, for example see Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., volume 1, p. 245; and Block, in Pharmaceutical Dosage Forms, Lieberman, Rieger and Banker (Eds.), 1988, Marcel Dekker, Inc., New York, N.Y., volume 1, p. 335, content of all of which is herein incorporated by reference in its entirety.

In some embodiments, the conjugated prodrug or the unconjugated drug can be formulated in a polymeric nanoparticle. As used herein, the term "polymeric nanoparticle" refers to a carrier system in which the prodrug conjugate is retained, encapsulated or adsorbed. The term polymeric nanoparticles can be used to denote nanospheres and nanocapsules. Nanospheres are constituted of a polymer matrix in which the prodrug conjugate is retained, encapsulated or adsorbed. Nanocapsules are constituted of a polymer container enclosing a nucleus, in which the prodrug conjugate can be dissolved, retained, or dispersed in the nucleus and/or adsorbed in the polymeric wall.

Overall, the production processes for polymer nanoparticles can be classified among the methods of in situ polymerisation or methods using pre-formed polymers. Polymers commonly used in the preparation of nanoparticles are, for example poly (lactide), poly (lactideglycolide), poly (glycolide), poly (caprolactone), poly (amides), poly (anhydrides), poly (amino acids), poly (esters), poly (cyanoacrylates), poly (phosphazines), poly (phosphoesters), poly (esteramides), poly (dioxanones), poly (acetals), poly (cetals), poly (carbonates), poly (orthocarbonates), degradable poly (urethanes), chitins, chitosans, poly (hydroxybutyrates), poly (hydroxyvalerates), poly (maleic acid), poly (alkylene oxalates), poly (alkylene succinates), poly (hydroxybutyrates-co-hydroxyvalerates), and copolymers, terpolymers, oxidised cellulose, or combinations or mixtures of these materials. Some polymers that prove to be especially interesting are poly (e-caprolactone) (PCL; for example, poly (E-caprolactone) 65 Kd—Sigma Aldrich); methacryllate acid copolymers and methacryllate or acrylic esters (e.g. EUDRAGITS®); poly (alkyl methacrylate); poly (methyl methacryllate) (e.g. PMM).

Polymeric nanoparticles can be produced, for example, by the methods (i) of in situ polymerisation of monomers (latex) or dispersion of pre-formed polymers (pseudolatex or artificial latex) as described in De Jaeghere F et al. Nanoparticles. In: Mathiowitz E, ed. *The Encyclopedia of Controlled Drug Delivery*. New York, N.Y.: Wiley and Sons Inc; 1999: 641-664 and Couvreur P, et al. Controlled drug delivery with nanoparticles: *Eur J Pharm Biopharm.* 1995; 41: 2-13; (ii) method of emulsion-evaporation for pharmaceutical use first proposed by Gurny R, Peppas N A, Harrington D D, Banker G S. Development of biodegradable and injectable lattices for controlled release of potent drugs. *Drug Dev Ind Pharm.* 1981; 7: 1-25 based on U.S. Pat. No. 4,177,177, with the polymer being dissolved in a volatile organic solvent immiscible in water. The organic solution is dispersed in an aqueous phase containing emulsifier and oil/water emulsion forming facilitators; and (iii) method of the interface deposit of pre-formed polymers (nanoprecipitation) as described by Fessi et al. in U.S. Pat. No. 5,049,322. Content of all references cites in this paragraph is incorporated herein by reference.

The organic solvents that can be used for the preparation of nanoparticles are: small chain alcohols (methanol, ethanol, isopropanol, etc.), small chain ketones (acetone, methyl-ethyl-ketone, etc.), light hydrocarbons or a mixture of light hydrocarbons (hexane, petroleum ether, etc.), lightly chlorated hydrocarbons (chloroform, methylene hydrochloride, trihydrochlorideethylene, etc.), or other common light solvents such as acetonitryl, dioxane, etc. Acetone is a particularly interesting solvent.

Surfactants are commonly used to avoid the aggregation of the particles when stored. Examples of surfactants that can be used are: lecithins, synthetic, anionic (e.g. sodium lauryl sulphate), cationic (e.g. quaternary ammonium) or non-ionic (e.g. sorbitan monoesters, containing or not polyoxyethylene residues, ethers formed from fatty alcohols and polyethylene glycol, polyoxyethylene-polypropylene glycol, etc.). Particularly interesting combinations include lipophilic surfactants with low hydrophilic-lipophilic (EHL) balance values (e.g. sorbitan esters—Span 20 or Span 60) and hydrophilic surfactants with high EHL values (ethoxylated sorbitan esters-Tween 80) or, indeed, merely a single non-ionic surfactant having a high EHL (such as Tween 80).

In some embodiments, the prodrug conjugate can be formulated in a self-microemulsifying drug delivery system (SMEDDS). A self-microemulsifying drug delivery system can be described as an optically isotropic system of oil, surfactant and drug, which forms an oil in water microemulsion on gentle agitation in the presence of water. A SMEDDS for pharmaceutical application can thus be considered as a concentrate which is rapidly dispersed when introduced to the body to form an oil-in-water microemulsion.

In some embodiments, the prodrug conjugate can be formulated in a solid lipid nanoparticle. Solid lipid nanoparticles can be prepared in any manner conventional in the art, such as, for example, as described in Stuchlik, M. and Zak, S. (Lipid-Based Vehicle for Oral Delivery, *Biomed. Papers* 145 (2): 17-26, (2001)). The solid lipid nanoparticle can be prepared in a hot homogenization process by homogenization of melted lipids at elevated temperature. In this process, the solid lipid is melted and the prodrug conjugate is dissolved in the melted lipid. A pre-heated dispersion medium is then mixed with the conjugate-loaded lipid melt, and the combination is mixed with a homogenisator to form a coarse pre-emulsion. High pressure homogenization is then performed at a temperature above the lipids melting point to produce an oil/water-nanoemulsion. The nanoemulsion is cooled down to room temperature to form solid lipid nanoparticles.

Alternatively, the the solid lipid nanoparticles can be prepared in a cold homogenization process. In this process, the lipid is melted and the prodrug conjugate is dissolved in the melted lipid. The prodrug-loaded lipid is then solidified in liquid nitrogen or dry ice. The solid prodrug-lipid is ground in a powder mill to form 50-100 μm particles. The lipid particles are then dispersed in cold aqueous dispersion medium and homogenized at room temperature or below to form solid lipid nanoparticles.

Antifungal Agents

As used herein, the term "antifungal agent" is intended to mean a substance capable of inhibiting or preventing the growth, viability and/or reproduction of a fungal cell. Preferable antifungal agents are those capable of preventing or treating a fungal infection in an animal or plant. A preferable antifungal agent is a broad spectrum antifungal agent. However, an antifungal agent can also be specific to one or more particular species of fungus.

Examples of antifungal agents include, but are not limited to, azoles (e.g., Fluconazole, Isavuconazole, Itraconazole, Ketoconazole, Miconazole, Clortrimazole, Voriconazole, Posaconazole, Ravuconazole, etc.), polyenes (e.g., natamycin, lucensomycin, nystatin, amphotericin B, etc.), echinocandins (e.g., Cancidas), pradimicins (e.g., beanomicins, nikkomycins, sordarins, allylamines, etc.), Triclosan, Piroctone, fenpropimorph, terbinafine, and derivatives and analogs thereof. Additional antifungal agents include those described, for example, in Int. Pat. Pub. No. WO2001/066551, No. WO2002/090354, No. WO2000/043390, No. WO2010/032652, No. WO2003/008391, No. WO2004/018485, No. WO2005/006860, No. WO2003/086271, No. WO2002/067880; in U.S. Pat. App. Pub. No. 2008/0194661, No. 2008/0287440, No. 2005/0130940, No. 2010/0063285, No. 2008/0032994, No. 2006/0047135, No. 2008/0182885; and in U.S. Pat. No. 6,812,238; No. 4,588,525; No. 6,235,728; No. 6,265,584; No. 4,942,162; and No. 6,362,172, content of all of which is incorporated herein by reference.

In some embodiments, the antifungal agent is an azole based antifungal agent. By an azole based antifungal agent is meant an antifungal agent which comprises at least one azole in its structure. Preferred azoles include imidazoles and triazoles. Exemplary azole based antifungal agents include, but are not limited to, Fluconazole, Isavuconazole, Itraconazole, Ketoconazole, Miconazole, Clortrimazole, Voriconazole, Posaconazole, and Ravuconazole. In some embodiments, the azole based antifungal agent is linked to the linker or the carrier by a ring-nitrogen of the azole moiety.

In some embodiments, the antifungal agent comprises at least one free hydroxyl group. Exemplary antifungal agents which comprise a free hydroxyl group include, but are not limited to, Ciclopirox, Fluconazole, Voriconazole, Piroctone, Triclosan, Ravuconazole, and Isavuconazole. In some embodiments, antifungal comprising a free hydroxyl group is linked to the linker or the carrier by said free hydroxyl group.

In some embodiments, the antifungal agent is an antifungal peptide. Antifungal peptides are well known in the art (see for example, De Lucca et al., *Rev. Iberoam. Micol.* 17:116-120 (2000)). The antifungal peptide can be a naturally occurring peptide or an analog thereof, or it may be a synthetic peptide. As used herein, the term "analog" refers to a naturally occurring antifungal peptide that has been chemically modified to improve its effectiveness and/or reduce its toxic/side effects. Exemplary antifungal peptides can include, but are not limited to, syringomycins, syringostatins, syringotoxins, nikkomycins, echinocandins, pneumocadins, aculeacins, mulundocadins, cecropins, alpha-defensins, beta-defensins, novispirins, and combinations thereof. Other antifungal peptides include those described, for example, in U.S. Pat. No. 6,255,279 and U.S. Pat. App. Pub. No. 2005/0239709; No. 2005/0187151; No. 2005/0282755, and No. 2005/0245452, content all of which is incorporated herein by reference.

As used herein, the terms "fungus" or "fungi" include a variety of nucleated, spore-bearing organisms which are devoid of chlorophyll. Examples include yeasts, mildews, molds, rusts, and mushrooms. Examples of fungi include, but are not limited to *Aspergillus fumigates, Aspergillus flavus, Aspergillus nidulans, Candida albicans, Candida glabrata, Candida guilliermondii, Candida krusei, Candida lusitaniae, Candida parapsilosis, Candida tropicalis, Cryptococcus neoformans, Issatchenkia orientalis, Coccidioides, Paracoccidioides, Histoplasma, Blastomyces*, and *Neurospora crassa.*

In some embodiments, fungus is of the genus *Malassezia* (e.g., *M. furfur, M. pachydermatis, M. globosa, M. restricta, M. slooffiae, M. sympodialis, M. nana, M. yamatoensis, M. dermatis,* and *M. obtuse*).

Without wishing to be bound by a theory, the *Malassezia* species causing most skin disease in humans, including the most common cause of dandruff and seborrhoeic dermatitis, is *M. globosa* (though *M. restricta* and *M. furfur* are also involved). The skin rash of tinea versicolor (pityriasis versicolor) is also due to infection by this fungus. As the fungus requires fat to grow, it is most common in areas with many sebaceous glands: on the scalp, face, and upper part of the body. When the fungus grows too rapidly, the natural renewal of cells is disturbed and dandruff appears with itching (a similar process may also occur with other fungi or bacteria).

Accordingly, in some embodiments, the antifungal agent is an antifungal agent effective against the fungus of genus *Malassezia*. In some further embodiments of this, the antifungal agent is an antifungal agent that is effective against the fungus *M. globosa*.

In some embodiments, the antifungal agent is Itraconazole or Ketoconazole.

Antibacterial Agents

As used herein, the term "antibacterial agent" is defined as a compound having either a bactericidal or bacteriostatic effect upon bacteria contacted by the compound. As used herein, the term "bactericidal" is defined to mean having a destructive killing action upon bacteria. As used herein, the term "bacteriostatic" is defined to mean having an inhibiting action upon the growth of bacteria.

Examples of antibacterial agents include, but are not limited to, macrolides or ketolides such as erythromycin, azithromycin, clarithromycin, and telithromycin; beta-lactams including penicillin, cephalosporin, and carbapenems such as carbapenem, imipenem, and meropenem; monolactams such as penicillin G, penicillin V, methicillin, oxacillin, cloxacillin, dicloxacillin, nafcillin, ampicillin, amoxicillin, carbenicillin, ticarcillin, meziocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, and astreonam; quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; antibacterial sulfonamides and antibacterial sulphanilamides, including para-aminobenzoic acid, sulfadiazine, sulfisoxazole, sulfamethoxazole and sulfathalidine; aminoglycosides such as streptomycin, neomycin, kanamycin, paromycin, gentamicin, tobramycin, amikacin, netilmicin, spectinomycin, sisomicin, dibekalin and isepamicin; tetracyclines such as tetracycline, chlortetracycline, demeclocycline, minocycline, oxytetracycline, methacycline, doxycycline; rifamycins such as rifampicin (also called rifampin), rifapentine, rifabutin, bezoxazinorifamycin and rifaximin; lincosamides such as lincomycin and clindamycin; glycopeptides such as vancomycin and teicoplanin; streptogramins such as quinupristin and daflopristin; oxazolidinones such as linezolid; polymyxin, colistin and colymycin; trimethoprim, bacitracin, and phosphonomycin.

In some embodiments, the antibacterial agent is effective against *P. acnes*.

In some embodiments, the antibacterial agent is an anti-acne agent. As used herein, the term "antiacne agent" refers to any chemical that is effective in the treatment of acne and/or the symptoms associated therewith. Antiacne agents are well known in the art such as U.S. Pat. App. Pub. No. 2006/0008538 and U.S. Pat. No. 5,607,980, content of both of which is incorporated by reference. Examples of useful antiacne agents include, but are not limited to keratolytics, such as salicylic acid, derivatives of salicylic acid, and resorcinol; retinoids, such as retinoic acid, tretinoin, adapalene, tazarotene; sulfur-containing D- and L-amino acids and their derivatives and salts; lipoic acid; antibiotics and antimicrobials, such as benzoyl peroxide, triclosan, chlorhexidine gluconate, octopirox, tetracycline, 2,4,4'-trichloro-2'-hydroxy diphenyl ether, 3,4,4'-trichlorobanilide, nicotinamide, tea tree oil, rofecoxib, azelaic acid and its derivatives, phenoxyethanol, phenoxypropanol, phenoxisopropanol, ethyl acetate, clindamycin, erythromycin, and meclocycline; sebostats, such as flavonoids; and bile salts, such as scymnol sulfate and its derivatives, deoxycholate, and cholate; and combinations thereof. These agents are well known and commonly used in the field of personal care.

Additionally, the antiacne agent may be an antimicrobial peptide having activity against *P. acnes*. Antimicrobial peptides are ubiquitous in nature and play an important role in the innate immune system of many species (Zasloff, *Nature* 415:389-395 (2002) and Epand et al., *Biochim Biophys Acta* 1462:11-28 (1999)). The antimicrobial peptide may be a naturally occurring peptide or an analog thereof, or it may be a synthetic peptide. As used herein an "analog" refers to a naturally-occurring antimicrobial peptide that has been chemically modified to improve its effectiveness and/or reduce its toxic side effects. The antimicrobial peptide may be a peptide known to be effective against Gram positive bacteria. Non-limiting examples include lantibiotics, such as nisin, subtilin, epidermin and gallidermin; defensins; attacins, such as sarcotoxin; cecropins, such as cecropin A, bactericidin, and lepidopteran; magainins; melittins; histatins; brevinins; and combinations thereof. Additionally, antimicrobial peptides having activity against *P. acnes* have been reported, for example, in U.S. Pat. App. Pub. No. 2005/0282755; No. 2005/02455452; and No. 2005/0209157, and U.S. Pat. No. 6,255,279, content of all of which is incorporated herein by reference. Suitable examples of antimicrobial peptides having reported activity against *P. acnes* include, but are not limited to, novispirins (Hogenhaug, supra), and those described in U.S. Pat. App. Pub. No. 2007/0265431, content of which is incorporated herein by reference.

In some embodiments, the antibacterial agent is clindamycin.

Carriers

A wide variety of entities, e.g., carriers, can be coupled to an antifungal or antibacterial agent. Carriers can include naturally occurring molecules, or recombinant or synthetic molecules. Carriers can include, but are not limited to, polymers; carboxylated polymers, hydroxylated polymer, polyethylene glycols (PEG); mono- or di-carboxylated PEGs; fatty acids comprising a $C_6$-$C_{26}$ alkyl, which can be optionally substituted and/or interspersed with a heteroatom, aryl, heteroaryl, cyclyl, or heterocyclyl; alcohols comprising a $C_6$-$C_{26}$ alkyl, which can be optionally substituted and/or interspersed with a heteroatom, aryl, heteroaryl, cyclyl, or heterocyclyl; glycerol; derivatives of glycerol, amino acids; nucleic acids; antibacterial agents; antifungal agents; alpha-hydroxy acids; beta-hydroxy acids; diacids; oxadiacids; peptides; peptidomimetics; polylysine, cationic groups; spermine; spermidine; polyamine; thyrotropin; melanotropin; lectin; glycoprotein; surfactant protein A; mucin; glycosylated polyaminoacids; transferrin, aptamer; immunoglobulins (e.g., antibodies); insulin, transferrin; albumin; sugar; lipophilic molecules (e.g, steroids, bile acids, cholesterol, cholic acid, and fatty acids); vitamin A; vitamin E; vitamin K; vitamin B; folic acid; B12; riboflavin; biotin; pyridoxal; vitamin cofactors; lipopolysaccharide; hormones and hormone receptors; lectins; carbohydrates; multivalent carbohydrates; radiolabeled markers; fluorescent dyes; and any combinations thereof. A carrier can be substituted with one or more (e.g., one, two, three, four, five, six, seven, eight, nine, ten, or more) substituents. A carrier can be a therapeutic agent.

In some embodiments, the carrier comprises a free carboxylic or a free hydroxyl group. This carboxylic or hydroxyl group can be the attachment point for the linker.

In some embodiments, the carrier is a fatty acid comprising 6-25 carbons. In some embodiments, the carrier is a fatty acid selected from the group consisting of Caprylic acid, Pelargonic acid, Capric acid, Undecylic acid, Lauric acid, Tridecylic acid, Myristic acid, Pentadecylic acid, Palmitic acid, Heptadecanoic acid, Stearic acid, Nonadecylic acid, Arachidic acid, Heneicosylic acid, Behenic acid, Tricosylic acid, Lignoceric acid, Pentacosylic acid, Cerotic acid, Heptacosylic acid, Montanic acid, Myristoleic acid, Palmitoleic acid, Sapienic acid, Oleic acid, Elaidic acid, Vaccenic acid, Linoleic acid, Linoelaidic acid, α-Linolenic acid, γ-Linolenic acid, Arachidonic acid, Eicosapentaenoic acid, Erucic acid, Docosahexaenoic acid, cis-11-octadecenoic acid, cis-11-eicosenoic acid, undecylenic acid, cis-13-docosenoic acid, neoheptanoic acid, neononanoic acid, neodecanoic acid, isostearic acid, 10-undecenoic acid, and adapalene.

In some embodiments, the carrier is an alkyl alcohol, e.g., a $C_6$-$C_{25}$ alkyl alcohol. In some embodiments, the carrier is an alkyl alcohol selected from the group consisting of undecanol, lauryl alcohol, myrsityl alcohol, cetyl alcohol, oleyl alcohol.

In some embodiments, the carrier is a polyethylene glycol (PEG) or an analog or derivative thereof. A PEG carrier can be of the general formula —O—$CH_2CH_2[OCH_2CH_2]_a$R, wherein a is 1-500 and R can be H, OH, O-alkyl (e.g. O—$CH_3$), amino, alkylated amino, protected amino group. Suitable PEGs include, but are not limited to, PEG having an average molecular weight ranging from about 200 g/mole to about 30,000 g/mole.

In some embodiments, the carrier is a biocompatible polymer. As used herein, the term "biocompatible" means exhibition of essentially no cytotoxicity or immunogenicity while in contact with body fluids or tissues. As used herein, the term "polymer" refers to oligomers, co-oligomers, polymers and co-polymers, e.g., random block, multiblock, star, grafted, gradient copolymers and combination thereof.

The term "biocompatible polymer" refers to polymers which are non-toxic, chemically inert, and substantially non-immunogenic when used internally in a subject and which are substantially insoluble in blood. The biocompatible polymer can be either non-biodegradable or preferably biodegradable. Preferably, the biocompatible polymer is also noninflammatory when employed in situ.

Biodegradable polymers are disclosed in the art. Examples of suitable biodegradable polymers include, but are not limited to, linear-chain polymers such as polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, polymethyl methacrylate, chitin, chitosan, copolymers of polylactic acid and polyglycolic acid, poly(glycerol sebacate) (PGS), and copolymers, terpolymers, and copolymers including one or more of the foregoing. Other biodegradable polymers include, for example, gelatin, collagen, silk, chitosan, alginate, cellulose, poly-nucleic acids, etc.

Suitable non-biodegradable biocompatible polymers include, by way of example, cellulose acetates (including cellulose diacetate), polyethylene, polypropylene, polybutylene, polyethylene terphthalate (PET), polyvinyl chloride, polystyrene, polyamides, nylon, polycarbonates, polysulfides, polysulfones, hydrogels (e.g., acrylics), polyacrylonitrile, polyvinylacetate, cellulose acetate butyrate, nitrocellulose, copolymers of urethane/carbonate, copolymers of styrene/maleic acid, poly(ethylenimine), Pluronic (Poloxamers 407, 188), Hyaluron, heparin, agarose, Pullulan, and copolymers including one or more of the foregoing, such as ethylene/vinyl alcohol copolymers (EVOH).

In some embodiments, the biocompatible polymer is a copolymer of polylactic acid and polyglycolic acid, poly (glycerol sebacate) (PGS), poly(ethylenimine), Pluronic (Poloxamers 407, 188), Hyaluron, heparin, agarose, or Pullulan.

In some embodiments, the carrier is an amino acid or a peptide. As used herein, the term "peptide" refers to two or more amino acids joined to each other by amide bonds or modified amide bonds or modified peptide linkages. A peptide carrier can be linked by its N-terminus amino group, C-terminus carboxylic group, or a functional group (e.g, amino, hydroxyl, thiol, carboxylic) at a side chain of an amino acid in the peptide. In some embodiments, a peptide carrier is linked by its C-terminus carboxylic group. In some embodiments, peptide comprises 2-20 aminoacids. In one embodiment, the peptide comprises 2-10 aminoacids. A peptide can comprise an amino acid selected from the group consisting of alanine; argnine; asparagine; aspartic acid; cysteine; glutamic acid; glutamine; glycine; histadine; isoleucine; leucine; lysine; methionine; phenylalanine; proline; serine; threonine; tryptophan; tyrosine; valine; homocysteine; phosphoserine; phosphothreonine; phosphotyrosine; hydroxyproline; γ-carboxyglutamate; hippuric acid; octahydroindole-2-carboxylic acid; statine; 1,2,3,4,-tetrahydroisoquinoline-3-carboxylic acid; penicillamine (3-mercapto-D-valine); ornithine (Orn); citruline; alpha-methyl-alanine; para-benzoylphenylalanine; para-aminophenylalanine; p-fluorophenylalanine; phenylglycine; propargylglycine; N-methylglycins (sarcosine, Sar); and tert-butylglycine; diaminobutyric acid; 7-hydroxy-tetrahydroisoquinoline carboxylic acid; naphthylalanine; biphenylalanine; cyclohexylalanine; amino-isobutyric acid (Aib); norvaline; norleucine (Nle); tert-leucine; tetrahydroisoquinoline carboxylic acid; pipecolic acid; phenylglycine; homophenylalanine; cyclohexylglycine; dehydroleucine; 2,2-diethylglycine; 1-amino-1-cyclopentanecarboxylic acid; 1-amino-1-cyclohexanecarboxylic acid; amino-benzoic acid; amino-naphthoic acid; gamma-aminobutyric acid; difluorophenylalanine; nipecotic acid; N-α-imidazole acetic acid (IMA); thienyl-alanine; t-butylglycine; desamino-Tyr; aminovaleric acid (Ava); pyroglutaminic acid (<Glu); α-aminoisobutyric acid (αAib); γ-aminobutyric acid (γAbu); α-aminobutyric acid (αAbu); αγ-aminobutyric acid (αγAbu); 3-pyridylalanine (Pal); Iso-propyl-α-$N^\epsilon$lysine (ILys); Napthyalanine (Nal); α-napthyalanine (α-Nal); β-napthyalanine (β-Nal); Acetyl-β-napthyalanine (Ac-β-napthyalanine); α,β-napthyalanine; $N^\epsilon$-picoloyl-lysine (PicLys); 4-halo-Phenyl; 4-pyrolidylalanine; isonipecotic carboxylic acid (inip); beta-amino acids; isomers, analogs and derivatives thereof; and any combinations thereof. One of skill in the art would know that this definition includes, D- and L-amino acids, alpha- and beta-amino acids, chemically modified amino acids, naturally occurring non-proteogenic amino acids, rare amino acids, and chemically synthesized compounds that have properties known in the art to be characteristic of an amino acid.

Furthermore, as used herein, the term "amino acid" includes compounds which depart from the structure of the naturally occurring amino acids, but which have substantially the structure of an amino acid, such that they can be substituted within a peptide which retains is activity, e.g., biological activity. Thus, for example, in some embodiments amino acids can also include amino acids having side chain modifications or substitutions, and also include related organic acids, amides or the like. Without limitation, an amino acid can be a proteogenic or non-proteogenic amino acid. As used herein, the term "proteogenic" indicates that the amino acid can be incorporated into a protein in a cell through well-known metabolic pathways.

In some embodiments, a peptide carrier comprises at least one (e.g., 1, 2, 3, 4, 5, 6, 7, 8, 9, 10 or more) D amino acids. The D amino acid can be present at any position in the peptide. When more than one D amino acids are present, they can be positioned next to or not next to each other. When three or more D amino acids are present some of the D amino acids can be present next to another D amino acid while some of the D amino are not next to another D amino acid.

In some embodiments, a peptide carrier comprises at least one (e.g., 1, 2, 3, 4, 5, 6, 7, 8, 9, 10 or more) modified amide linkage to link together two amino acids in the peptide. The modified peptide linkage can be present at any position in the peptide. When more than peptide replacement linkages are present, they can be positioned next to (e.g., on both sides of a given amino acid) or not next to each other (e.g., only one side of a given amino acid is linked via a peptide replacement linkage to the next amino acid). Exemplary modified amide linkages include, but are not limited to, reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group.

In some embodiments, a peptide carrier comprises at least one (e.g., 1, 2, 3, 4, 5, 6, 7, 8, 9, 10 or more) beta-amino acids. The beta-amino acid can be present at any position in the peptide. When more than one beta-amino acids are present, they can be positioned next to or not next to each other. When three or more beta-amino acids are present some of the beta-amino acids can be present next to another beta-amino acid while some of the beta-amino are not next to another beta-amino acid. Exemplary beta-amino acids include, but are not limited to, L-(3-Homoproline hydrochloride; (±)-3-(Boc-amino)-4-(4-biphenylyl)butyric acid; (±)-3-(Fmoc-amino)-2-phenylpropionic acid; (1S,3R)-(+)-3-(Boc-amino)cyclopentanecarboxylic acid; (2R,3R)-3-(Boc-amino)-2-hydroxy-4-phenylbutyric acid; (2S,3R)-3-(Boc-amino)-2-hydroxy-4-phenylbutyric acid; (R)-2-[(Boc-amino)methyl]-3-phenylpropionic acid; (R)-3-(Boc-amino)-2-methylpropionic acid; (R)-3-(Boc-amino)-2-phenylpropionic acid; (R)-3-(Boc-amino)-4-(2-naphthyl)butyric acid; (R)-3-(Boc-amino)-5-phenylpentanoic acid; (R)-3-(Fmoc-amino)-4-(2-naphthyl)butyric acid; (R)-(−)-Pyrrolidine-3-carboxylic acid; (R)-Boc-3,4-dimethoxy-β-Phe-OH; (R)-Boc-3-(3-pyridyl)-β-Ala-OH; (R)-Boc-3-(trifluoromethyl)-β-Phe-OH; (R)-Boc-3-cyano-β-Phe-OH; (R)-Boc-3-methoxy-β-Phe-OH; (R)-Boc-3-methyl-β-Phe-OH; (R)-Boc-4-(4-pyridyl)-β-Homoala-OH; (R)-Boc-4-(trifluoromethyl)-β-Homophe-OH; (R)-Boc-4-(trifluoromethyl)-β-Phe-OH; (R)-Boc-4-bromo-β-Phe-OH; (R)-Boc-4-chloro-β-Homophe-OH; (R)-Boc-4-chloro-β-Phe-OH; (R)-Boc-4-cyano-β-Homophe-OH; (R)-Boc-4-cyano-β-Phe-OH; (R)-Boc-4-fluoro-β-Phe-OH; (R)-Boc-4-methoxy-β-Phe-OH; (R)-Boc-4-methyl-β-Phe-OH; (R)-Boc-β-Tyr-OH; (R)-Fmoc-4-(3-pyridyl)-β-Homoala-OH; (R)-Fmoc-4-fluoro-β-Homophe-OH; (S)-(+)-Pyrrolidine-3-carboxylic acid; (S)-3-(Boc-amino)-2-methylpropionic acid; (S)-3-(Boc-amino)-4-(2-naphthyl)butyric acid; (S)-3-(Boc-amino)-5-phenylpentanoic acid; (S)-3-(Fmoc-amino)-2-methylpropionic acid; (S)-3-(Fmoc-amino)-4-(2-naphthyl)butyric acid; (S)-3-(Fmoc-amino)-5-hexenoic acid; (S)-3-(Fmoc-amino)-5-phenyl-pentanoic acid; (S)-3-(Fmoc-amino)-6-phenyl-5-hexenoic acid; (S)-Boc-2-(trifluoromethyl)-β-Homophe-OH; (S)-Boc-2-(trifluoromethyl)-β-Homophe-OH; (S)-Boc-2-(trifluoromethyl)-β-Phe-OH; (S)-Boc-2-cyano-β-Homophe-OH; (S)-Boc-2-methyl-β-Phe-OH; (S)-Boc-3,4-dimethoxy-β-Phe-OH; (S)-Boc-3-(trifluoromethyl)-β-Homophe-OH; (S)-Boc-3-(trifluoromethyl)-β-Phe-OH; (S)-Boc-3-methoxy-β-Phe-OH; (S)-Boc-3-methyl-β-Phe-OH; (S)-Boc-4-(4-pyridyl)-β-Homoala-OH; (S)-Boc-4-(trifluoromethyl)-β-Phe-OH; (S)-Boc-4-bromo-β-Phe-OH; (S)-Boc-4-chloro-β-Homophe-OH; (S)-Boc-4-chloro-β-Phe-OH; (S)-Boc-4-cyano-β-Homophe-OH; (S)-Boc-4-cyano-β-Phe-OH; (S)-Boc-4-fluoro-β-Phe-OH; (S)-Boc-4-iodo-β-Homophe-OH; (S)-Boc-4-methyl-β-Homophe-OH; (S)-Boc-4-methyl-β-Phe-OH; (S)-Boc-β-Tyr-OH; (S)-Boc-γ,γ-diphenyl-β-Homoala-OH; (S)-Fmoc-2-methyl-β-Homophe-OH; (S)-Fmoc-3,4-difluoro-3-Homophe-OH; (S)-Fmoc-3-(trifluoromethyl)-β-Homophe-OH; (S)-Fmoc-3-cyano-β-Homophe-OH; (S)-Fmoc-3-methyl-β-Homophe-OH; (S)-Fmoc-γ,γ-diphenyl-β-Homoala-OH; 2-(Boc-aminomethyl)phenylacetic acid; 3-Amino-3-(3-bromophenyl)propionic acid; 3-Amino-4,4,4-trifluorobutyric acid; 3-Aminobutanoic acid; DL-3-Aminoisobutyric acid; DL-β-Aminoisobutyric acid puriss; DL-β-Homoleucine; DL-β-Homomethionine; DL-β-Homophenylalanine; DL-β-Leucine; DL-β-Phenylalanine; L-β-Homoalanine hydrochloride; L-β-Homoglutamic acid hydrochloride; L-β-Homoglutamine hydrochloride; L-β-Homohydroxyproline hydrochloride; L-β-Homoisoleucine hydrochloride; L-β-Homoleucine hydrochloride; L-β-Homolysine dihydrochloride; L-β-Homomethionine hydrochloride; L-β-Homophenylalanine allyl ester hydrochloride; L-β-Homophenylalanine hydrochloride; L-β-Homoserine; L-β-Homothreonine; L-β-Homotryptophan hydrochloride; L-β-Homotyrosine hydrochloride; L-β-Leucine hydrochloride; Boc-D-β-Leu-OH; Boc-D-β-Phe-OH; Boc-$β^3$-Homopro-OH; Boc-β-Glu(OBzl)-OH; Boc-β-Homoarg(Tos)-OH; Boc-β-Homoglu(OBzl)-OH; Boc-β-Homohyp(Bzl)-OH (dicyclohexylammonium) salt technical; Boc-β-Homolys(Z)—OH; Boc-β-Homoser(Bzl)-OH; Boc-β-Homothr(Bzl)-OH; Boc-β-Homotyr(Bzl)-OH; Boc-β-Ala-OH; Boc-β-Gln-OH; Boc-β-Homoala-OAll; Boc-β-Homoala-OH; Boc-β-Homogln-OH; Boc-β-Homoile-OH; Boc-β-Homoleu-OH; Boc-β-Homomet-OH; Boc-β-Homophe-OH; Boc-β-Homotrp-OH; Boc-β-Homotrp-OMe; Boc-β-Leu-OH; Boc-β-Lys(Z)—OH (dicyclohexylammonium) salt; Boc-β-Phe-OH; Ethyl 3-(benzylamino)propionate; Fmoc-D-β-Homophe-OH; Fmoc-L-$β^3$-homoproline; Fmoc-β-D-Phe-OH; Fmoc-β-Gln(Trt)-OH; Fmoc-β-Glu(OtBu)-OH; Fmoc-β-Homoarg(Pmc)-OH; Fmoc-β-Homogln(Trt)-OH; Fmoc-β-Homoglu(OtBu)-OH; Fmoc-β-Homohyp(tBu)-OH; Fmoc-β-Homolys(Boc)-OH; Fmoc-β-Homoser(tBu)-OH; Fmoc-β-Homothr(tBu)-OH; Fmoc-β-Homotyr(tBu)-OH; Fmoc-β-Ala-OH; Fmoc-β-Gln-OH; Fmoc-β-Homoala-OH; Fmoc-β-Homogln-OH; Fmoc-β-Homoile-OH; Fmoc-β-Homoleu-OH; Fmoc-β-Homomet-OH; Fmoc-β-Homophe-OH; Fmoc-β-Homotrp-OH; Fmoc-β-Leu-OH; Fmoc-β-Phe-OH; N-Acetyl-DL-β-phenylalanine; Z-D-β-Dab(Boc)-OH; Z-D-β-Dab(Fmoc)-OH purum; Z-DL-β-Homoalanine; Z-β-D-Homoala-OH; Z-β-Glu(OtBu)-OH technical, Q-β-Homotrp(Boc)-OH; Z-β-Ala-OH purum; Z-β-Ala-ONp purum; Z-β-Dab(Boc)-OH; Z-β-Dab(Fmoc)-OH; Z-β-Homoala-OH; β-Alanine; β-Alanine BioXtra; β-Alanine ethyl ester hydrochloride; β-Alanine methyl ester hydrochloride; β-Glutamic acid hydrochloride; cis-2-Amino-3-cyclopentene-1-carboxylic acid hydrochloride; cis-3-(Boc-amino)cyclohexanecarboxylic acid; and cis-3-(Fmoc-amino)cyclohexanecarboxylic acid.

In some embodiments, the peptide comprises amino acids selected from the group consisting of Lys, Arg, His, and any combinations thereof. In some embodiments, the amino acid linked to the linker is selected from the group consisting of Tyr, Ser, and Thr. Accordingly; a peptide can comprise a Tyr, Ser, or Thr at the N-terminus or the C-terminus for linking to rest of the conjugate. In one embodiment, peptide carrier is a Lys-His-Lys-His-Lys-His hexapeptide.

In some embodiments, the carrier is selected from the group consisting of undecylenic acid; palmitic acid; oleic acid, linoleic acid, lauric acid, Lys-His-Lys-His-Lys-His hexapeptide; L- or D-tyrosine; L- or D-serine; L- or D-threonine; a peptide of 2-10 amino acids; chitosan; pullulan; and any combinations thereof. In some embodiments, the carrier is peptide of 2-10 amino acids, wherein the N-terminus or the C-terminus amino acid is L- or D-tyrosine, L- or D-serine or L- or D-threonine; chitosan; pullulan; and any combinations thereof.

The carrier can be used in formulating conjugated prodrug into nanoparticles. For example, the carrier can be a moiety which under goes self assembly to form particles.

The carrier can be a molecule, e.g. a polymer that can be formulated in a gel, e.g., a hydrogel or an organogel. The term "hydrogel" indicates a cross-linked, water insoluble, water containing material. Hydrogels have many desirable properties for biomedical applications. For example, they can be made nontoxic and compatible with tissue, and they are usually highly permeable to water, ions and small molecules.

Gels generally comprise solid, cross-linked polymer networks capable of forming a stable system in equilibrium with an interpenetrating swelling agent. Many gel forming polymers are known in the art. Suitable gels include polymers, copolymers, and block-polymers based on monomers containing ionizable groups or polymerizable double bonds. Exemplary monomers include, but are not limited to, acrylic acid, methyl methacrylate, methyl acrylic acid, ethyl acrylate, vinyl sulfonic acid, styrene, styrene sulfonic acid (e.g., p-styrene sulfonic acid), maleic acid, butenoic acid, vinyl phosphate, vinyl phosphonate, ethylene, propylene, styrene, vinyl methyl ether, vinyl acetate, vinyl alcohol, acrylonitrile, acrylamide, N—($C_1$-$C_6$ alkyl) acrylamide (such as N-isopropylacrylamide, N-t-butylacrylamide), and the like. Gels are made by homopolymerizing or copolymerizing any of the foregoing monomers. Other suitable gel materials can include, alginate, chitosan, collagen, gelatin, hyaluronate, fibrin, agarose, and derivatives thereof. The gel can be a copolymer as described above into which has been incorporated as one co-monomeric component a conjugated prodrug.

The gel can be cross-linked to let it take a physically stable form when hydrated or dehydrated. Suitable cross-linking can be provided by incorporating about 0.5 wt. % to about 1.5% wt. % of a cross-linking agent into the gel. Cross-linking can also be provided by incorporating about 0.01 mol % to about 15 mol % of the cross-linking agent in the gel.

Suitable crosslinking agents include compounds whose molecule has a plurality of reactive groups. Such molecular crosslinking agents may be N,N'-methylene-bis acrylamide or divinylbenzene (DVB), ethylene glycol dimethacrylate, divinyl ketone, vinyl methacrylate and divinyl oxalate. Ionic crosslinkage which uses ions such as metallic ions may also be employed. Crosslinkage using electromagnetic waves such as gamma rays is also possible. Cross-linking can also be based on electrostatic interactions, hydrogen boding, hydrophobic interactions or (micro)crystal formation.

Ionically cross-linkable polymers can be anionic or cationic in nature and include, but are not limited to, carboxylic, sulfate, hydroxyl and amine functionalized polymers. The cross-linking ions used to crosslink the polymers can be anions or cations depending on whether the polymer is anionically or cationically cross-linkable. Appropriate cross-linking ions include, but are not limited to, cations selected from the group consisting of calcium, magnesium, barium, strontium, boron, beryllium, aluminum, iron, copper, cobalt, lead and silver ions. Anions can be selected from, but are not limited to, the group consisting of phosphate, citrate, borate, succinate, maleate, adipate and oxalate ions. More broadly, the anions are derived from polybasic organic or inorganic acids. Preferred cross-linking cations are calcium, iron, and barium ions. The most preferred cross-linking cations are calcium and barium ions. The most preferred cross-linking anion is phosphate. Cross-linking can be carried out by contacting the polymers with a nebulized droplet containing dissolved ions. For example, the gelation of collagen or alginate occurs in the presence of ionic cross-linker or divalent cations such as $Ca^{2+}$, $Ba^{2+}$ and $Sr^{2+}$.

Linkers

As used herein, the term "linker" refers to an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

The linker can be attached to a ring nitrogen of an azole moiety of the antifungal or antibacterial agent. Alternatively, the linker can be attached to a hydroxyl or carboxylic group of the antifungal or antibacterial agent. The linker can also be attached to heteroatom of the antifungal or antibacterial agent, e.g., O, S, or N.

In some embodiments, the linker comprises at least one cleavable linking group, i.e., the linker is a cleavable linker. Without wishing to be bound by a theory, using cleavable linkers can provide sustained release of the antifungal or antibacterial agent from the conjugate. This can provide better pharmacokinetics. For example, using lipase cleavable linkers, no/insignificant cleavage would occur in the absence of a fungus. Therefore no/insignificant amount of the drug would be released thus lowering any toxicity of the drug.

A cleavable linking group is one which is sufficiently stable but which is cleaved under specific conditions or with specific enzymes. In a preferred embodiment, the cleavable linking group is cleaved at least 10 times or more, preferably at least 100 times faster under the specified conditions or under a first reference condition (which can, e.g., be selected to mimic or represent intracellular conditions) than a reference condition.

A linker can include a cleavable linking group that is cleavable by a particular enzyme. The type of cleavable linking group incorporated into a linker can depend on the target application. For example, *M. globosa* uses eight different types of lipases, along with three phospholipases, to break down the oils on the scalp. Accordingly, linker comprising ester linkages will be cleaved more efficiently in the presence of *M. globosa* relative to when *M. globosa* is absent.

Cleavable linking groups can be susceptible to cleavage agents, e.g., pH, redox potential or the presence of degradative molecules. Generally, cleavage agents are more prevalent or found at higher levels or activities inside cells than in serum or blood. Examples of such degradative agents include: redox agents, which are selected for particular substrates or which have no substrate specificity, including, e.g., oxidative or reductive enzymes or reductive agents such as mercaptans, present in cells that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

In some embodiments, cleavable linking group is cleaved at least 1.25, 1.5, 1.75, 2, 3, 4, 5, 10, 25, 50, or 100 times faster in the presence of *Malassezia* species as compared to in the absence of *Malassezia* species. In some embodiments, the cleavable linking group is cleaved by less than 90%, 80%, 70%, 60%, 50%, 40%, 30%, 20%, 10%, 5%, or 1% in the absence of *Malassezia* species as compared to in the presence of *Malassezia* species.

In some embodiments, the linker is a Generally Recognized As Safe (GRAS) excipient.

Figure 5A:
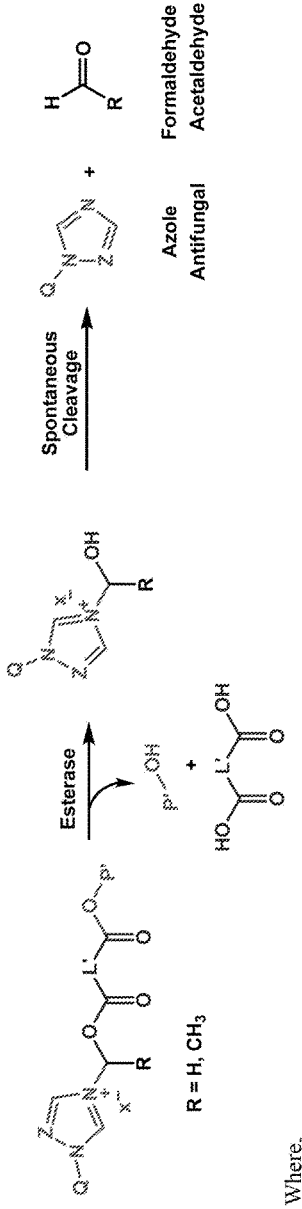
Figure 5B:
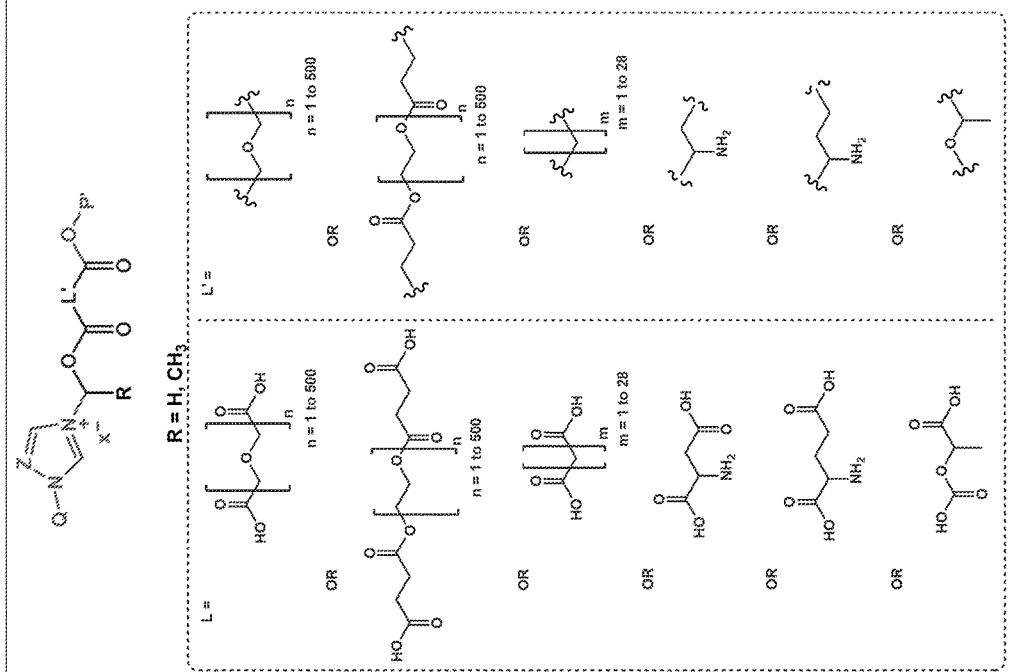
Figure 5C:
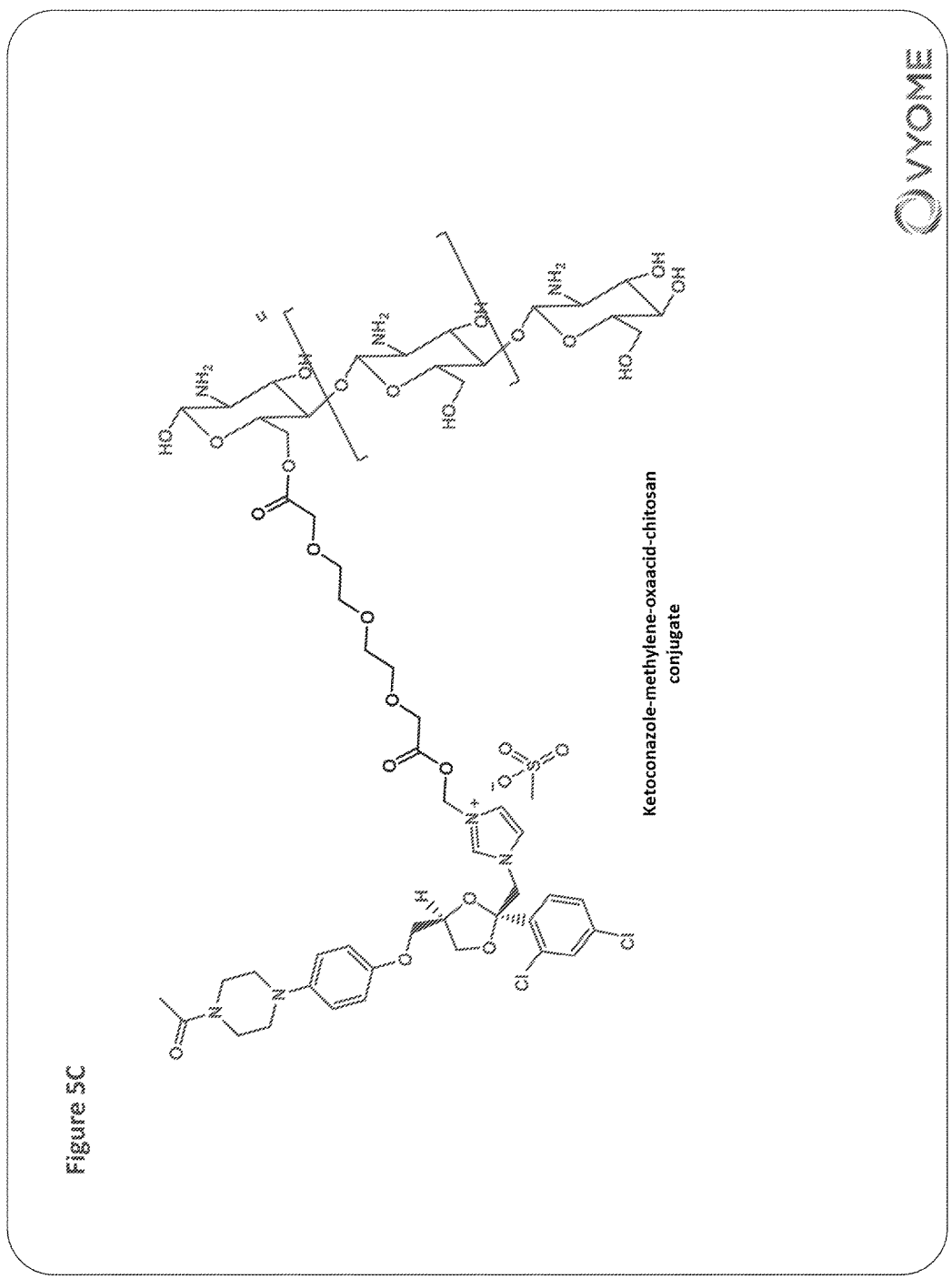
Figure 6B:
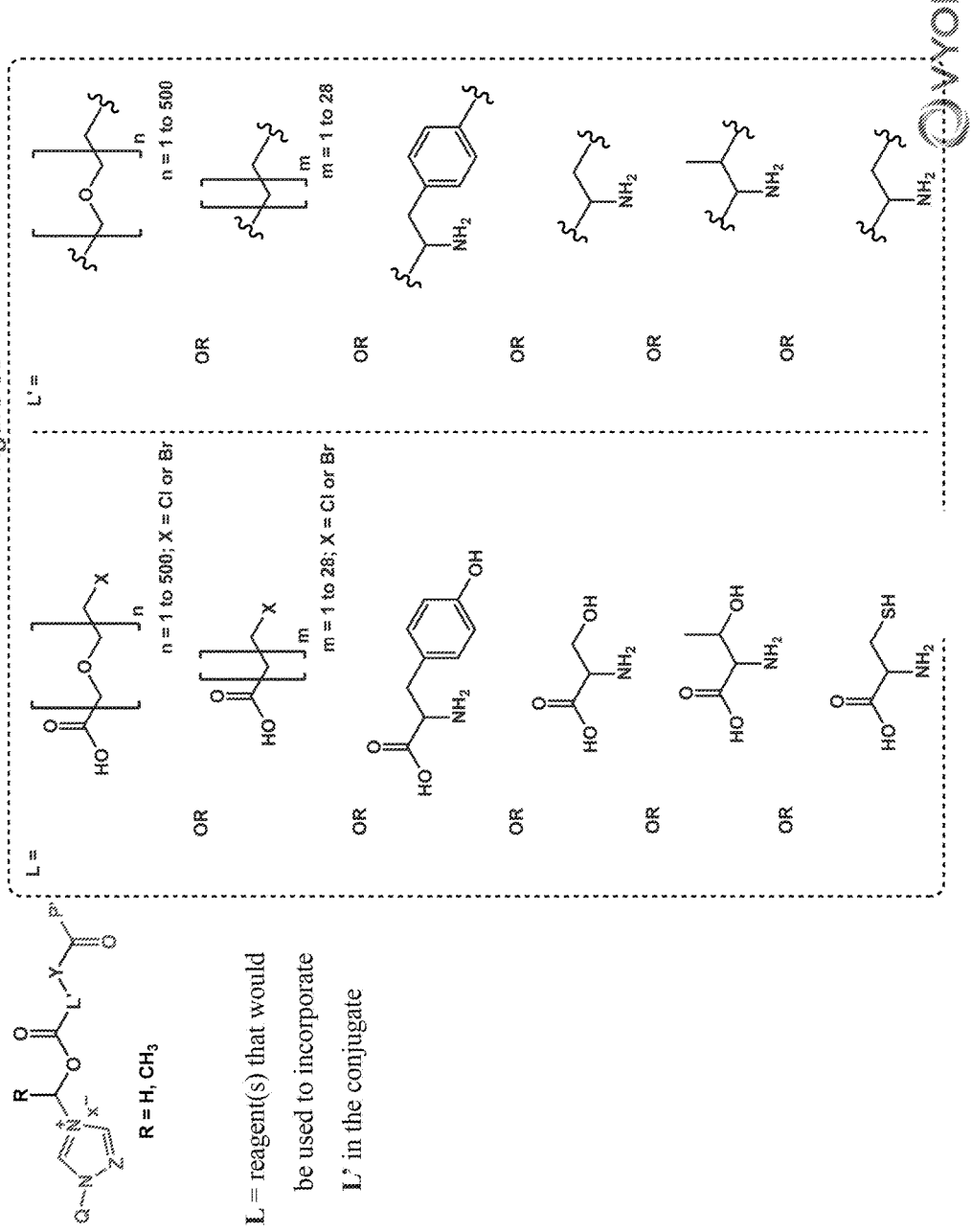
Figure 6D:
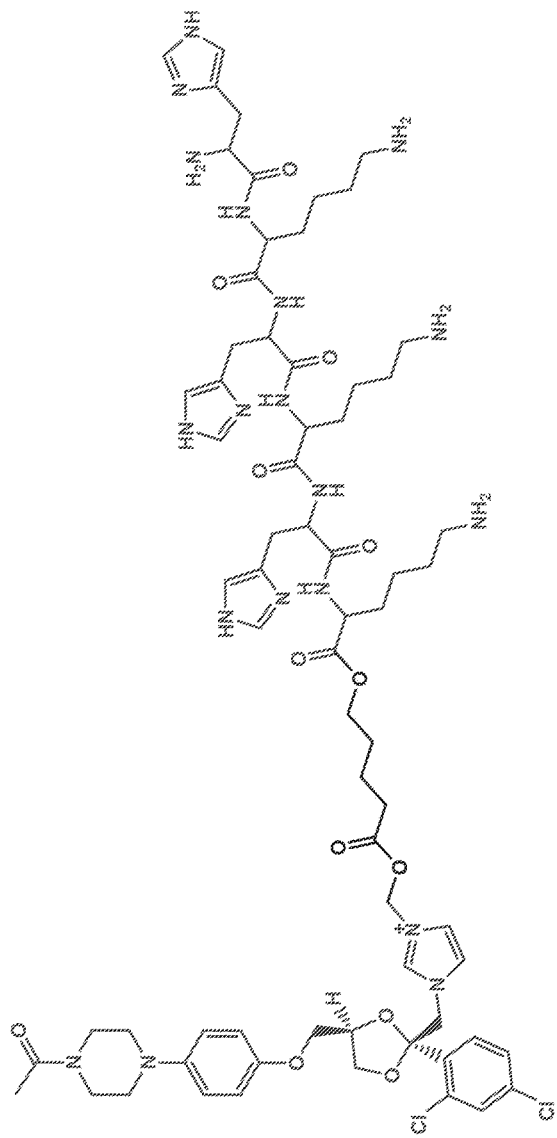
Figure 7A:
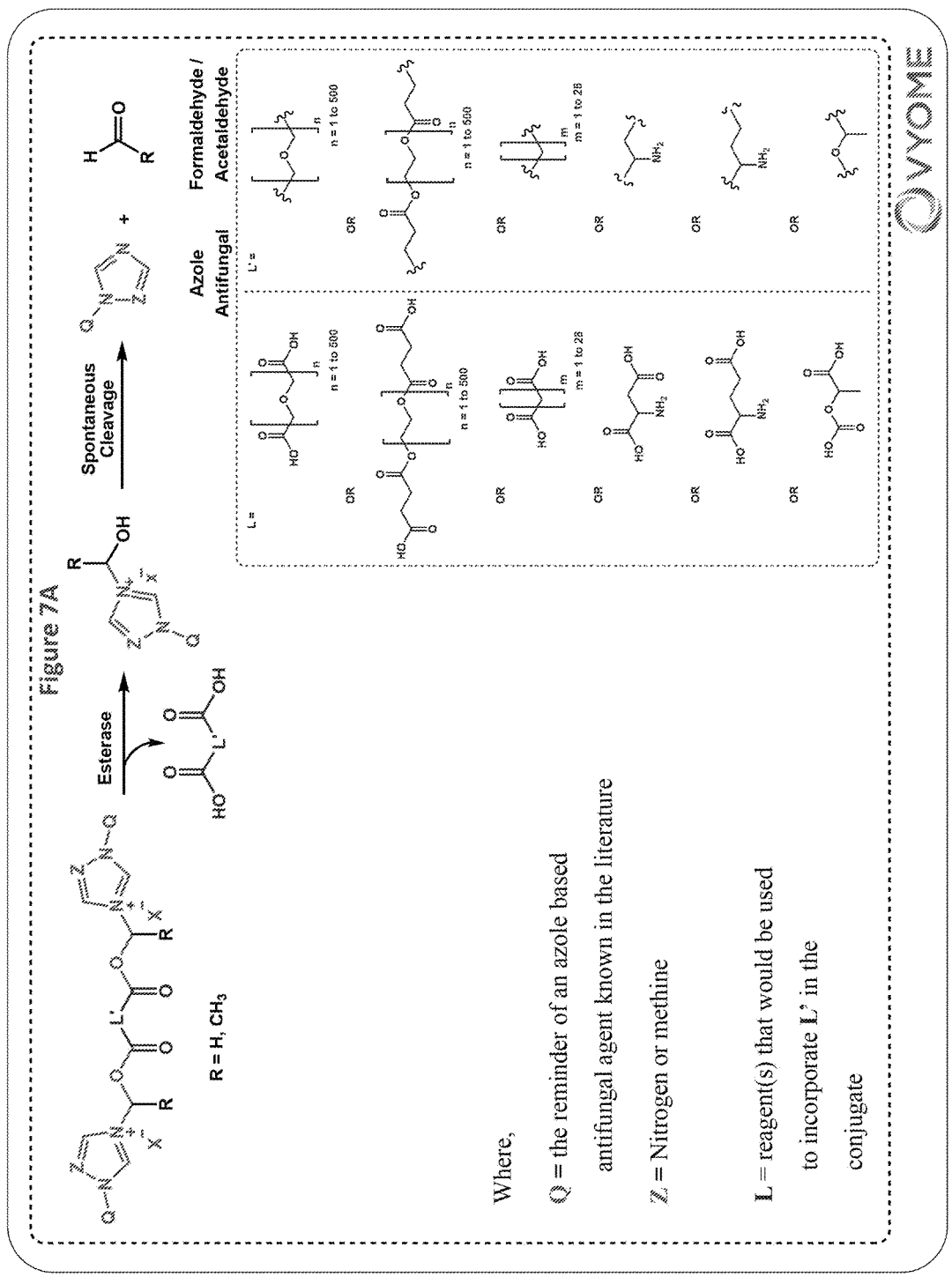
Figure 8B:
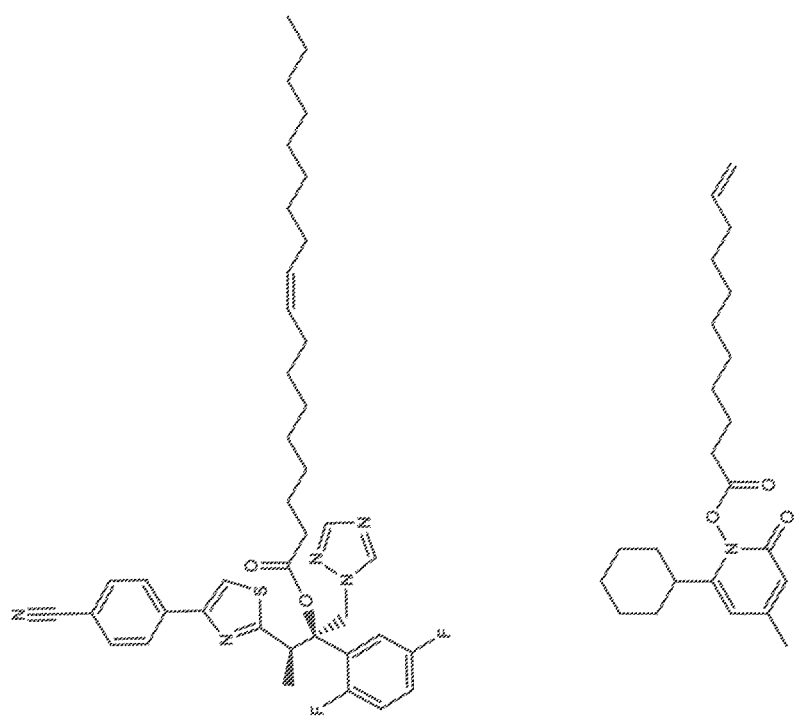
Figure 9A:
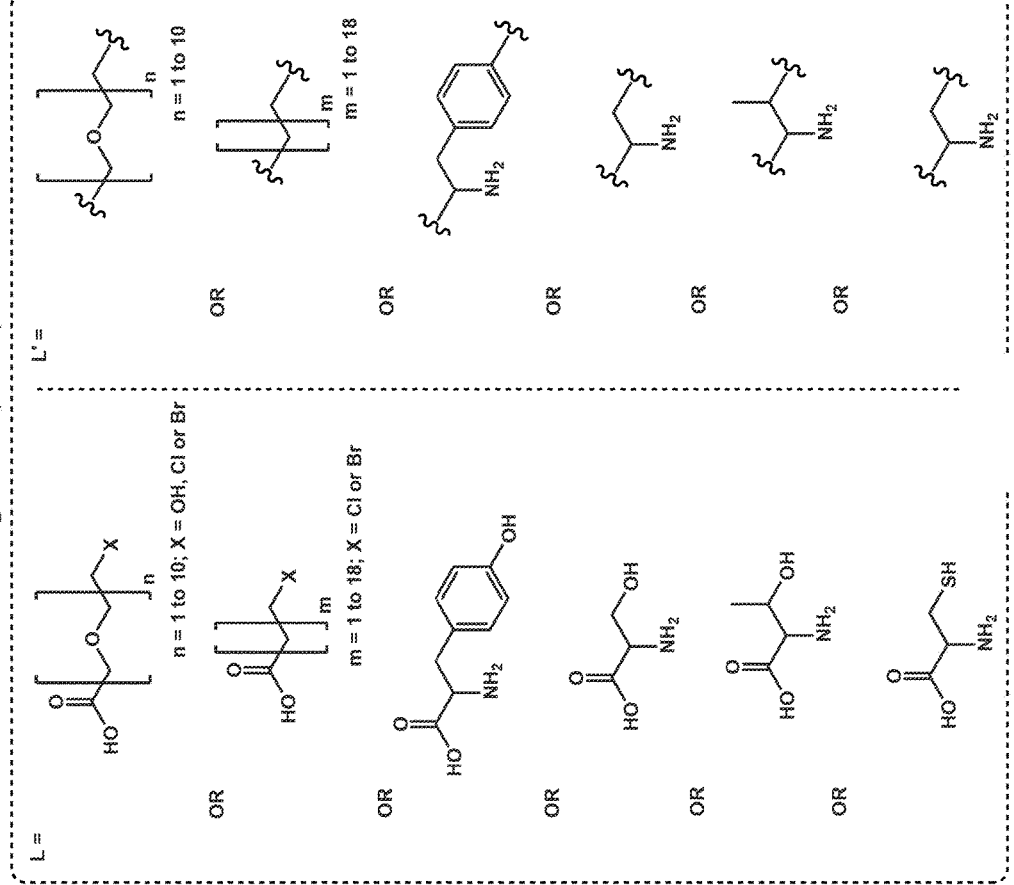
Figure 9B:
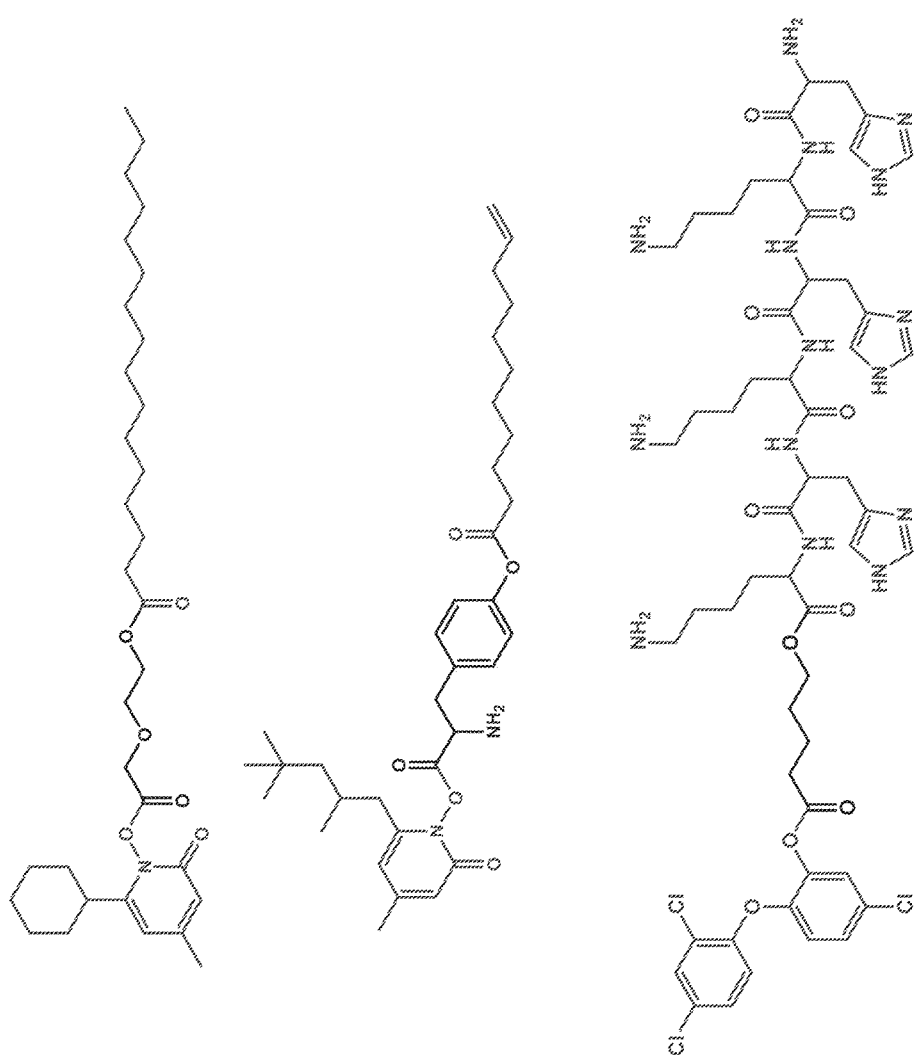
Figure 10A:
Figure 10B:
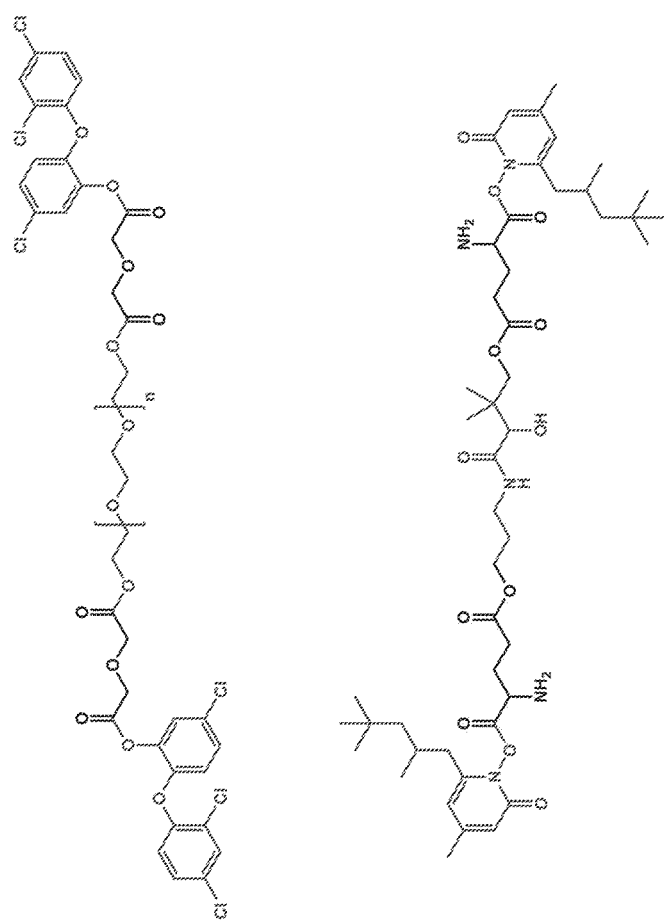
Figure 11A:
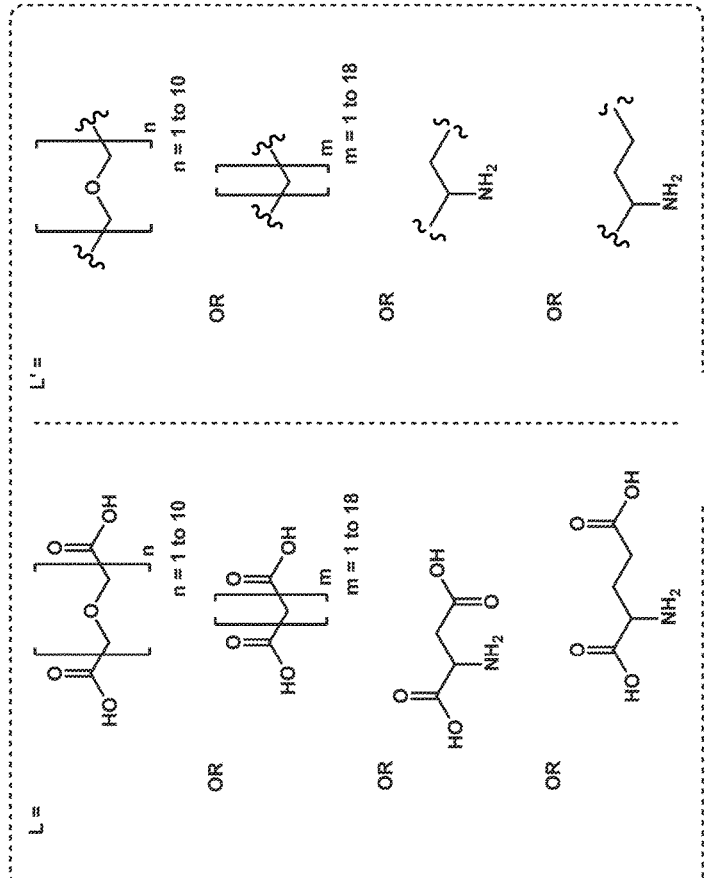
Figure 11B:
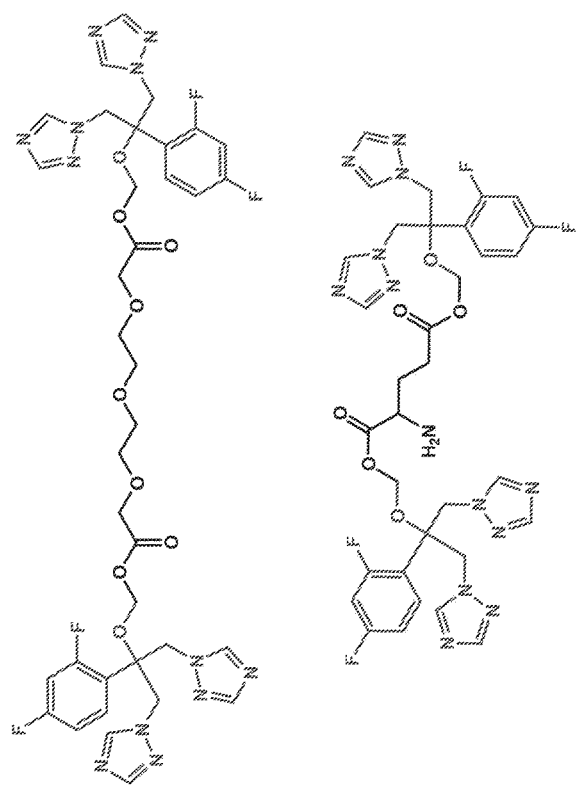
Figure 12A:
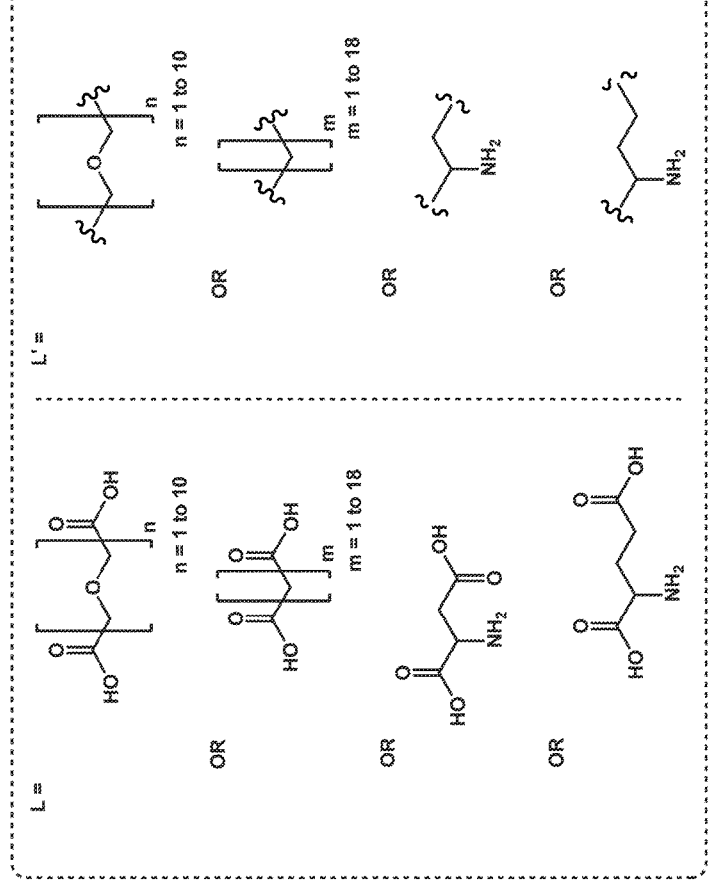
Figure 12B:
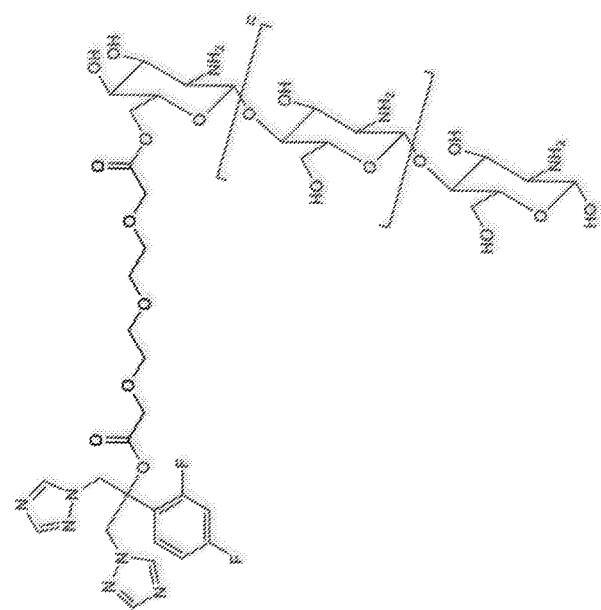
Figure 13:
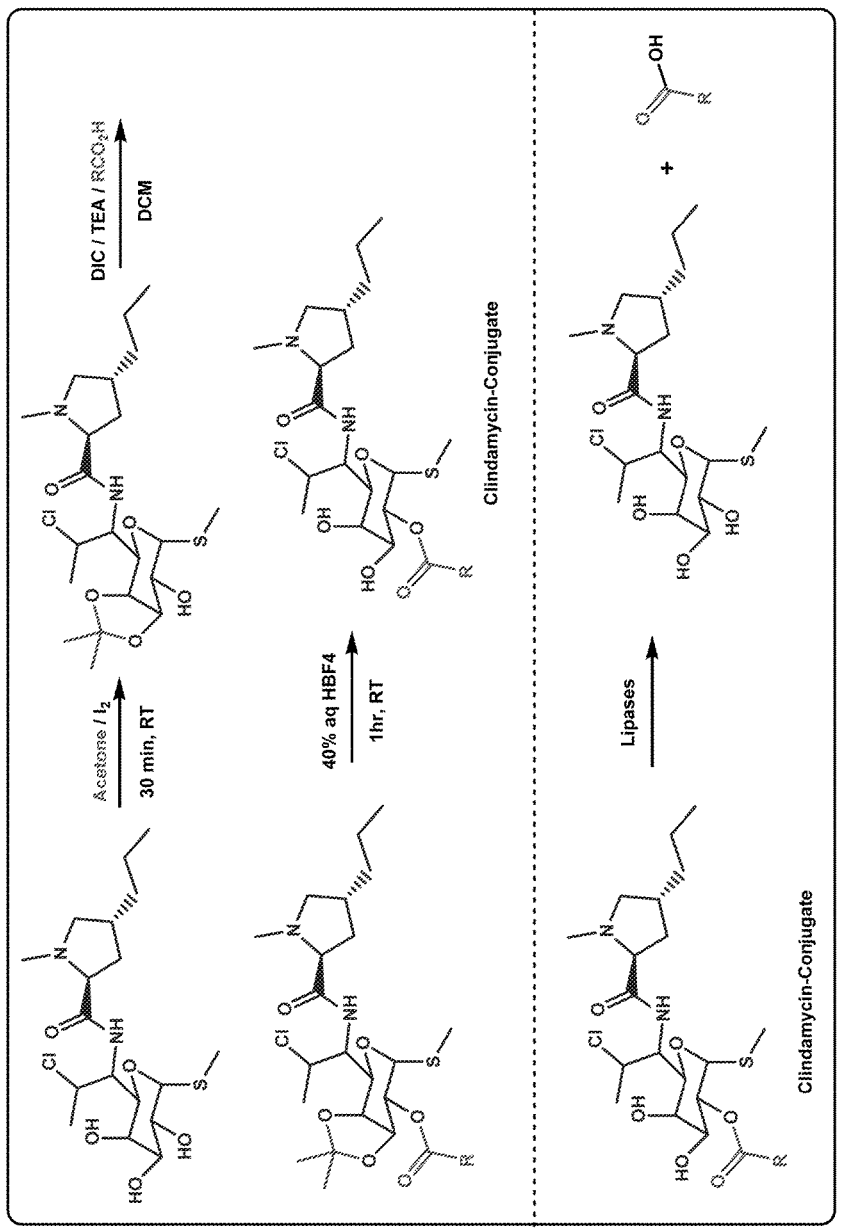
Figure 14:
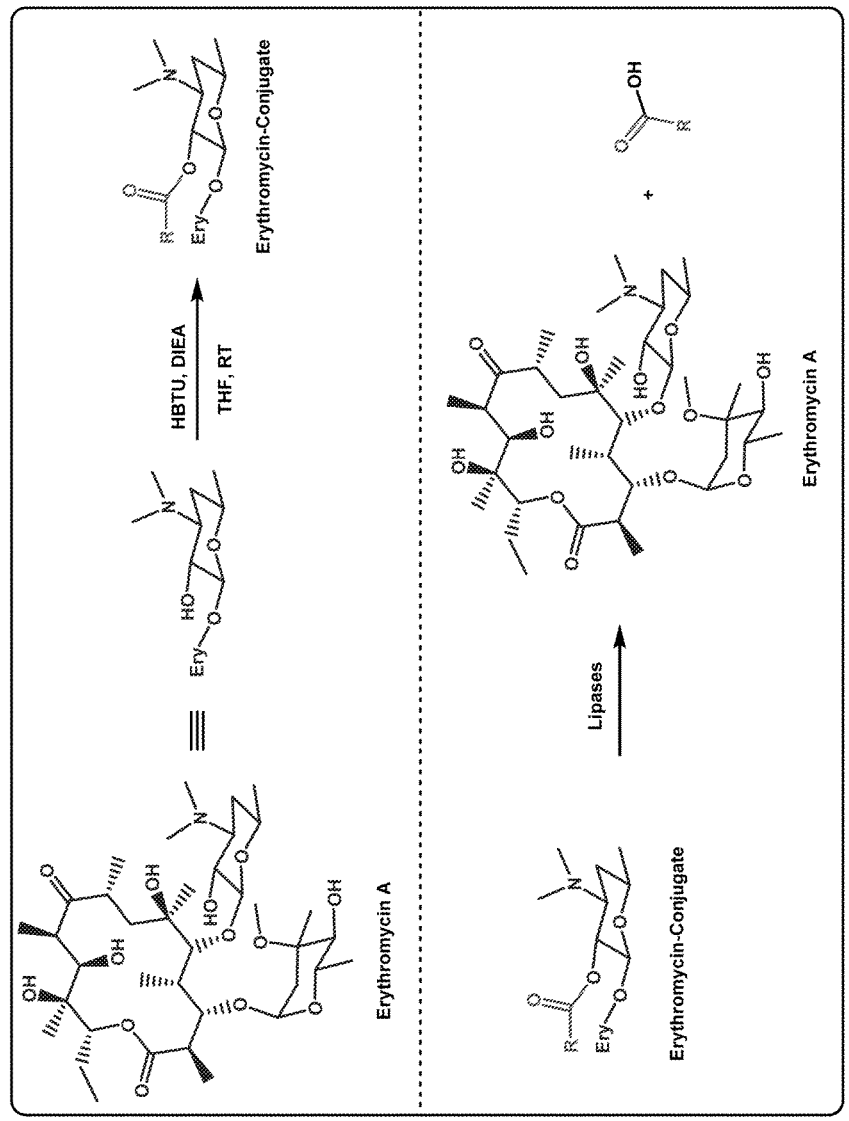
Figure 15:
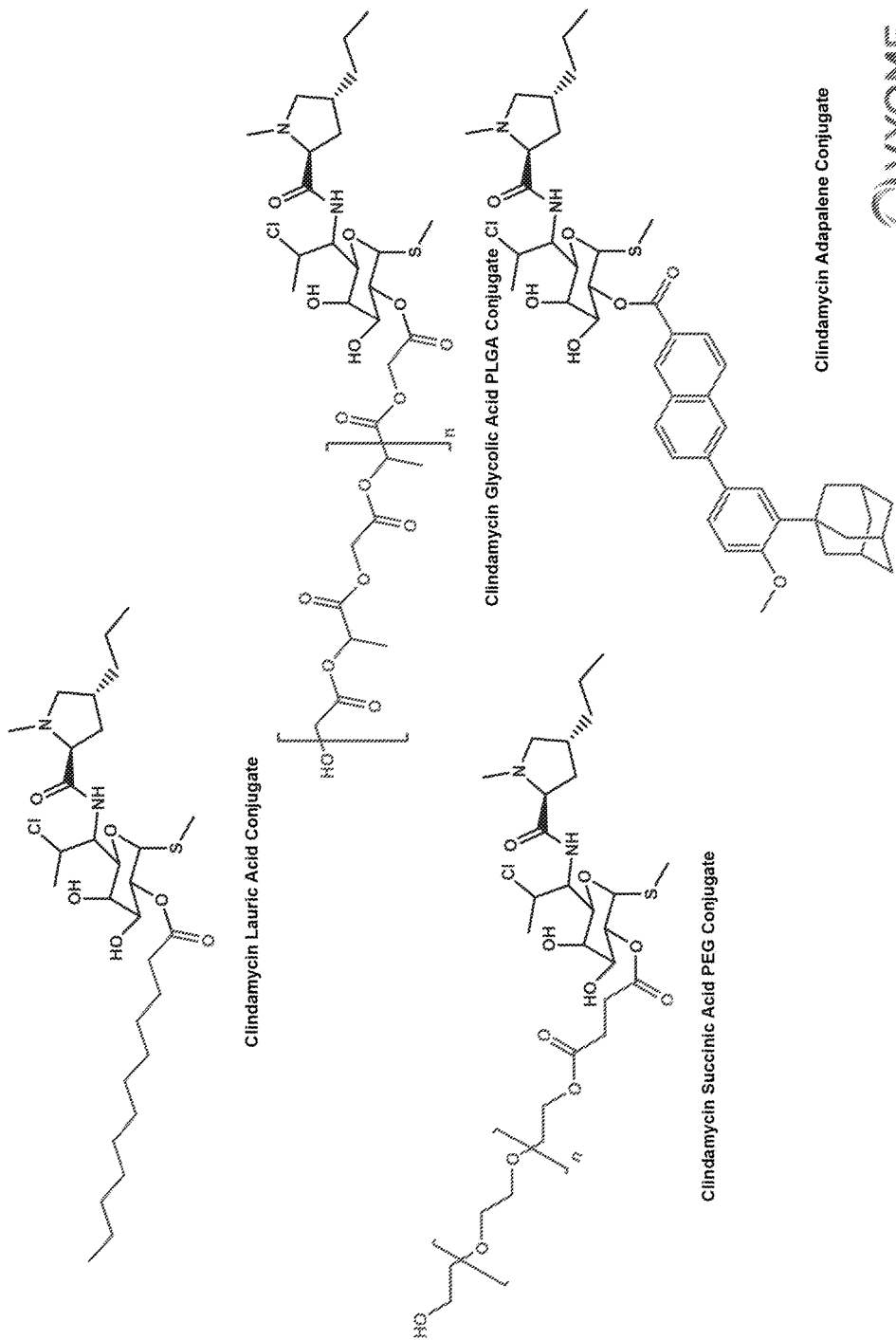

In some embodiments, linker is —CH($R^1$)—, wherein $R^1$ is H or $C_1$-$C_6$alkyl, which can be optionally substituted and/or interspersed with one or more of heteroatoms, aryls, heteroaryls, cyclyls, and heterocyclyls. In one embodiment of this linker $R^1$ is H or methyl, i.e., the linker is —$CH_2$— or —CH($CH_3$)—. As illustrated in FIG. 1, when this linker is used for linking an azole based antifungal or antibacterial agent with a carboxylated carrier, the conjugate can undergo spontaneous cleavage after the linkage is cleaved by an esterase to release the azole based agent and formaldehyde or acetaldehyde. A similar spontaneous cleavage can also happen when the linker is used for linking at a non-ring nitrogen atom of an antifungal or antibacterial agent. Some exemplary conjugates comprising this linker are shown in FIG. 1. Conjugates comprising this linker can be synthesized using an aldehyde, e.g. formaldehyde, acetaldehyde, paraformaldehyde and paraldehyde. While FIG. 1 shows this linker as being used for linking at the ring nitrogen of an azole moiety of the agent, this linker can also be used to link at a non-ring nitrogen of the agent. The second moiety in linked by this linker can comprise a carboxylic group or a hydroxyl group. Thus any moiety comprising a free carboxylic group or a free hydroxyl group can be conjugated with the agent. Accordingly, this linker can be used to link a second linker (e.g., a linker comprising a free carboxylic and/or a free hydroxyl group) to the agent, as shown in FIGS. 5-7.

Linker can be pyridoxine (vitamin $B_6$) or an analog or derivative thereof. Accordingly, in some embodiments, linker is

Figure 2B:
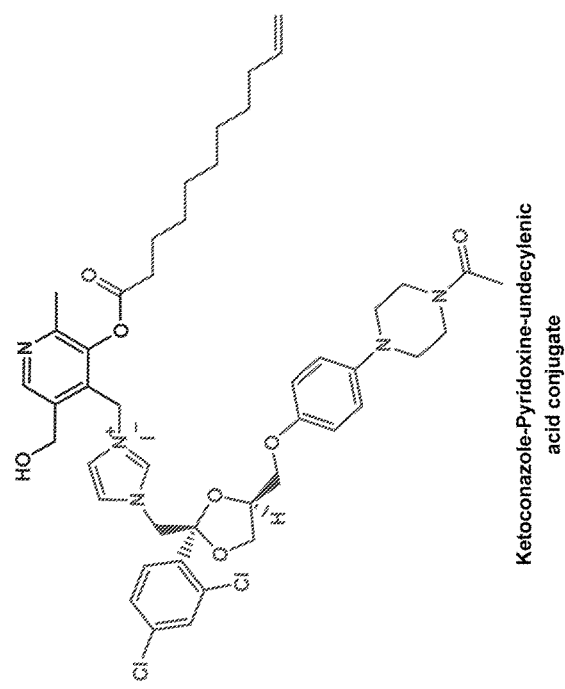

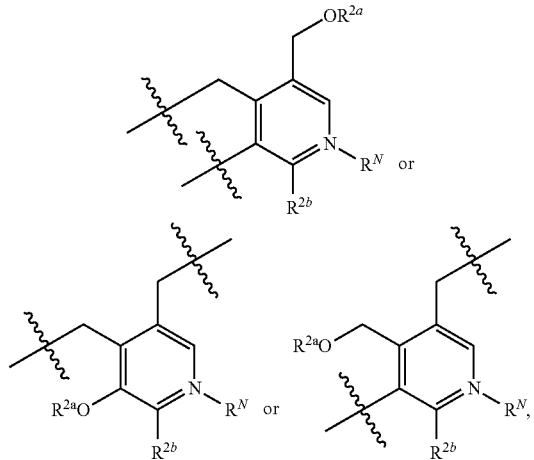

wherein $R^{2a}$ is a hydroxyl protecting group; $R^{2b}$ is $C_1$-$C_6$alkyl, which can be optionally substituted or interspersed with one or more heteroatoms, aryls, heteroaryls, cyclyls and heterocyclyls; and $R^N$ is absent, H, $C_1$-$C_6$ alkyl, or acyl, each of which can be optionally substituted. In some embodiments of this linker, $R^{2a}$ is an acyl group, i.e., C(O)$R^{2c}$, wherein $R^{2c}$ is $C_1$-$C_6$ alkyl. In one embodiment, $R^{2a}$ is C(O)$CH_3$. Preferably $R^{2b}$ is methyl or ethyl. When $R^N$ is the linker comprises a counter anion. Counter anion can be Cl$^-$, Br$^-$, I$^-$, or a pharmaceutically acceptable anion. Some exemplary conjugate comprising this linker are shown in FIG. 2. Conjugates comprising this linker can be synthesized utilizing pyridoxines.

In some embodiments, the linker is a polyethylene glycol (PEG) or an analog or derivative thereof. A PEG linker can be of the general formula —$CH_2CH_2$[O$CH_2CH_2$]$_a$O$CH_2CH_2$—, wherein a is 1-500. Suitable PEGs include, but are not limited to, PEG having an average molecular weight ranging from about 200 g/mole to about 30,000 g/mole. Conjugates comprising a PEG linker can by synthesized utilizing dihydroxyl PEGs of formula HO$CH_2CH_2$[O$CH_2CH_2$]$_a$O$CH_2CH_2$OH, wherein a is 1-500.

In some embodiments, the linker is —$CH_2$C($R^{3a}R^{3b}$)CH(O$R^{3c}$)C(O)N($R^{3d}$)—($CH_2$)$_b$—, wherein $R^{3a}$ and $R^{3b}$ are independently H or $C_1$-$C_6$ alkyl, which can be optionally substituted and/or interspersed with one or more heteroatoms, aryls, heteroaryls, cyclyls, and heterocyclyls; $R^{1c}$ is H or a carrier; $R^{3d}$ is H, alkyl, alkenyl, alkynyl, cyclyl, heterocyclyl, aryl, or heteroaryl, each of which can be optionally substituted; and b is 1-10. $R^{3a}$ and $R^{3b}$ can be the same or different. In one instance $R^{3a}$ and $R^{3b}$ are both methyl. In some embodiments of this linker, b is 2 or 3. This linker can be used to link together two antifungal or antibacterial agents. When used for linking two antifungal or antibacterial agents together, a carrier can be attached at the hydroxyl. Conjugates comprising this linker can be synthesized utilizing an aldehyde, e.g., paraformaldehyde or paraldehyde, and panthenols or dihydroxyl PEGs. Linkers of this type can undergo water mediated cleavage.

In some embodiments, the linker is

Figure 3B:
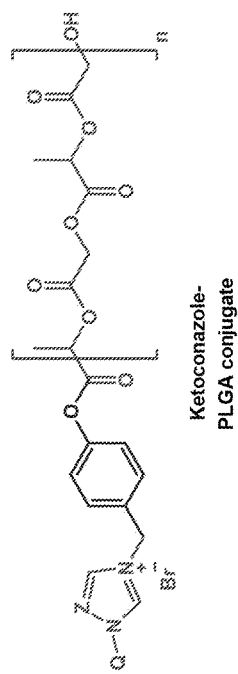
Figure 4A:
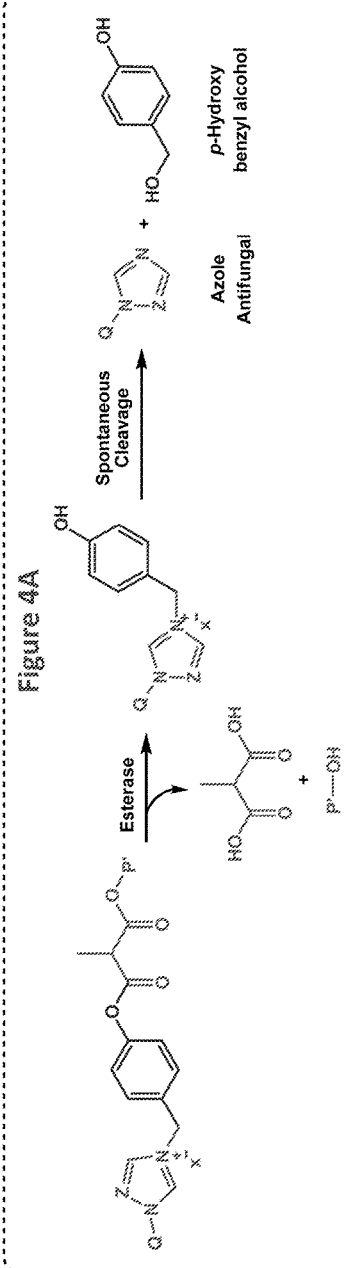
Figure 4B:
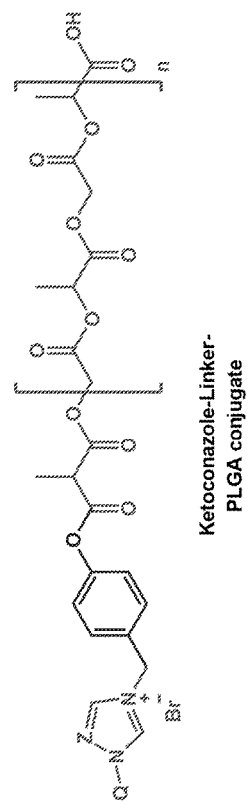

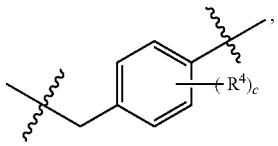

wherein $R^4$ is halo, CN, CF3, alkyl, alkenyl, cyclyl, heterocyclyl, aryl, heteroaryl, $NO_2$, $OR^6$, $OC(O)R^{4a}$, $OC(O)OR^{4a}$, $N(R^{4a})_2$, $NHC(O)R^{4a}$, $NHC(O)OR^4a$, $C(O)R^{4a}$, $C(O)OR^{4a}$, $SR^{4a}$, or $SO_2R^{4a}$, each of which can be optionally substituted; $R^{4a}$ is independently for each occurrence, H, alkyl, alkenyl, alkynyl, cyclyl, heterocyclyl, aryl, or heteroaryl, each of which can be optionally substituted; and c is 0 to 4. In one embodiment, c is 0. Conjugates comprising this linker can be synthesized utilizing a p-hydroxy benzyl alcohols. Some exemplary conjugates comprising this linker are shown in FIGS. 3 and 4. As shown in FIGS. 3 and 4, cleavage of this linker leads to the formation of p-hydroxy benzyl alcohol or an analog or derivative thereof.

In some embodiments, the linker is based on a glycol, e.g., —$CH_2CH(R^6)$—, wherein R is H or $C_1$-$C_6$ alkyl, which can be optionally substituted and/or interspersed with one or more heteroatoms, aryls, heteroaryls, cyclyls, and heterocyclyls. In one embodiment of this linker, $R^6$ is methyl. When this linker is used for linking an azole based antifungal or antibacterial agent with a carboxylated carrier, the conjugate undergoes spontaneous cleavage after the linkage cleavage by an esterase to release a glycol. Conjugate comprising this linker can be synthesized utilizing a glycol of the form $HOCH_2CH(R^6)OH$.

The linker can be based on an alpha-hydroxy acid or an analog or derivative thereof. Accordingly, in some embodiments, the linker is —$CH(R^7)C(O)$—, wherein $R^7$ is H, $C_1$-$C_6$alkyl, aryl, heteroaryl, cyclyl, or heterocyclyl, each of which can be optionally substituted and/or interspersed with one or more heteroatoms, aryls, heteroaryls, cyclyls and heterocyclyls. In one embodiment, $R^7$ is methyl. Generally, this linker is used to link a carrier at a hydroxyl group in the carrier. When this linker is used for linking an azole based antifungal or antibacterial agent with a hydroxyl comprising carrier, the conjugate undergoes spontaneous cleavage after the linkage cleavage by an esterase to release an alpha-hydroxy acid, e.g., lactic acid or an analog or derivative thereof. Conjugates comprising this linker can be synthesized using an alpha-hydroxy acids, such as glycolic acid, lactic acid, and mandelic acid.

In some embodiments, the linker is —$CH(R^8)OC(O)$-L'-$C(O)O$—, wherein $R^8$ is H or $C_1$-$C_6$ alkyl; and L' is analkyl, which can be optionally substituted and/or interspersed with one or more heteroatoms, aryls, heteroaryls, cyclyls or heterocyclyls, each of which can be optionally substituted. In one embodiment of this linker, L' is —$(CH_2OCH_2)_d$—, wherein d is 1 to 500. In another embodiment of this, L' is —$(CH_2)_e$—, wherein e is 1 to 28. In yet another embodiment of this, L' is —$CH(N(R^N)_2)$—$(CH(R^{8a})_f$, wherein $R^{8a}$ is H or $C_1$-$C_6$alkyl; $R^N$ is independently for each occurrence, H, alkyl, alkenyl, alkynyl, cyclyl, heterocyclyl, aryl, or heteroaryl, each of which can be optionally substituted; and f is 1-10. Preferably f is 1, 2, or 3. Preferably $R^{8a}$ is H or methyl. In one embodiment, $R^N$ is methyl. In yet still another embodiment, L' is —O—$CH(R^{8b})$—, wherein $R^{8b}$ is H or $C_1$-$C_6$ alkyl. In one embodiment, $R^{8b}$ is methyl. In one embodiments, L' is —$CH_2CH_2C(O)O$—[$CH_2CH_2O]_fC(O)$ $CH_2CH_2$—, wherein f' is 1 to 500. This linker can be used to link carriers comprising a hydroxyl group. Conjugates comprising this linker can be synthesized utilizing an aldehyde, e.g., paraformaldehyde or paraldehyde, and a dicarboxylic acid, such as those shown in FIG. 5 and those described herein. Some exemplary conjugates comprising this linker are shown in FIG. 5. In one embodiment, the linker is azelaic acid.

In some embodiments, the linker is —$CH(R^9)OC(O)$— or —$CH(R^9)OC(O)$-L'- or —$CH(R^9)OC(O)$-L'-Y—$C(O)$—, wherein $R^9$ is H or $C_1$-$C_6$alkyl; Y is O, S, or NH; and L' is an alkyl, which can be optionally substituted and/or interspersed one or more heteroatoms, aryls, heteroaryls, cyclyls or heterocylcyls, each of which can be optionally substituted. In one embodiment of this linker, L' is —$(CH_2OCH_2)_gCH_2$—, wherein g is 1 to 500. In another embodiment of this, L' is —$(CH_2CH_2O)_gCH_2CH_2$—, wherein g is 1 to 500. In another embodiment of this, L' is —$(CH_2)_hCH_2$—, wherein h is 1 to 28. In yet another embodiment of this, L' is —$CH(N(R^N)_2(CH(R^{9a})_i$, wherein $R^{9a}$ is H or an optionally substituted $C_1$-$C_6$ alkyl; $R^N$ is independently for each occurrence, H, alkyl, alkenyl, alkynyl, cyclyl, heterocyclyl, aryl, or heteroaryl, each of which can be optionally substituted; and i is 1-10. Preferably i is 1, 2, or 3. In one embodiment, $R^N$ is methyl. In one embodiment, $R^{9a}$ is H or methyl. In yet still another embodiment, L' is —O—$CH(R^{8b})$—, wherein $R^{9b}$ is H or $C_1$-$C_6$ alkyl. In one embodiment, $R^{9b}$ is methyl. In one embodiments, L' is —$CH_2CH_2C(O)O$—[$CH_2CH_2O]_{i'}C(O)CH_2CH_2$—, wherein i' is 1 to 500. In some embodiments of this i' is In one embodiment of this linker, the linker is —$CH(CH_3)$—$OC(O)O$—[$CH_2CH_2O]_{i'}CH_2CH_2$—, wherein i' is 1 to 500. In one embodiment of this linker, the linker is —$CH(CH_3)$—$OC(O)O$—[$CH_2CH_2O]_{i'}CH_2CH_2$—, wherein i' is 1 to 500. In one embodiment of this linker, the linker is —$CH(CH_3)$—$OC(O)O$—[$CH_2CH_2O]_{i'}CH_2CH_2$—, wherein i' is 1, 2, 3, 4, 5, 6, 7, 8, 9, 10, 11, 12, 13, 14 or 15. In another embodiment of this linker, the linker is —$CH(CH_3)$—$OC(O)O$—[$CH_2CH_2O]_{i'}CH_2CH_2$—$OC(O)$—$CH(CH_3)$—, wherein i' is 1 to 500. In one embodiment of this linker, the linker is —$CH(CH_3)$—$OC(O)O$—[$CH_2CH_2O]_{i'}CH_2CH_2$—$OC(O)$—$CH(CH_3)$—, wherein i' is 1, 2, 3, 4, 5, 6, 7, 8, 9, 10, 11, 12, 13, 14 or 15. In yet another embodiment of this linker, the linker is —$CH_2$—$OC(O)O$—$(CH_2)_{h'}$—$C(O)$—, wherein h' is 1, 2, 3, 4, 5, 6, 7, 8, 9, 10, 11, 12, 13, 14, or 15. Conjugates comprising this linker can be synthesized utilizing an aldehyde, e.g., paraformaldehyde or paraldehyde, and a carboxylic acid, such as those shown in FIG. 6, or by utilizing 1-haloalkyl esters, e.g. a compound of. In some embodiments, a 1-haloalkylester can be 1-chloroethyl esters. Some exemplary conjugates comprising the linkers described in this paragraph are shown in FIG. 6.

In some embodiments, the linker is —$CH(R^{10a})OC(O)$-L'-$C(O)OCH(R^{10b})$—, wherein $R^{10a}$ and $R^{10b}$ are independently H or $C_1$-$C_6$ alkyl, which can be optionally substituted; and L' is an alkyl, which can be optionally substituted and/or interspersed one or more heteroatoms, aryls, heteroaryls, cyclyls or heterocylcyls, each of which can be optionally substituted. $R^{10a}$ and $R^{10b}$ can be the same or different. In one embodiment, $R^{10a}$ and $R^{10b}$ are both methyl. In one embodiment, $R^{10a}$ and $R^{10b}$ are both H. In one embodiment of this linker, L' is —$(CH_2OCH_2)_j$—, wherein j is 1 to 500. In another embodiment of this, L' is —$(CH_2)_k$—, wherein k is 1 to 28. In yet another embodiment of this, L' is —$CH(N(R^N)_2(CH(R^{10c})_l$, wherein $R^{10c}$ is H or an optionally substituted $C_1$-$C_6$ alkyl; $R^N$ is independently for each occurrence, H, alkyl, alkenyl, alkynyl, cyclyl, heterocyclyl, aryl, or heteroaryl, each of which can be optionally substituted; and t is 1-10. Preferably t is 1, 2, or 3. In one embodiment, $R^N$ is methyl. In one embodiment, $R^{10c}$ is H or methyl. In yet still another embodiment, L' is —O—CH($R^{10d}$)—, wherein $R^{10d}$ is H or $C_1$-$C_6$ alkyl. In one embodiment, $R^{10d}$ is methyl. In one embodiments, L' is $CH_2CH_2C(O)O$—[$CH_2CH_2O$]$_{t'}$C(O)$CH_2CH_2$—, wherein t' is 1 to 500. —$CH_2$—OC(O)—($CH_2$)$_{k'}$—C(O)O—$CH_2$—, wherein k' is 1, 2, 3, 4, 5, 6, 7, 8, 9, 10, 11, 12, 13, 14, or 15. In one embodiment of this, the linker is Conjugates comprising this linker can be synthesized utilizing an aldehyde, e.g., paraformaldehyde or paraldehyde, and a dicarboxylic acid, such as those shown in FIG. 7 and those described herein. Some exemplary conjugates comprising this linker are shown in FIG. 7.

In some embodiments, the linker is —C(O)-L'-C(O)—, —C(O)-L'-Y—, or —C(O)-L'-Y—C(O)—, wherein Y is O, S, or NH; and L' is analkyl, which can be optionally substituted and/or interspersed one or more heteroatoms, aryls, heteroaryls, cyclyls or heterocylcyls, each of which can be optionally substituted. In one embodiment of this linker, L' is —($CH_2OCH_2$)$_{a'}$—, wherein a' is 1 to 500. In another embodiment of this, L' is —($CH_2$)$_{b'}$—, wherein b' is 1 to 28. In some embodiments, L' is a $C_1$-$C_6$ alkyl, e.g., methyl, ethyl, propyl, butyl, pentyl, hexyl, or ethylene. In yet another embodiment of this, L' is —CH(N($R^N$)$_2$(CH($R^{11c}$)$_{c'}$, wherein $R^{11c}$ is H or an optionally substituted $C_1$-$C_6$ alkyl; $R^N$ is independently for each occurrence, H, alkyl, alkenyl, alkynyl, cyclyl, heterocyclyl, aryl, or heteroaryl, each of which can be optionally substituted; and c' is 1-10. Preferably c' is 1, 2, or 3. In one embodiment, $R^N$ is methyl. In one embodiment, $R^{11c}$ is H or methyl. In yet still another embodiment, L' is —O—CH($R^{11d}$)—, wherein $R^{11d}$ is H or $C_1$-$C_6$ alkyl. In one embodiment, $R^{11d}$ is methyl. In one embodiments, L' is —$CH_2CH_2C(O)O$—[$CH_2CH_2O$]$_{d'}$C(O)$CH_2CH_2$—, wherein d' is 1 to 500. Conjugates comprising this linker can be synthesized using dicarboxylic acids, such as Oxalic acid, Malonic acid, Succinic acid, Glutaric acid, Adipic acid, Pimelic acid, Suberic acid, Azelaic acid, Sebacic acid, undecanedioic acid, and dodecanedioic acid. Additionally, conjugates comprising this linker can be synthesized using the diacids shown in FIGS. 11 and 12. Some exemplary conjugates comprising this linker are shown in FIGS. 11, 12, and 17-21. This type of linker can be used to conjugate together two antifungal and/or antibacterial agents as shown in FIGS. 17-21. The two linked together antifungal and/or antibacterial agents can be the same or different.

Figure 16:
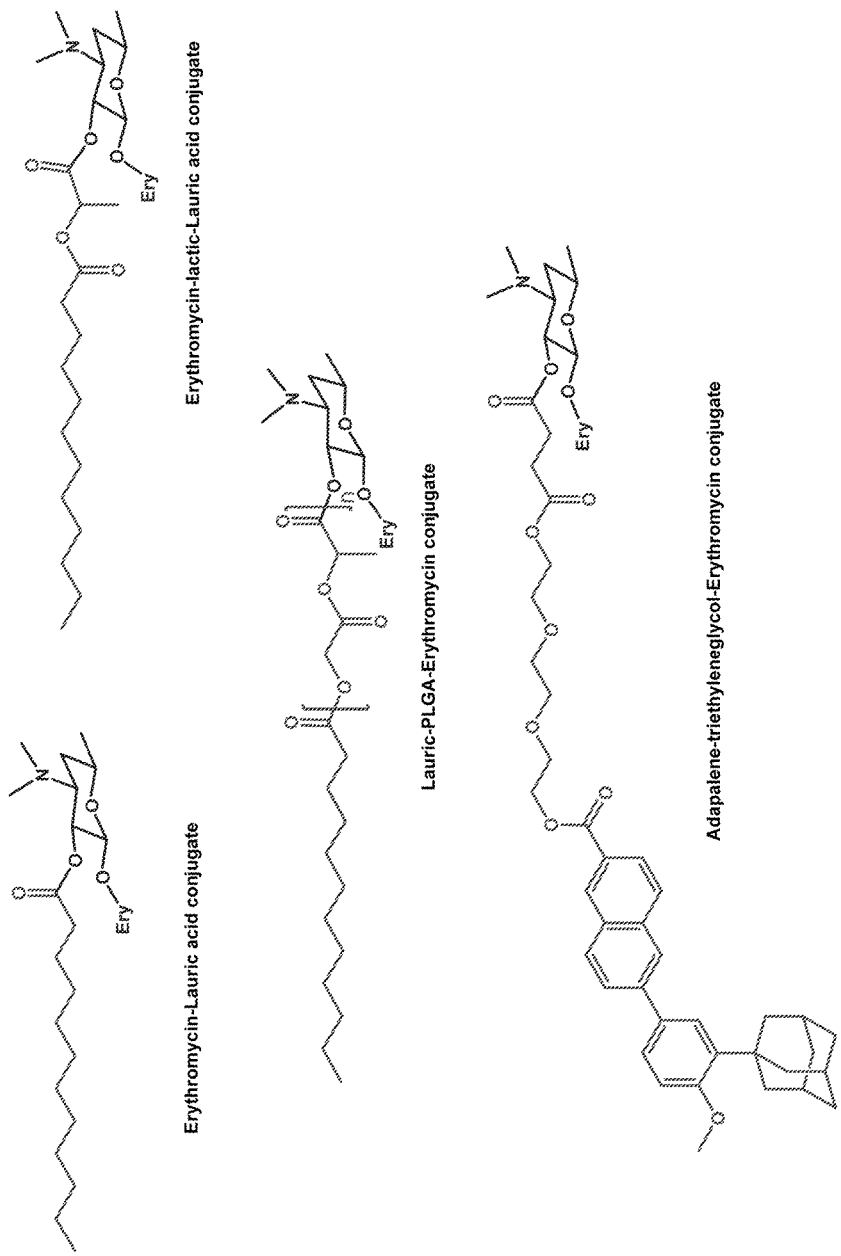

In some embodiments, the linker is —C(O)-L'-C(O)O—[$CH_2CH_2O$]$_{v'}$—, wherein v' is 1-500 and L' is $C_1$-$C_{10}$ alkyl, which can be optionally substituted and/or interspersed one or more heteroatoms, aryls, heteroaryls, cyclyls or heterocylcyls, each of which can be optionally substituted. In one embodiment of this linker, L' is —($CH_2OCH_2$)$_{e'}$—, wherein e' is 1 to 500. In another embodiment of this, L' is —($CH_2$)$_{f'}$—, wherein f' is 1 to 28. In some embodiments, L' is a $C_1$-$C_6$ alkyl, e.g., methyl, ethyl, propyl, butyl, pentyl, hexyl, or ethylene. In yet another embodiment of this, L' is —CH(N($R^N$)$_2$(CH($R^{12c}$)$_{g'}$, wherein $R^{12c}$ is H or an optionally substituted $C_1$-$C_6$ alkyl; $R^N$ is independently for each occurrence, H, alkyl, alkenyl, alkynyl, cyclyl, heterocyclyl, aryl, or heteroaryl, each of which can be optionally substituted; and g' is 1-10. Preferably g' is 1, 2, or 3. In one embodiment, $R^N$ is methyl. In one embodiment, $R^{12c}$ is H or methyl. In yet still another embodiment, L' is —O—CH($R^{13d}$)—, wherein $R^{13d}$ is H or $C_1$-$C_6$ alkyl. In one embodiment, $R^{13d}$ is methyl. In one embodiments, L' is —$CH_2CH_2C(O)O$—[$CH_2CH_2O$]$_{h'}$C(O)$CH_2CH_2$—, wherein h' is 1 to 500. Conjugates comprising this linker can be synthesized using a dicarboxylic acid and a PEG. Some exemplary conjugates comprising this linker are shown in FIG. 16.

A linker can be dicarboxylic acid. Exemplary dicarboxylic acids include, but are not limited to, Acetonedicarboxylic acid; Acetylenedicarboxylic acid; N-Acetylglutamic acid; ACPD; Adipic acid; Aldaric acid; 2-Amino-3-carboxymuconic semialdehyde; Alpha-Aminoadipic acid; 2-Aminomuconic acid; Aspartic acid; Azelaic acid; 4,4'-Azobis(4-cyanopentanoic acid); Bacillithiol; Bicinchoninic acid; Camphoric acid; Carbamoyl aspartic acid; Carbocisteine; Cichoric acid; Cilastatin; Clinofibrate; Diaminopimelic acid; Diglycolic acid; Dihydroxymalonic acid; Dimer acid; Dimercaptosuccinic acid; Dipicolinic acid; Docosanedioic acid; Dodecanedioic acid; Folic acid; Fumaric acid; Fumarylacetoacetate; 2,5-Furandicarboxylic acid; Glutaconic acid; Glutamic acid; 4-(γ-Glutamylamino)butanoic acid; Glutaric acid; 3-Hydroxyaspartic acid; Alpha-Hydroxyglutaric acid; Hypoglycin B; Iminodiacetic acid; Indicaxanthin; Isophthalic acid; Itaconic acid; Alpha-Ketoadipic acid; Alpha-Ketoglutaric acid; Lepidolide; Maleic acid; Maleylacetic acid; Malic acid; Malonic acid; Meconic acid; Meglutol; Mesaconic acid; Mesoxalic acid; N-Methyl-D-aspartic acid; 3-Methylglutaconic acid; Methylmalonic acid; Muconic acid; Nedocromil; Oxalic acid; Oxaloacetic acid; Oxalyldiaminopropionic acid; N-Oxalylglycine; Pamoic acid; PCCG-4; Phthalic acid; Pimelic acid; Prephenic acid; Quinolinic acid; Sebacic acid; Stizolobic acid; Suberic acid; Succinic acid; Tartaric acid; Tartronic acid; Terephthalic acid; Thiomalic acid; Tidiacic; and Traumatic acid. Additionally, polymers comprising two or more carboxylic groups can also be used as a linker like a dicarboxylic acid. Some exemplary conjugates comprising a dicarboxylic acid as a linker are shown in FIG. 17-21.

In some embodiments, linker is a beta-hydroxy acid. Examples of beta hydroxy acids which can be used as linkers include, but are not limited to, 3-hydroxyl-alkanoic acids where the alkane is selected from alkanes having about 3 to about 25 carbon atoms. Some beta-hydroxy acids are 3-hydroxy butyric acid, 3-hydroxy pentanoic acid, 3-hydroxy caproic acid, tropic acid, and trethocanic acid. Other suitable beta-hydroxy acids are described in U.S. Pat. No. 5,665,776. One preferred beta-hydroxy acid for use as a linker is salicylic acid.

Beta hydroxyl acid (BHA) is oil-soluble. Accordingly, BHA works very well in clearing up whiteheads and blackheads by penetrating inside pores that are clogged with sebum and a buildup of dead cells. BHA is a powerful exfoliant that breaks down skin plugs in the pores and is able to reach deeper into infected pores than alpha hydroxy acid. BHA has a lower risk of skin irritation due to its anti-inflammatory action. BHA can reduce mottled appearance of sun damaged skin. Potential side effects of BHA include itchiness, pain, burning and redness. The risk of scarring in darker people is high.

One exemplary BHA is salicylic acid. Salicylic acid is effective in reducing and eliminating calluses, eczema, psoriasis, warts and dandruff. Salicylic acid works by promoting the shedding of damaged skin cells and growth of new ones. It keeps the pores of the skin clear, hence minimizes clogging and actively breaks down all forms of acne. Salicylic acid loosens dry and damaged skin patches by softening epidermal protein-keratin. It remains on the skin surface long enough to sufficiently treat the pores. Salicylic acid is safe for sensitive skin; minor side effects include dryness, light stinging sensation, redness and peeling.

In some embodiments, the linker is a polyhydroxy acid, which typically are organic carboxylic compounds having at least two hydroxyl groups in the molecules and with preferred molecular weight of between about 100 and about 300. The polyhydroxy acids can be divided into aldonic acids, aldaric acids, and alduronic acids. These polyhydroxy acids include gluconic acid, ribonic acid, galactonic acid, glucoheptonic acid, glucuronic acid, galacturonic acid, glucaric acid, galactaric acid, lactobionic acid, and the like.

Alpha hydroxyl acid (AHA) works by preventing cells from adhering to one another on the skin surface. AHA can cause the top layer of the skin to peel and shed, revealing new and smoother skin underneath. It is effective in clearing skin problems such as eczema, psoriasis, acne, and age spots; and helps stimulate collagen growth in the cells. One major side effect of AHA is increase in sun sensitivity of application area. AHA can cause irritation, redness, itching, or burning of the skin and can sometimes lead to scarring of darker skin tones.

One exemplary AHA is glycolic acid. Glycolic acid has an excellent capability to penetrate the skin. Glycolic acid reduces wrinkles, scarring and hyperpigmentation and many other skin conditions like actinic keratosis, hyperkeratosis, seborrheic keratosis, and can be used to improve skin appearance and texture. Glycolic acid reacts with the upper layer of the epidermis, weakening the binding properties of the lipids that hold the dead skin cells together. This allows the stratum corneum to be exfoliated, exposing live skin cells. It can be a skin irritant.

Another AHA is mandelic acid. Mandelic acid possesses antibacterial properties and is used as an alternative to glycolic acid in skin care.

While AHA is a single strand molecule allowing for quick penetration to the skin; polyhydroxy acid (PHA) is a multiple strand molecule (and larger size) making it slower in penetrating the skin. PHA is absorbed at a slower rate, which can reduce side effects such as stinging or irritation. PHA are considered as next generation of AHA's as they can be natural and non-toxic. PHA can modulate kertinization, cell development in the top layer of the skin, and normalize stratum corneum exfoliation and thickness. Gentle topical penetration decreases sensitivity and discomfort. Exemplary PHA include, but are not limited to lactobionic acid, galactose and gluconic acid.

Lactobionic acid is a PHA derived from lactose in cow's milk (gluconolactone+galactose). It out performs other humectants such as glycerol, sorbitol, and glycolic acid due to it's eight hydroxyl groups that bind more water. Lactobionic acid has antioxidant properties to block oxygen free radical induced tissue damage. It forms a gel film, which binds to the skin providing soothing and healing benefits and increases hydration and plumping. It has an anti-aging benefit especially targeted for sensitive skin.

Galactose is a PHA which is chemically neutral. Galactose helps in wound healing and protein synthesis. Galactose is utilized in callagen synthesis and cell migration which can enhance wound healing.

Gluconic acid is PHA which is known to provide beneficial effects to the skin.

When a carbohydrate, also called aldose, is oxidized at the carbon one position from an aldehyde to a carboxyl group, the product is called aldonic acid. For example, when glucose is oxidized at the carbon one position, the product is gluconic acid. The aldonic acid usually has multiple hydroxyl groups. The aldonic acids can exist as stereoisomers as D, L and DL or R, S and RS forms. Many aldonic acids form intramolecular lactones, aldonolactones, by removing one mole of water between the carboxyl group and one hydroxyl group. The following are representative aldonic acids 2,3-dihydroxypropanoic acid (glyceric acid); 2,3,4-trihydroxybutanoic acids (stereoisomers; erythronic acid and erythronolactone, threonic acid and threonolactone); 2,3,4,5-tetrahydroxypentanoic acids (stereoisomers; ribonic acid and ribonolactone, arabinoic acid and arabinolactone, xylonic acid and xylonolactone, lyxonic acid and lyxonolactone); 2,3,4,5,6-pentahydroxyhexanoic acids (stereoisomers; allonic acid and allonolactone, altronic acid and altronolactone, gluconic acid and gluconolactone, mannoic acid and mannolactone, gulonic acid and gulonolactone, idonic acid and idonolactone, galactonic acid and galactonolactone, talonic acid and talonolactone); 2,3,4,5,6,7-hexahydroxyheptanoic acids (stereoisomers; alloheptonic acid and alloheptonolactone, altroheptonic acid and altroheptonolactone, glucoheptonic acid and glucoheptonolactone, mannoheptonic acid and mannoheptonolactone, guloheptonic acid and guloheptonolactone, idoheptonic acid and idoheptonolactone, galactoheptonic acid and galactoheptonolactone, taloheptonic acid and taloheptonolactone).

The aldaric acid typically has multiple hydroxyl groups attached to the carbon chain surrounded by two carboxyl groups. Many aldaric acids form intramolecular lactones, aldarolactones, by removing one mole of water between one of the two carboxyl groups and one hydroxyl group, such as glucarolactone from glucaric acid. The aldaric acids can exist as stereoisomers as D, L and DL or R, S and RS forms. Exemplary aldaric acids include, but are not limited to, 2,3-dihydroxybutane-1,4-dioic acids (stereoisomers; erythraric acid and threaric acid); 2,3,4-trihydroxypentane-1,5-dioic acids (stereoisomers; ribaric acid and ribarolactone, arabaric acid and arabarolactone, xylaric acid and xylarolactone, lyxaric acid and lyxarolactone); 2,3,4,5-tetrahydroxyhexane-1,6-dioic acids (stereoisomers; allaric acid and allarolactone, altraric acid and altrarolactone, glucaric acid and glucarolactone, mannaric acid and mannarolactone, gularic acid and gularolactone, idaric acid and idarolactone, galactaric acid and galactarolactone, talaric acid and talarolactone); 2,3,4,5,6-pentahydroxyheptane-1,7-dioic acids (stereoisomers; alloheptaric acid and alloheptarolactone, altroheptaric acid and altroheptarolactone, glucoheptaric acid and glucoheptarolactone, mannoheptaric acid and mannoheptarolactone, guloheptaric acid and guloheptarolactone, idoheptaric acid and idoheptarolactone, galactoheptaric acid and galactoheptarolactone, taloheptaric acid and taloheptarolactone).

Alduronic acid is typically obtained from a carbohydrate, aldose, by oxidation of the terminal carbon to carboxyl group, and the carbon one position remains as aldehyde group, such as glucuronic acid from glucose. Similar to aldonic acid and aldaric acid, alduronic acid also has multiple hydroxyl groups attached to the carbon chain between two functional groups, one aldehyde and one carboxyl groups in this case. Many alduronic acids exist as intramolecular lactones, alduronolactones, such as glucuronolactone from glucuronic acid. The alduronic acids can exist as stereoisomers as D, L and DL or R, S and RS forms. Exemplary alduronic acids include, but are not limited to, erythruronic acid and threuronic acid, riburonic acid and riburonolactone, araburonic acid and araburonolactone, xyluronic acid and xyluronolactone, lyxuronic acid and lyxuronolactone, alluronic acid and alluronolactone, altruronic acid and altruronolactone, glucuronic acid and glucuronolactone, mannuronic acid and mannuronolactone, guluronic acid and guluronolactone, iduronic acid and iduronolactone, galacturonic acid and galacturonolactone, taluronic acid and taluronolactone, allohepturonic acid and allohepturonolactone, altrohepturonic acid and altrohepturonolactone, glucohepturonic acid and glucohepturonolactone, mannohepturonic acid and mannohepturonolactone, gulohepturonic acid and gulohepturonolactone, idohepturonic acid and idohepturonolactone, galactohepturonic acid and galactohepturonolactone, talohepturonic acid and talohepturonolactone.

In some embodiments, the linker is a direct bond. Exemplary conjugate having a bond as a linker include clindamycin lauric acid conjugate, clindamycin adapalenme conjugate, and erthyromycin-lauric acid conjugate shown in FIGS. 16 and 17.

In some embodiments, the linker is PLGA, PLA. Exemplary conjugate comprising PLGA as linker are shown in FIG. 17.

In some embodiments, the linker is a branched linker. The branch-point of the branched linker may be at least trivalent, but can be a tetravalent, pentavalent or hexavalent atom, or a group presenting such multiple valencies. In some embodiments, the branchpoint is, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branch-point is glycerol or a derivative thereof.

The linkers described herein can be used together to form a longer linker comprising two or more of the linkers described herein. For example a —CH($R^1$)— type linker can be linked to a linker based on a carboxylic acid molecule. One such exemplary extended linker is —CH($R^9$)OC(O)— or —CH($R^9$)OC(O)-L'- or —CH($R^9$)OC(O)-L'-Y—C(O)— as described above.

In some embodiments, the conjugate-based prodrugs of the invention can comprise two or more carrier molecules. When two or more carriers are present in a conjugated prodrug, all carriers can be the same, all different, or a combination of same and different. Without limitations, each carrier can be linked by a similar linker or by a different type of linker.

Personal Care Compositions

The conjugate-based prodrugs of the invention can be used in personal care compositions, such as hair care compositions and skin care compositions. The personal care composition of the present invention comprises an effective amount of at least one conjugate-based prodrug, ranging from about 0.001% to about 10%, preferably from about 0.1% to about 5%, and more preferably from about 0.5% to about 3% by weight relative to the total weight of the composition. As used here, the term "effective amount" is that amount of the conjugate-based prodrug in the personal care composition necessary to achieve the desired improvement.

In addition to the conjugate-based prodrug, a personal care composition of the invention can also include other pharmaceutical or topical agents for synergetic or synergistic effects. The pharmaceutical and other topical agents which can be incorporated into the compositions include those that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotion sickness agents; antiinflammatory agents; antihyperkeratolytic agents; antiperspirants; antpsoriatic agents; antiseborrheic agents; hair conditioners and hair treatment agents; antiaging and antiwrinkle agents; sunblock and sunscreen agents; skin lightening agents; depigmenting agents; vitamins; corticosteroids; tanning agents; humectants; hormones; retinoids; gum disease or oral care agents; topical cardiovascular agents; corn, callus and wart removing agents; and depilating agents.

Examples of the above agents include, but are not limited to, azelaic acid, triclosan, alpha-hydroxy acids, glycolic acid, mandelic acid, beta-hydroxy acids, salicylic acid, polyhydroxy acids, lactobionic acid, galactose, gluconic acid, adapalene, abacavir, acebutolol, acetaminophen, acetaminosalol, acetazolamide, acetohydroxamic acid, acetylsalicylic acid, acitretin, aclovate, acrivastine, actiq, acyclovir, adapalene, adefovir dipivoxil, adenosine, albuterol, alfuzosin, allopurinol, alloxanthine, almotriptan, alprazolam, alprenolol, aluminum acetate, aluminum chloride, aluminum chlorohydroxide, aluminum hydroxide, amantadine, amiloride, aminacrine, aminobenzoic acid (PABA), aminocaproic acid, aminosalicylic acid, amiodarone, amitriptyline, amlodipine, amocarzine, amodiaquin, amorolfine, amoxapine, amphetamine, ampicillin, anagrelide, anastrozole, anthralin, apomorphine, aprepitant, arbutin, aripiprazole, ascorbic acid, ascorbyl palmitate, atazanavir, atenolol, atomoxetine, atropine, azathioprine, azelaic acid, azelastine, azithromycin, bacitracin, beclomethasone dipropionate, bemegride, benazepril, bendroflumethiazide, benzocaine, benzonatate, benzophenone, benztropine, bepridil, betamethasone dipropionate, betamethasone valerate, brimonidine, brompheniramine, bupivacaine, buprenorphine, bupropion, burimamide, butenafine, butoconazole, cabergoline, caffeic acid, caffeine, calcipotriene, camphor, candesartan cilexetil, capsaicin, carbamazepine, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clomiphene, clonidine, clopidogrel, clotrimazole, clozapine, cocaine, codeine, cromolyn, crotamiton, cyclizine, cyclobenzaprine, cycloserine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamnide, dopamine, dorzolamide, doxepin, doxorubicin, doxycycline, doxylamine, doxypin, duloxetine, dyclonine, econazole, eflormthine, eletriptan, emtricitabine, enalapril, ephedrine, epinephrine, epinine, epirubicin, eptifibatide, ergotarnine, erythromycin, escitalopram, esmolol, esomeprazole, estazolam, estradiol, ethacrynic acid, ethinyl estradiol, etidocaine, etomidate, famciclovir, famotidine, felodipine, fentanyl, ferulic acid, fexofenadine, flecainide, fluconazole, flucytosiine, fluocinolone acetonide, fluocinonide, 5-fluorouracil, fluoxetine, fluphenazine, flurazepam, fluvoxamine, formoterol, furosemide, galactarolactone, galactonic acid, galactonolactone, galantamine, gatifloxacin, gefitinib, gemcitabine, gemifloxacin, glycolic acid, griseofulvin, guaifenesin, guanethidine, N-guanylhistamine, haloperidol, haloprogin, hexylresorcinol, homatropine, homosalate, hydralazine, hydrochlorothiazide, hydrocortisone, hydrocortisone 21-acetate, hydrocortisone 17-butyrate, hydrocortisone 17-valerate, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loperamide, losartan, loxapine, lysergic diethylamide, mafenide, malic acid, maltobionic acid, mandelic acid, maprotiline, mebendazole, mecamylamine, meclizine, meclocycline, memantine, menthol, meperidine, mepivacaine, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, nicardipine, nicotine, nifedipine, nimodipine, nisoldipine, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate O, palonosetron, pantothenic acid, pantoyl lactone, paroxetine, pemoline, penciclovir, penicillamine, penicillins, pentazocine, pentobarbital, pentostatin, pentoxifylline, pergolide, perindopril, permethrin, phencyclidine, phenelzine, pheniramine, phenmetrazine, phenobarbital, phenol, phenoxybenzamine, phentolamine, phenylephrine, phenylpropanolamine, phenytoin, physostigmine, pilocarpine, pimozide, pindolol, pioglitazone, pipamazine, piperonyl butoxide, pirenzepine, podofilox, podophyllin, pratipexole, pramoxine, prazosin, prednisone, prenalterol, prilocaine, procainamide, procaine, procarbazine, promazine, promethazine, promethazine propionate, propafenone, propoxyphene, propranolol, propylthiouracil, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivasfigmine, rizatriptan, ropinirole, ropivacaine, salicylamide, salicylic acid, salmeterol, scopolamine, selegiline, selenium sulfide, serotonin, sertindole, sertraline, sibutramine, sildenafil, sotalol, streptomycin, strychnine, sulconazole, sulfabenz, sulfabenzamide, sulfabromomethazine, sulfacetamide, sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, tadalafil, tamsulosin, tartaric acid, tazarotene, tegaserol, telithromycin, telmisartan, temozolomide, tenofovir disoproxil, terazosin, terbinafine, terbutaline, terconazole, terfenadine, tetracaine, tetracycline, tetrahydrozoline, theobromine, theophylline, thiabendazole, thioridazine, thiothixene, thymol, tiagabine, timolol, tinidazole, tioconazole, tirofiban, tizanidine, tobramycin, tocainide, tolazoline, tolbutamide, tolnaftate, tolterodine, tramadol, tranylcypromine, trazodone, triamcinolone acetonide, triamcinolone diacetate, triamcinolone hexacetonide, triamterene, triazolam, triclosan, triflupromazine, trimethoprim, trimipramine, tripelennamine, triprolidine, trometamine, tropic acid, tyramine, undecylenic acid, urea, urocanic acid, ursodiol, vardenafil, venlafaxine, verapamil, vitamin E acetate, voriconazole, warfarin, xanthine, zafirlukast, zaleplon, zinc pyrithione, ziprasidone, zolmitriptan and Zolpidem.

Azelaic acid is a naturally occurring dicarboxylic acid. Azelaic acid can inhibit DNA synthesis of keratinocytes and is comedolyitc. Azelaic acid has a dosedependent antimicrobial effect on *S. epidermidis* and *P. acnes*. At higher concentrations, azelaic acid can impart a burning sensation.

Triclosan is an antibacterial agent found in a number of households items like first aid creams, mouthwashs, deodrants, toothpastes, hand soaps and face washs (Clearsil). Triclosan clears away the buildup of bacteria under the skins surface. Major benefit of triclosan is its ability to remain on the skin for prolonged periods of time. Triclosan is not very water soluble and has slow degradation time that allows it to remain on the skin and continue to destroy bacteria after washings. Overuse can cause development of new bacterial strains resistant to antibiotics and can cause environmental hazards. Tricolsan is most successful when combined with products containing benzoyl peroxide or salicylic acid. Triclosan can act as a protective agent that increases the longetivity and effectiveness of other treatments of acne.

Alpha hydroxyl acid (AHA) works by preventing cells from adhering to one another on the skin surface. AHA can cause the top layer of the skin to peel and shed, revealing new and smoother skin underneath. It is effective in clearing skin problems such as eczema, psoriasis, acne, and age spots; and helps stimulate collagen growth in the cells. One major side effect of AHA is increase in sun sensitivity of application area. AHA can cause irritation, redness, itching, or burning of the skin and can sometimes lead to scarring of darker skin tones.

One exemplary AHA is glycolic acid. Glycolic acid has an excellent capability to penetrate the skin. Glycolic acid reduces wrinkles, scarring and hyperpigmentation and many other skin conditions like actinic keratosis, hyperkeratosis, seborrheic keratosis, and can be used to improve skin appearance and texture. Glycolic acid reacts with the upper layer of the epidermis, weakening the bindingproperties of the lipids that hold the dead skin cells together. This allows the stratum corneum to be exfoliated, exposing live skin cells. It can be a skin irritant.

Another AHA is mandelic acid. Mandelic acid possesses antibacterial properties and is used as an alternative to glycolic acid in skin care.

Beta hydroxyl acid (BHA) is oil-soluble. Accordingly, BHA works very well in clearing up whiteheads and blackheads by penetrating inside pores that are clogged with sebum and a buildup of dead cells. BHA is a powerful exfoliant that breaks down skin plugs in the pores and is able to reach deeper into infected pores than alpha hydroxy acid. BHA has a lower risk of skin irritation due to its anti-inflammatory action. BHA can reduce mottled appearance of sun damaged skin. Potential side effects of BHA include itchiness, pain, burning and redness. The risk of scarring in darker people is high.

One exemplary BHA is salicylic acid. Salicylic acid is effective in reducing and eliminating calluses, eczema, psoriais, warts and dandruff. Salicylic acid works by promoting the shedding of damaged skin cells and growth of new ones. It keeps the pores of the skin clear, hence minimizes clogging and actively breaks down all forms of acne. Salicylic acid loosens dry and damaged skin patches by softening epidermal protein-keratin. It remains on the skin surface long enough to sufficiently treat the pores. Salicylic acid is safe for sensitive skin; minor side effects include dryness, light stinging sensation, redness and peeling.

While AHA is a single strand molecule allowing for quick penetration to the skin; polyhydroxy acid (PHA) is a multiple strand molecule (and larger size) making it slower in penetrating the skin. PHA is absorbed at a slower rate, which can reduce side effects such as stinging or irritation. PHA are considered as next generation of AHA's as they can be natural and non-toxic. PHA can modulate kertinization, cell development in the top layer of the skin, and normalize stratum corneum exfoliation and thickness. Gentle topical penetrationdecreases sensitivity and discomfort. Exemplary PHA include, but are not limited to lactobionic acid, galactose and gluconic acid.

Lactobionic acid is a PHA derived from lactose in cow's milk (gluconolactone+galactose). It out performs other humectants such as glycerol, sorbitol, and glycolic acid due to it's eight hydroxyl groups that bind more water. Lactobionic acid has antioxidant properties to block oxygen free radical induced tissue damage. It forms a gel film, which binds to the skin providing soothing and healing benefits and increases hydration and plumping. It has an anti-aging benefit especially targeted for sensitive skin.

Galactose is a PHA which is chemically neutral. Galactose helps in wound healing and protein synthesis. Galactose is utilized in callagen synthesis and cell migration which can enhance wound healing.

Gluconic acid is PHA which is known to provide beneficial effects to the skin.

Adapalene has been shown to enhance the efficacy of topical clindamycin. Application of adapalene gel to the skin 3-5 minutes before application of clindamycin enhances penetration of clindamycin into the skin. It has both exfoliating and anti-inflammatory effects. It is possibly more effective than tretinoin 0.025% gel in the treatment of acne.

The personal care compositions of the present invention can further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the compositions.

Non-limiting examples of optional components for use in the composition include a deposition aid, cationic polymers, nonionic polymers, dispersed particles, conditioning agents (silicones and organic conditioning oils), humectant, suspending agent, additional anti-dandruff actives, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, vitamins, antioxidants, preserving agents, fillers, surfactants, UVA and/or UVB sunscreens, fragrances, viscosifying agents, wetting agents, anionic polymers, nonionic polymers, amphoteric polymers, viscosity/foam stabilizers, opacifying/pearlizing agents, sequestering agents, stabilizing agents, hair conditioning agents, humectants, anti-static agents, antifreezing agents, buffering agents, dyes, and pigments. These adjuvants are well known in the field of cosmetics and are described in many publications, for example see *Harry's Book of Cosmeticology*, 8th edition, Martin Rieger, ed., Chemical Publishing, New York (2000).

The personal care compositions of the present invention can include a deposition aid. The deposition aid is included to effectively enhance deposition of the personal care composition components. The deposition aid can comprise any material that enhances the deposition of the personal care composition components onto the hair, scalp, or skin. Preferably, the deposition aids are cationic polymers. The concentration of the deposition aid in the personal care composition should be sufficient to effectively enhance the deposition of the components and typically range from about 0.05% to about 5%, preferably from about 0.075% to about 2.5%, more preferably from about 0.1% to about 1.0%, by weight of the personal care composition.

The compositions of the present invention can contain a cationic polymer. Concentrations of the cationic polymer in the composition typically range from about 0.05% to about 3%, preferably from about 0.075% to about 2.0%, more preferably from about 0.1% to about 1.0%, by weight of the composition. Preferred cationic polymers will have cationic charge densities of at least about 0.9 meq/gm, preferably at least about 1.2 meq/gm, more preferably at least about 1.5 meq/gm, but also preferably less than about 7 meq/gm, more preferably less than about 5 meq/gin. The pH of intended use of the composition will generally range from about pH 3 to about pH 9, preferably between about pH 4 and about pH 8. The average molecular weight of such suitable cationic polymers will generally be between about 10,000 and 10 million, preferably between about 50,000 and about 5 million, more preferably between about 100,000 and about 3 million.

Suitable cationic polymers for use in the compositions of the present invention contain cationic nitrogen containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non limiting examples of cationic polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquatemium-16); copolymers of 1-vinyl-2-pyrrolidone and dimethylaminoethyl methacrylate (referred to in the industry by CTFA as Polyquatemium-11); cationic diallyl quaternary ammonium containing polymers, including, for example, dimethyldiallylammonium chloride homopolymer, copolymers of acrylamide and dimethyldiallylammonium chloride (referred to in the industry by CTFA as Polyquatemium 6 and Polyquaternium 7, respectively); amphoteric copolymers of acrylic acid including copolymers of acrylic acid and dimethyldiallylammonium chloride (referred to in the industry by CTFA as Polyquatemium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47).

Other suitable cationic polymers for use in the composition include polysaccharide polymers, such as cationic cellulose derivatives and cationic starch derivatives. Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquatemium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Polyalkylene glycols having a molecular weight of more than about 1000 are useful herein. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

The composition of the present invention can include dispersed particles. The compositions of the present invention, can include at least 0.025% by weight of the dispersed particles, more preferably at least 0.05%, still more preferably at least 0.1%, even more preferably at least 0.25%, and yet more preferably at least 0.5% by weight of the dispersed particles. In the compositions of the present invention, it is preferable to incorporate no more than about 20% by weight of the dispersed particles, more preferably no more than about 10%, still more preferably no more than 5%, even more preferably no more than 3%, and yet more preferably no more than 2% by weight of the dispersed particles.

Conditioning agents include any material which is used to give a particular conditioning benefit to hair and/or skin. The conditioning agents useful in the compositions of the present invention typically comprise a water insoluble, water dispersible, non-volatile, liquid that forms emulsified, liquid particles or are solubilized by the surfactant micelles, in the anionic detersive surfactant component (described above). Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

The conditioning agent of the compositions of the present invention can be an insoluble silicone conditioning agent. The silicone conditioning agent particles may comprise volatile silicone, non-volatile silicone, or combinations thereof. Preferred are non-volatile silicone conditioning agents. If volatile silicones are present, they will typically be incidental to their use as a solvent or carrier for commercially available forms of non-volatile silicone material ingredients, such as silicone gums and resins. The silicone conditioning agent particles can comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, by weight of the composition, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, more preferably from about 100,000 to about 1,500,000 csk.

The dispersed silicone conditioning agent particles typically have a volume average particle diameter ranging from about 0.01 m to about 50 μm. For small particle application to hair, the volume average particle diameters typically range from about 0.01 μm to about 41 μm, preferably from about 0.01 μm to about 2 μm, more preferably from about 0.01 μm to about 0.51 μm. For larger particle application to hair, the volume average particle diameters typically range from about 5 μm to about 125 μm, preferably from about 10 μm to about 90 μm, more preferably from about 15 μm to about 70 μm, more preferably from about 20 μm to about 50 μm.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties can also be used.

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methylvinylsiloxane) copolymer, polydimethylsiloxane) (diphenyl siloxane)(methylvinylsiloxane) copolymer and mixtures thereof.

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984).

Silicone resins can be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit (CH3)3SiO05; D denotes the difunctional unit (CH3)2SiO; T denotes the trifunctional unit (CH3)SiO15; and Q denotes the quadra- or tetra-functional unit Si02. Primes of the unit symbols (e.g. M', D', T, and Q') denote substituents other than methyl, and must be specifically defined for each occurrence.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The conditioning component of the compositions of the present invention can also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones (described above).

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about C to about C19. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene are preferred. A preferred hydrocarbon polymer is polybutene, such as the copolymer of isobutylene and butene. A commercially available material of this type is L-14 polybutene from Amoco Chemical Corporation.

Organic conditioning oils for use in the compositions of the present invention can also include liquid polyolefins, more preferably liquid poly-a-olefins, more preferably hydrogenated liquid poly-a-olefins. Polyolefins for use herein are prepared by polymerization of C4 to about C14 olefenic monomers, preferably from about C6 to about C12.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin containing refinery feedstocks or effluents. Preferred hydrogenated a-olefin monomers include, but are not limited to: 1-hexene to 1-hexadecenes, 1-octene to 1-tetradecene, and mixtures thereof.

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof can include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of C4 to C8 dicarboxylic acids (e.g. C1 to C22 esters, preferably C1 to C6, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as C10 to C22 carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters.

Specific non-limiting examples of suitable synthetic fatty esters for use in the compositions of the present invention include: P-43 (C8-C10 triester of trimethylolpropane), MCP-684 (tetraester of 3,3 diethanol-1,5 pentadiol), MCP 121 (C8-C10 diester of adipic acid), all of which are available from Mobil Chemical Company.

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal).

The compositions of the present invention can contain a humectant. The humectants herein are selected from the group consisting of polyhydric alcohols, water soluble alkoxylated nonionic polymers, and mixtures thereof. The humectants, when used herein, are preferably used at levels by weight of the composition of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

The compositions of the present invention can further comprise a suspending agent at concentrations effective for suspending water-insoluble material in dispersed form in the compositions or for modifying the viscosity of the composition. Such concentrations range from about 0.1% to about 10%, preferably from about 0.3% to about 5.0%, by weight of the compositions.

Suitable suspending agents include crystalline suspending agents that can be categorized as acyl derivatives, long chain amine oxides, or combinations thereof. These suspending agents are described in U.S. Pat. No. 4,741,855.

The compositions of the present invention can contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

The compositions of the present invention can also contain pigment materials such as nitroso, monoazo, diazo, carotenoid, triphenyl methanes, triaryl methanes, xanthenes, quinolines, oxazines, azines, anthraquinones, indigoids, thionindigoids, quinacridones, phthalocyianines, botanicals, and natural colors including water soluble dye components. The compositions of the present invention can also contain chelating agents.

Personal care compositions are well known in the art. See for example, U.S. Pat. No. 6,274,150; No. 6,599,513; No. 6,0969,169; No. 4,735,742; No. 6,451,300; No. 4,942,161; No. 5,456,851; No. 5,854,246; No. 6,099,870; No. 7,094,422; No. 7,732,450; No. 6,663,875; No. 6,812,238; No. 7,732,450; No. 5,654,293; No. 6,099,870; No. 6,375,939; No. 6,451,300; No. 6,616,941; No. 6,649,155; No. 6,974,569; No. 6,491,902; No. 6,524,594; No. 6,419,913, No. 6,284,234; No. 6,908,889; No. 6,495,498; and No. 6,514,490, U.S. Pat. App. Pub No. US2010/0183539; No. US2009/0317502 No. US2006/0269501; No. US2003/0003070; No. US2008/0107749; No. US2008/0200539; No. US2003/0206958; No. US2002/0176894; US2006/0110415; No. US2010/0104646; No. US2010/0040697; No. US2010/0215775; No. US2009/0214628; No. US2007/0110700; and No. US20080152611, and Int. Pat. Pub. No. WO2001051014; No. WO2001066551; No. WO2002090354; No. WO2003006009; No. WO2000043390; No. WO2001032652; No. WO2001066551; No. WO2002090354; No. WO2003008391; No. WO2004028502; No. WO2004018485; No. WO2005006860; No. WO2010138674; No. WO2003086271; No.

WO2002067880; No. WO2010/051918; No. WO2006109642; No. WO2009006212; No. WO2007021789; No. WO2008006712; No. WO2010149424; No. WO2010127924; No. WO2009071408; No. WO2009053431; No. WO2008006712; No. WO2008003677; No. WO2004035015; and No. WO2002067880, content of all of which is incorporated herein by reference. The above mentioned compositions can be formulated with a conjugated prodrug of the invention. For example, the active ingredient of the above-mentioned compositions can be replaced with a conjugated prodrug of the invention.

In some embodiments, the personal care composition is a hair care composition. A hair care composition can be used to or prevent dandruff. Hair care compositions are herein defined as compositions for the treatment of hair including, but not limited to, shampoos, conditioners, rinses, lotions, aerosols, gels, mousses, and hair dyes. The hair care compositions of the present invention comprise an effective amount of at least one conjugate-based prodrug (e.g., conjugate-based antifungal prodrug), ranging from about 0.001% to about 10%, preferably from about 0.1% to about 5%, and more preferably from about 0.5% to about 3% by weight relative to the total weight of the composition. As used here, the term "effective amount" is that amount of the conjugate-based antifungal prodrug in the hair care composition necessary to achieve the desired improvement.

In addition to the conjugate-based prodrug, the hair care composition can comprise a cosmetically acceptable medium for hair care compositions, examples of which are described for example in U.S. Pat. No. 6,280,747; No. 6,139,851; and No. 6,013,250, all of which are incorporated herein by reference. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hair care compositions can contain one or more conventional cosmetic or dermatological additives or adjuvants including, but not limited to, antioxidants, preserving agents, fillers, surfactants, UVA and/or UVB sunscreens, fragrances, viscosifying agents, wetting agents, anionic polymers, nonionic polymers, amphoteric polymers, viscosity/foam stabilizers, opacifying/pearlizing agents, sequestering agents, stabilizing agents, hair conditioning agents, humectants, anti-static agents, antifreezing agents, buffering agents, dyes, and pigments. These adjuvants are well known in the field of cosmetics and are described in many publications, for example see *Harry's Book of Cosmeticology*, 8th edition, Martin Rieger, ed., Chemical Publishing, New York (2000).

The conjugate-based antifungal prodrug can be used in a shampoo. Suitable shampoo compositions are well known in the art. For example, components of shampoo compositions are described by Wells et al. in U.S. Pat. No. 6,930,078, by Patel et al. in U.S. Pat. No. 5,747,436 and by Niemiec et al. in U.S. Pat. No. 6,908,889. The hair shampoo composition can be an aqueous solution, aqueous-alcoholic solution or an oil-in-water (O/W) or water in oil in water (W/O/W) emulsion. The shampoo composition of the invention contains an effective amount of conjugate-based antifungal prodrug from about 0.001% to about 10%, preferably from about 0.1% to about 5%, and more preferably from about 0.5% to about 3% by weight relative to the total weight of the composition. The balance of the shampoo composition is comprised of the fluid vehicle, surfactant, and other additives. Typically, the fluid vehicle comprises water and other solvents which can include, without limitation, mineral oils and fatty alcohols.

Surfactants are the primary components in shampoo compositions. The amount of primary surfactant is generally in the range of between about 10% and 20% as based on the final weight of the composition, more typically from about 8 to about 18%. A secondary surfactant can also be present, generally in the range of about 0 to about 6%. The surfactants in the shampoo composition according to the invention may include one or more, or a combination thereof of anionic, nonionic, amphoteric or cationic surfactants. Examples of anionic surfactants include, but are not limited to, soaps, alkyl and alkyl ether sulfates, and alpha-olefin sulfonates. The preferred anionic surfactants are lauryl (ammonium, sodium, triethanolamine and diethanolamine and laureth (sodium and ammonium)) sulfates. Secondary anionic surfactants include, but are not limited to, sulfosuccinates, linear alkylbenzene sulfonates, N-acyl methyltaurates, N-acyl sarcosinates, acyl isothionates, N-acyl polypeptide condensates, polyalkoxylated ether glycolates, monoglyceride sulfates, fatty glycerol ether sulfonates. Examples of nonionic surfactants include, but are not limited to, fatty alkanolamides, amine oxides, polymeric ethers, polysorbate 20, PEG-80 sorbitan, and nonoxynols. Examples of amphoteric surfactants include, but are not limited to, betaines, alkyl-substituted amino acids (sodium lauraminopropionate and sodium lauriminopropionate).

The shampoo composition according to the invention can also comprise viscosity and foam stabilizers, the amount of, generally in the range of about 1.5 to about 5% based on the final weight of the composition. Specific examples of viscosity/foam stabilizers include, but are not limited to, alkanolamides (such as Cocamide MEA).

Additionally, the shampoo composition can contain minor proportions of one or more conventional cosmetic or dermatological additives or adjuvants, provided that they do not interfere with the mildness, performance or aesthetic characteristics desired in the final products. The total concentration of added ingredients usually is less than 5%, preferably less than 3%, by weight of the total composition. Such minor components include but are not limited to, opacifying/pearlizing agents, such as stearic acid derivatives (e.g., ethylene glycol monostearate or ethylene glycol distearate); solvents; sequestering agents, such as disodium ethylene diaminetetraacetic acid (EDTA) and its salts, citric acid, or polyphosphates; stabilizing agents; viscosifying agents, such as salts (e.g, sodium chloride or ammonium chloride) for anionic formulations; PEG-120 methyl glucose dioleate and PEG-150 pentaerythrityl tetrastearate for anionic/nonionic formulations; hair conditioning agents, such as the cationic polymers polyquaternium 10 (Ucare Polymers), cationic guar (Jacquar C-261N), polyquaternium-7 (Merquat Polymers) and silicones such as dimethicone and aminodimethicone; humectants; anti-static agents; antifreezing agents, buffering agents; antioxidants, such as BHT, BHA and tocopherol; UV absorbers, such as benzophenone; preservatives, such as parabens; fragrances; and dyes or pigments. These adjuvants are well known in the field of cosmetics and are described in many publications, for example see *Harry's Book of Cosmeticology*, supra.

The final essential component in the shampoo composition is water, which provides an aqueous medium that constitutes the balance of the shampoo composition. Generally, the proportion of water ranges from about 53% to about 95%, preferably, 68% to about 92%, and most preferably about 80% to about 87%, by weight of the resultant shampoo composition.

The shampoo compositions of the present invention can be prepared using conventional formulation and mixing techniques. Where melting or dissolution of solid surfactants or wax components is required these can be added to a premix of the surfactants, or some portion of the surfactants, mixed and heated to melt the solid components, e.g., about 50° C. to about 95° C. This mixture can then optionally be processed through a high shear mill and cooled, and then the remaining components mixed in. The compositions typically have a final viscosity of from about 2,000 to about 20,000 cps (centipoise). The viscosity of the composition may be adjusted by conventional techniques including addition of sodium chloride or ammonium xylenesulfonate as needed.

A hair care composition can also include one or more antidandruff agents. As used herein, the term "antidandruff agent" refers to any chemical that is effective in the treatment of dandruff and/or the symptoms associated therewith. Antidandruff agents are well known in the art. See for example, U.S. Pat. App. Pub. No. 2004/0202636 and No. 2003/0003070, and U.S. Pat. No. 6,284,234, content of all of which is incorporated herein by reference. Typically, the antidandruff agent is an antifungal agent effective against the fungus *Malassezia*. Suitable antidandruff agents include, but are not limited to pyridinethione salts, such as calcium, magnesium, barium, strontium, zinc, and zirconium pyridinethione salts; azoles, such as climbazole, ketoconazole, and itraconazole, piroctone olamine (octopirox); undecylenic acid, undecylenamidopropylbetaine (AMPHORAM U®), coal tar (NeutrogenaT/gel, CAS No. 8030-31-7; salicylic acid (Ionil T); selenium sulfide (Selsun Blue) and Tea tree, and mixtures thereof. One pyridinethione salt is the zinc salt of 1-hydroxy-2-pyridinethione (also known as zinc pyridinethione). These antifungal agents are generally available from commercial sources. For example, zinc pyridinethione is available from Olin Corporation (Norwalk, Conn.); octopirox is available from Hoechst AG (Frankfurt, Germany); AMPHORAM U® is available from CECA Arkema Group (France); and ketoconazole is available from Alfa Chem (Kings Point, N.Y.).

In some embodiments, the personal care composition is a skin care composition. A skin care composition can be used to or prevent acne. Skin care compositions are herein defined as compositions for the treatment of skin including, but not limited to, skin conditioners, moisturizers, foundations, anti-wrinkle products, skin cleansers, and body washes. The skin care compositions of the present invention include any composition that may be topically applied to the skin, including but not limited to, lotions, creams, gels, sticks, sprays, ointments, cleansing liquid washes, cleansing solid bars, pastes, foams, powders, shaving creams, and wipes.

The skin care compositions of the invention may comprise several types of cosmetically-acceptable topical carriers including, but not limited to solutions, colloidal suspensions, dispersions, emulsions (microemulsions, nanoemulsions, multiple and non-aqueous emulsions), hydrogels, and vesicles (liposomes, niosomes, novasomes). Components and formulation methods of suitable cosmetically-acceptable topical carriers are well known in the art and are described, for example, in U.S. Pat. No. 6,797,697 and U.S. Pat. App. Pub. No. 2005/0142094 and No. 2005/0008604, Int. Pat. App. Pub. No. 2006/029818 and No. 2000/062743, content of all of which is incorporated herein by reference. Those skilled in the art will appreciate the various methods for producing these various product forms.

The skin care compositions of the present invention comprise an effective amount of at least one conjugate-based prodrug (e.g. conjugate-based antibacterial prodrug), ranging from about 0.001% to about 10%, preferably from about 0.1% to about 5%, and more preferably from about 0.5% to about 3% by weight relative to the total weight of the composition. As used here, the term "effective amount" is that amount of the conjugate-based prodrug in the skin care composition necessary to achieve the desired improvement.

Typically, the cosmetically acceptable medium for skin care compositions comprises water and other solvents which include, but are not limited to, mineral oils and fatty alcohols. The cosmetically-acceptable medium is from about 10% to about 99.99% by weight of the composition, preferably from about 50% to about 99% by weight of the composition, and can, in the absence of other additives, form the balance of the composition.

As used herein the term "cosmetically acceptable medium" refers to formulations that are used to treat skin, hair and/or nails and contain one or more ingredients used by those skilled in the art to formulate products used to treat skin, hair and/or nails. The cosmetically acceptable medium may be in any suitable form, i.e., a liquid, cream, emulsion, gel, thickening lotion or powder and will typically contain water, and may contain a cosmetically acceptable solvent and/or one or more surfactants.

The skin care composition can further comprise the following basic cosmetic raw materials, including, but not limited to hydrocarbons, esters, fatty alcohols, fatty acids, emulsifying agents, humectants, viscosity modifiers, and silicone-based materials. The compositions of the present invention can contain a wide range of these basic components. The total concentration of added ingredients usually is less than 50%, preferably less than 20%, and most preferably less than 10% by weight of the total composition. Those skilled in the art will appreciate the various concentrations and combinations for employing these basic components to achieve the desired product form.

Suitable hydrocarbons which can be used in the compositions of the invention include, but are not limited to mineral oil, isohexadecane, squalane, hydrogenated polyisobutene, petrolatum, paraffin, microcrystalline wax, and polyethylene.

Suitable esters which can be used in the compositions of the invention include, but are not limited to isopropyl palmitate, octyl stearate, caprylic/capric triglyceride, plant waxes (Canelilla, Caranauba), vegetable oils (natural glycerides) and plant oils (Jojoba).

Suitable fatty alcohols which may be used in the compositions of the invention include, but are not limited to myristyl, cety, stearyl, isostearyl, and behenyl.

Suitable emulsifying agents which can be used in the compositions of the invention include, but are not limited to anionic (TEA/K stearate (triethanolamine/potassium stearate), sodium lauryl stearate, sodium cetearyl sulfate, and beeswax/Borax), nonionic (glycerol di-stearate, PEG (polyethyleneglycol)-100 Stearate, Polysorbate 20, steareth 2 and steareth 20), and cationic (distearyldimethylammonium chloride, behenalkonium chloride and steapyrium chloride), polymeric (acrylates/C 10-30 alkyl acrylate crosspolymer, polyacrylamide, polyquaternium-37, propylene glycol, dicaprylate/dicaparate and PPG-1 Trideceth-6), and silicone based materials (alkyl modified dimethicone copolyols), and polyglyceryl esters, and ethoxylated di-fatty esters.

Exemplary humectants for use in the compositions of the invention include, but are not limited to propylene glycol, sorbitol, butylene glycol, hexylene glycol, acetamide MEA (acetylethanolamine), honey, and sodium PCA (sodium-2-pyrrolidone carboxylate).

Viscosity modifiers, which may be used in the compositions of the invention include, but are not limited to xanthum gum, magnesium aluminum silicate, cellulose gum, and hydrogenated castor oil.

Further, the skin care compositions can comprise one or more conventional functional cosmetic or dermatological additives or adjuvants, providing that they do not interfere with the mildness, performance or aesthetic characteristics desired in the final products. The CTFA (The Cosmetic, Toiletry, and Fragrance Association; now known as the Personal Care Products Council) *International Cosmetic Ingredient Dictionary and Handbook*, Eleventh Edition (2006), and *McCutcheon's Functional Materials*, North America and Internationals Editions, MC Publishing Co. (2007) describe a wide variety of cosmetic and pharmaceutical ingredients commonly used in skin care compositions, which are suitable for use in the compositions of the present invention. The compositions of the present invention can contain a wide range of these additional, optional components. The total concentration of added ingredients usually is less than about 20%, preferably less than about 5%, and most preferably less than about 3% by weight of the total composition. Such components include, but are not limited to surfactants, emollients, moisturizers, stabilizers, film-forming substances, fragrances, colorants, chelating agents, preservatives, antioxidants, pH adjusting agents, antimicrobial agents, water-proofing agents, dry feel modifiers, vitamins, plant extracts, hydroxy acids (such as alpha-hydroxy acids and beta-hydroxy acids), and sunless tanning agents. Examples of common raw materials and suitable adjuvants for an acne treatment composition are described by Beumer et al. supra and Robinson et al., supra.

Method of Treatment

The invention also provides a method for treating or preventing a fungal or bacterial infection in a subject. The method comprising administering to a subject in need thereof a composition described herein. Without limitations, fungal or bacterial infection can be selected from the group consisting of oral/vaginal candidiasis, ringworm (tinea infections of the body, scalp, beard, jock itch, athlete's foot), nail infections, ear infections. Further, the subject can be a human or non-human animal (e.g., for veterinary use), i.e.

As used herein, the term "administer" refers to the placement of a composition described herein, into a subject by a method or route which results in at least partial localization of the composition at a desired site. A composition described herein can be administered by any appropriate route which results in effective treatment in the subject, i.e. administration results in delivery to a desired location in the subject where at least a portion of the composition delivered. Exemplary modes of administration include, but are not limited to, injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. Without limitations, administration can be local or systemic.

In some embodiments, administration is topical, e.g., the composition is applied topically to the desired site.

The invention also provides a method for treating or preventing dandruff comprising applying a hair care composition comprising at least one conjugate-based antifungal prodrug, as described herein, to the scalp of a subject. The hair care composition can be rinsed from the scalp or left on the scalp, depending upon the type of composition used. The compositions described herein can be applied to the scalp by various means, including, but not limited to spraying, brushing, and applying by hand.

In another aspect, a method is provided for treating or preventing acne, the method comprising applying a skin care composition described herein to the skin of subject in need thereof. After application, the skin care composition can be rinsed from the skin or left on the skin, depending upon the type of composition used. The skin care composition can be applied to the skin by various means, including, but not limited to spraying, brushing, and applying by hand.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used to treat domesticated animals and/or pets.

In some embodiments, the subject is a human.

In some other embodiments, the subject is a non-human animal.

A subject can be one who has been previously diagnosed with or identified as suffering from or having a disorder characterized by a fungus or bacterial infection.

In some embodiments, the subject needs treatment for dandruff and/or acne.

In some embodiments, the subject is need of treatment for oral or vaginal candidiasis, ringworm (tinea infections of the body, scalp, beard, jock itch, athlete's foot), nail infections, or ear infections.

A subject can be one who is currently being treated for dandruff, acne, oral or vaginal candidiasis, ringworm (tinea infections of the body, scalp, beard, jock itch, athletes foot), nail infection, or ear infection.

In some embodiments of the aspects described herein, the method further comprising diagnosing a subject for a fungus infection before onset of treatment with a method described herein.

In some embodiments of the aspects described herein, the method further comprising diagnosing a subject for dandruff, acne, oral or vaginal candidiasis, ringworm (tinea infections of the body, scalp, beard, jock itch, athlete's foot), nail infection, or ear infection before onset of treatment with a method described herein.

In some embodiments, the subject is an animal, i.e., the compositions and methods described herein for veterinary use.

Prodrug

Without wishing to be bound by a theory, the conjugate-based prodrugs described herein are antifungal or antibacterial prodrugs. As used herein, a "prodrug" refers to compounds that can be converted via some chemical or physiological process (e.g., enzymatic processes and metabolic hydrolysis) to an active compound. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11, :345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.,* 72(3): 324-325 (1983); Freeman S, et al., "Bioreversible Protection for the Phospho Group: Chemical Stability and Bioactivation of Di(4-acetoxy-benzyl)Methylphosphonate with Carboxyesterase," *Chem. Soc., Chem. Commun.,* 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(S): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.,* 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

Nanoparticulates Comprising Active Agent and a Lipid

One of the major limitations of the available topical antifungal and antibacterial formulations is the residual time of the drug on the application surface, which is very short. For example, in case of anti-dandruff shampoo application on the scalp and hair, the active drug gets washed away from the scalp immediately after hair wash. This way, the drug does not get enough time to elicit its response as antifungal effect. Therefore, there is an unmet need to design a formulation, which can allow the drug to stay on the scalp for a longer time so that it can show its effect on the fungi. In order to serve this purpose, provided herein is a nanoparticulated system of appropriate size range which enhances nanoparticle retention on application area. In case of dandruff, while the NPs would be expected to get entrapped in the microcracks and intra-hair follicular spaces of the scalp and stay for a longer time, the nature of the NP will allow a controlled release of the drug. Further, the lipid dependence of lipophilic fungi and bacteria can be exploited to develop nanoparticulated system comprising suitable lipid source (e.g., fatty acid(s); tri-, di-, or mono-glyceride(s); or other lipids) that act food for the microbe. The nanoparticulated system, thus, enhances uptake of the intact NPs or the released drug utilizing a 'Trojan Horse Strategy'.

Accordingly, in another aspect, provided herein is a nanoparticle comprising: (i) a first component selected from antifungal agents, antibacterial agents, or a combination thereof; and (ii) a second component select from a lipid, a polymer or a combination thereof. It is to be understood that the discussion and embodiments of nanoparticles discussed above also apply to this aspect.

The first and second component can be present in any amount in the nanoparticle. For example, the first and the second components can be present independently in an amount from about 0.01 wt % to about 99 wt % based on the total weight of the nanoparticle. In some embodiments, the first or second component is present in an amount from about 0.01 wt % to about 99 wt % from about 0.01 wt % to about 90 wt %, from about 0.01 wt % to about 80 wt %, from about 0.01 wt % to about 70 wt %, from about 0.01 wt % to about 60 wt %, from about 0.01 wt % to about 50 wt %, from about 0.01 wt % to about 40 wt %, from about 0.01 wt % to about 30 wt %, from about 0.01 wt % to about 25 wt %, from about 0.1 wt % to about 80 wt %, from about 0.1 wt % to about 70 wt %, from about 0.1 wt % to about 60 wt %, from about 0.1 wt % to about 50 wt %, from about 0.1 wt % to about 40 wt %, from about 0.1 wt % to about 30 wt %, from about 0.0 wt % to about 25 wt % based on the total weight of the nanoparticle.

In some embodiments, the first or second component is present in an amount from with a lower limit of about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 50, 60, 70, 80 or 85 wt % and an upper limit of about 22, 3, 4, 5, 6, 7, 8, 9, 10, 11, 12, 13, 14, 15, 16, 17, 18, 19, 20, 21, 22, 23, 24, 25, 26, 27, 28, 29, 30, 30, 50, 60, 70, 80, 85 or 90 wt % based on the total weight of the nanoparticle.

In some embodiment, the first and second component can be covalently linked to each other. When the first and second components are covalently linked together, they can be in the form of a conjugated prodrug as discussed above. Alternatively, the first component and the second component are not covalently linked to each other.

A nanoparticle comprising the first and second components can be selected from the group consisting of liposomes, polymeric nanoparticles, nanoemulsions, self-microemulsifying drug delivery systems (SMEDDS), solid-lipid nanoparticles (SLNs), nano-structured liquid crystals, albumin based nanoparticles, dendrimers, carbon nanotubes, nano-structured lipid carriers (NLCs), polymersomes, nanocrystals, nanoemulsion, and the like.

In some embodiments, a nanoparticle comprising the first and second components can further comprise a surfactant. Exemplary surfactans are described above.

In some embodiments, a nanoparticle comprising the first and second components can further comprise an excipient. Again exemplary molecules which can be used as excipients are described above.

In some embodiments, the second component is a lipid. The lipid can be selected from the group consisting of fatty acids, fatty alcohols, glycerolipids (e.g., monoglycerides, diglycerides, and triglycerides), phospholipids, glycerophospholipids, sphingolipids, sterol lipids, prenol lipids, saccharolipids, polyketides, and any combination thereof.

In some embodiments, the lipid can be selected from the group consisting of glyceryl tripalmitate (Tripalm), Ceteth-10, egg lecithin, soy lecithin, glyceryl monocaprylate (Capmul MCM C8 EP), Capmul MCM C10, Glycerol Tricaprylate/Caprate (CAPTEX® 355 EP/NF), glycerol distearate (type I) EP (Precirol ATO 5), Lauric acid, Tridecylic acid, Myristic acid, Pentadecylic acid, Palmitic acid, Margaric acid, Stearic acid, Nonadecylic acid, Arachidic acid, Heneicosylic acid, Behenic acid, Tricosylic acid, Lignoceric acid, Pentacosylic acid, Cerotic acid, Heptacosylic acid, Montanic acid, Nonacosylic acid, Melissic acid, Henatriacontylic acid, Lacceroic acid, Psyllic acid, Geddic acid, Ceroplastic acid, Hexatriacontylic acid, α-Linolenic, Stearidonic, Eicosapentaenoic, Docosahexaenoic, Linoleic, γ-Linolenic, Dihomo-γ-linolenic, Arachidonic, Oleic, Elaidic, Eicosenoic, Erucic, Nervonic, Mead, Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid, Caprylic acid, Pelargonic acid, Capric acid, Undecylic acid, Lauric acid, Tridecylic acid, Myristic acid, Pentadecylic acid, Palmitic acid, Heptadecanoic acid, Stearic acid, Nonadecylic acid, Arachidic acid, Heneicosylic acid, Behenic acid, Tricosylic acid, Lignoceric acid, Pentacosylic acid, Cerotic acid, Heptacosylic acid, Montanic acid, Myristoleic acid, Palmitoleic acid, Sapienic acid, Oleic acid, Elaidic acid, Vaccenic acid, Linoleic acid, Linoelaidic acid, α-Linolenic acid, γ-Linolenic acid, Arachidonic acid, Eicosapentaenoic acid, Erucic acid, Docosahexaenoic acid, cis-11-octadecenoic acid, cis-11-eicosenoic acid, undecylenic acid, cis-β-docosenoic acid, neoheptanoic acid, neononanoic acid, neodecanoic acid, isostearic acid, 10-undecenoic acid, Phosphatidic acid (phosphatidate, PA), Phosphatidylethanolamine (cephalin,PE), Phosphatidylcholine (lecithin,PC), Phosphatidylserine (PS), Phosphatidylinositol (PI), Phosphatidylinositol phosphate (PIP), Phosphatidylinositol bisphosphate (PIP2), Phosphatidylinositol triphosphate (PIP3), Ceramide phosphorylcholine (Sphingomyelin, SPH), Ceramide phosphorylethanolamine (Sphingomyelin,Cer-PE), Ceramide phosphorylglycerol, Cholestanes, Cholanes, Pregnanes, Androstanes, Estranes, cholesterol, capryl alcohol, 2-ethyl hexanol, pelargonic alcohol, capric alcohol, Undecyl alcohol, Lauryl alcohol, Tridecyl alcohol, Myristyl alcohol, Pentadecyl alcohol, cetyl alcohol, palmitoleyl alcohol, Heptadecyl alcohol, stearyl alcohol, isostearyl alcohol, elaidyl alcohol, oleyl alcohol, linoleyl alcohol, elaidolinoleyl alcohol, linolenyl alcohol, elaidolinolenyl alcohol, ricinoleyl alcohol, Nonadecyl alcohol, arachidyl alcohol, Heneicosyl alcohol, behenyl alcohol, erucyl alcohol, lignoceryl alcohol, ceryl alcohol, 1-heptacosanol, montanyl alcohol, cluytyl alcohol, 1-nonacosanol, myricyl alcohol, melissyl alcohol, 1-dotriacontanol, geddyl alcohol, Cetearyl alcohol, Propylene Glycol Dicaprate, 1,3-Propanediol Dicaprylate, Caprylic/Capric Acid Ester of Saturated Fatty Alcohol C12-C18, Propylene Glycol Dicaprylocaprate, Propylene Glycol Dicaprylocaprate, 1,3-Propanediol Dicaprylate/Dicaprate, Glyceryl Tricaprylate/Tricaprate, Caprylic/Capric Triglyceride, Glyceryl Tricaprylate/Caprate/Laurate, Glyceryl Tricaprylate/Tricaprate, Caprylic/Capric Triglyceride, Glycerol Tricaprylate/Caprate, Glyceryl Triacetate, Glyceryl Tricaprylate, Triolein, and any combinations thereof.

Figure 32:
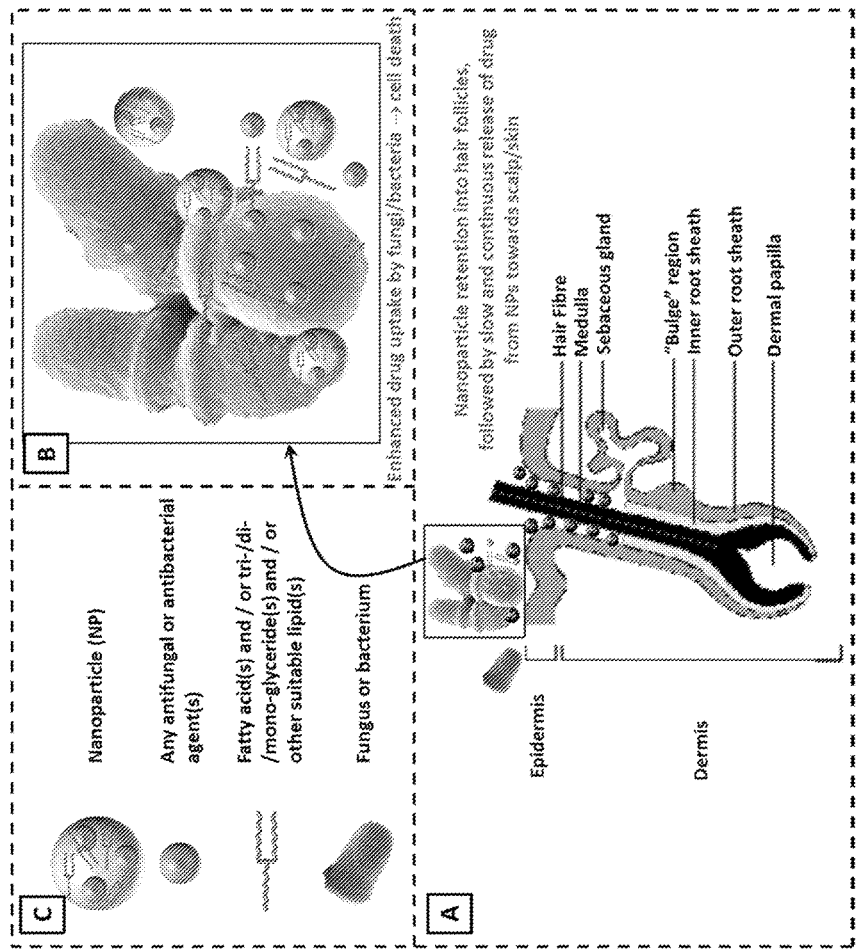

The nanoparticulated system described herein provides a novel mechanism for enhanced uptake of intact NPs and/or released drug by lipophilic fungi and lipophilic bacteria. These nanoparticulate systems are useful for the treatment of fungal and bacterial infections in human and other mammals. The present invention provides NPs represented by the general pictorial representation (FIG. 32).

The nanoparticulated system disclosed here can be formulated as polymeric NPs, liposomes, albumin based NPs, dendrimers, carbon nanotubes, solid lipid NPs (SLNs), nano-structured lipid carriers (NLCs), self-microemulsifying drug delivery systems (SMEDDS), polymersomes, nanocrystals, nanoemulsion, etc. These nanoparticles can be prepared using methods commonly used by one of skill in the art for preparing the different types of nanoparticles.

After manufacturing, the NP dispersions can be either subjected to high speed centrifugation to sediment NPs or concentrated using centrifugal filtration devices, dialysis membrane, tangential (cross) flow filtration system. The concentrated dispersions can be lyophilized using cryoprotectant(s) to get free flowing NPs. The NP dispersion or lyophilized powder can be characterized using Scanning Electron Microscopy (SEM) and/or Transmission Electron Microscopy (TEM) and/or Atomic Force Microscopy (AFM) imaging and others. Further, the NPs can finally be formulated in any of the dosage forms depending on medical use against a particular clinical indication.

The invention can be further described by one or more of the following numbered paragraphs.

1. A conjugate-based antifungal or antibacterial prodrug of formula:
   (i) $(AFA)_m$-X-$(L)_n$, wherein: AFA is an antifungal agent or an antibacterial agent; L is a carrier; X is a linker; m ranges from 1 to 10; and n ranges from 2 to 10;
   (ii) $[(AFA)_{m'}-X]_p$-L, wherein: AFA is an antifungal agent or an antibacterial agent; L is a carrier; X is a linker; m' is 1 to 10; and p is 1 to 10;
   (iii) AFA-$[X-(L)_{n'}]_{q'}$, wherein: AFA is an antifungal agent or an antibacterial agent; L is a carrier; X is a linker; n' is 1 to 10; and q is 1 to 10, provided that q' and n are not both 1; or
   (iv) $(AFA)_{m''}$-X, wherein: AFA is an antifungal agent or an antibacterial agent; X is a linker; and m" is 1 to 10.
2. The conjugate-based prodrug of paragraph 1, wherein m' and p are 1.
3. The conjugate-based prodrug of paragraph 1, wherein q is 1 and n' is 2.
4. The conjugate-based prodrug of paragraph 1, wherein m" is 2.
5. The conjugate-based prodrug of paragraph 1, wherein the conjugate-based prodrug is a nanoparticle.
6. The conjugate-based prodrug of paragraph 5, wherein the nanoparticle is of size 1 nm to 1000 nm.
7. The conjugate-based prodrug of any of paragraphs 1-6, wherein the prodrug is formulated in nanoparticle selected from the group consisting of liposomes, polymeric nanoparticles, nanoemulsions, self-microemulsifying drug delivery systems (SMEDDS), solid-lipid nanoparticles, nano-structured liquid crystals, and any combination thereof.
8. The conjugate-based prodrug of paragraph 7, wherein the nanoparticle is of size 20 nm-500 nm.
9. The conjugate-based prodrug of any of paragraphs 1-8, wherein the linker is linked to a ring-nitrogen of an azole moiety of the antifungal or the antibacterial agent or the linker is linked to a hydroxyl group of the antifungal or the antibacterial agent.
10. The conjugate-based prodrug of any of paragraphs 1-9, wherein the linker is a cleavable linker.
11. The conjugate-based prodrug of any of paragraphs 1-10, wherein the linker is cleaved by a esterase.
12. The conjugate-based prodrug of paragraph 11, wherein the esterase is a lipase.
13. The conjugate-based prodrug of any of paragraphs 1-12, wherein the linker is cleaved by a lipase from the fungus *Malassezia*.
14. The conjugate-based prodrug of paragraph 13, wherein the fungus is of genus *Malassezia* spp.
15. The conjugate-based prodrug of any of paragraphs 1-14, wherein the linker is selected from group consisting of:
   (i) —CH($R^1$)—, wherein $R^1$H or $C_1$-$C_6$alkyl, which can be optionally substituted and/or interspersed with one or more of heteroatoms, aryls, heteroaryls, cyclyls, and heterocyclyls;

(ii)

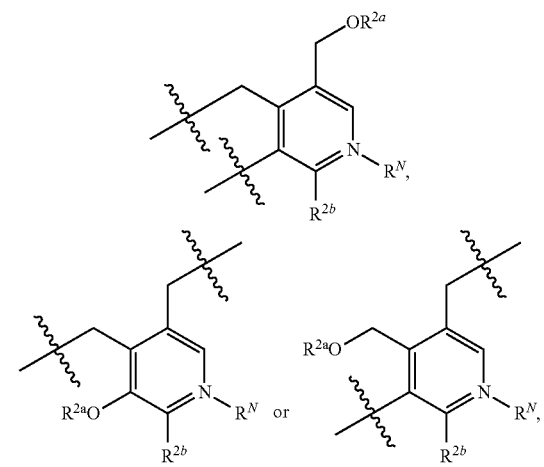

wherein $R^{2a}$ is a hydroxyl protecting group; $R^{2b}$ is $C_1$-$C_6$alkyl, which can be optionally substituted or interspersed with one or more heteroatoms, aryls, heteroaryls, cyclyls and heterocyclyls; and $R^N$ is absent, H, $C_1$-$C_6$alkyl, or acyl, each of which can be optionally substituted;

(iii) a polyethylene glycol of formula —$CH_2CH_2$[$OCH_2CH_2$]$_a$O$HC_2CH_2$—, wherein a is 1-50;

(iv) —$CH_2C(R^{3a}R^{3b})CH(OR^{3c})C(O)N(R^{3d})$—$(CH_2)_b$—, wherein $R^{3a}$ and $R^{3b}$ are independently H or $C_1$-$C_6$alkyl, which can be optionally substituted and/or interspersed with one or more heteroatoms, aryls, heteroaryls, cyclyls, and heterocyclyls; $R^{3c}$ is H or a carrier; $R^{3d}$ is H, alkyl, alkenyl, alkynyl, cyclyl, heterocyclyl, aryl, or heteroaryl, each of which can be optionally substituted; and b is 1-10;

(v)

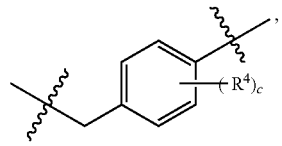

wherein $R^4$ is halo, CN, CF3, alkyl, alkenyl, cyclyl, heterocyclyl, aryl, heteroaryl, $NO_2$, $OR^6$, $OC(O)R^{4a}$, $OC(O)OR^{4a}$, $N(R^{4b})_2$, $NHC(O)R^{4a}$, $NHC(O)OR^{4a}$, $C(O)R^{4a}$, $C(O)OR^{4a}$, $SR^{4a}$, or $SO_2R^{4a}$, each of which can be optionally substituted; $R^{4a}$ is independently for each occurrence, H, alkyl, alkenyl, alkynyl, cyclyl, heterocyclyl, aryl, or heteroaryl, each of which can be optionally substituted; and c is 0 to 4;

(vi) —$CH_2CH(R^6)$—, wherein R is H or $C_1$-$C_6$ alkyl, which can be optionally substituted and/or interspersed with one or more heteroatoms, aryls, heteroaryls, cyclyls, and heterocyclyls;

(vii) —$CH(R^7)C(O)$—, wherein $R^7$ is H, $C_1$-$C_6$alkyl, aryl, heteroaryl, cyclyl, or heterocyclyl, each of which can be optionally substituted and/orinterspersed with one or more heteroatoms, aryls, heteroaryls, cyclyls and heterocyclyls;

(viii) —$CH(R^8)OC(O)$-L'-$C(O)O$—, wherein $R^8$ is H or $C_1$-$C_6$alkyl; and L' is an alkyl group, which can be optionally substituted and/or interspersed with one or more heteroatoms, aryls, heteroaryls, cyclyls or heterocylcyls, each of which can also be optionally substituted;

(ix) —CH(R⁹)OC(O)—, —CH(R⁹)OC(O)-L'-, —CH(R⁹)OC(O)-L'-Y— or —CH(R⁹)OC(O)-L'-Y—C(O)—, wherein R⁹ is H or $C_1$-$C_6$ alkyl; Y is O, S, or NH; and L' is an alkyl, which can be optionally substituted and/or interspersed one or more heteroatoms, aryls, heteroaryls, cyclyls or heterocylcyls, each of which can be optionally substituted;

(x) —CH(R¹⁰ᵃ)OC(O)-L'-C(O)OCH(R¹⁰ᵇ)—, wherein R¹⁰ᵃ and R¹⁰ᵇ are independently H or $C_1$-$C_6$ alkyl, which can be optionally substituted; and L' is $C_1$-$C_{20}$ alkyl, which can be optionally substituted and/or interspersed one or more heteroatoms, aryls, heteroaryls, cyclyls or heterocylcyls, each of which can be optionally substituted;

(xi) —C(O)-L'-C(O)—, —C(O)-L'-, —C(O)-L'-Y—, or —C(O)-L'-Y—C(O)—, wherein Y is O, S, or NH; and L' is an alkyl, which can be optionally substituted and/or interspersed one or more heteroatoms, aryls, heteroaryls, cyclyls or heterocylcyls, each of which can be optionally substituted;

(xii) —C(O)-L'-C(O)O—[CH₂CH₂O]ᵥ·—, wherein v' is 1-500 and L' is an alkyl, which can be optionally substituted and/or interspersed one or more heteroatoms, aryls, heteroaryls, cyclyls or heterocylcyls, each of which can be optionally substituted;

(xiii) PLGA;
(xiv) a direct bond;
(xv) a dicarboxylic acid;
(xvi) a beta-hydroxy acid;
(xvii) a polyhydroxy acid; and
(xviii) any combinations thereof.

16. The conjugate-based prodrug of any of paragraphs 1-15, wherein the antifungal agent comprises an azole moiety or a hydroxyl group.

17. The conjugate-based prodrug of any of paragraphs 1-16, wherein the antifungal agent is selected from the group consisting of Fluconazole, Isavuconazole, Itraconazole, Ketoconazole, Miconazole, Clortrimazole, Voriconazole, Posaconazole, Ravuconazole, natamycin, lucensomycin, nystatin, amphotericin B, echinocandins, Cancidas, pradimicins, beanomicins, nikkomycins, sordarins, allylamines, Triclosan, Piroctone, phenpropimorph, terbinafine, antifungal peptide, and derivatives and analogs thereof.

18. The conjugate-based prodrug of any of paragraphs 1-17, wherein the antibacterial agent is effective against *P. acne*.

19. The conjugate-based prodrug of any of paragraphs 1-15 or 18, wherein the antibacterial agent is selected from the group consisting of macrolides orketolides such as erythromycin, azithromycin, clarithromycin and telithromycin; beta-lactams including penicillin, cephalosporin, and carbapenems such as carbapenem, imipenem, and meropenem; monobactams such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, and astreonam; quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; antibacterial sulfonamides and antibacterial sulphanilamides, including para-aminobenzoic acid, sulfadiazine, sulfisoxazole, sulfamethoxazole and sulfathalidine; aminoglycosides such as streptomycin, neomycin, kanamycin, paromycin, gentamicin, tobramycin, amikacin, netilmicin, spectinomycin, sisomicin, dibekalin and isepamicin; tetracyclines such as tetracycline, chlortetracycline, demeclocycline, minocycline, oxytetracycline, methacycline, doxycycline; rifamycins such as rifampicin (also called rifampin), rifapentine, rifabutin, bezoxazinorifamycin and rifaximin; lincosamides such as lincomycin and clindamycin; glycopeptides such as vancomycin and teicoplanin; streptogramins such as quinupristin and daflopristin; oxazolidinones such as linezolid; polymyxin, colistin and colymycin; and trimethoprim and bacitracin.

20. The conjugate-based prodrug of any of paragraphs 1-19, wherein the carrier comprises a carboxylic or a hydroxyl group.

21. The conjugate-based prodrug of any of paragraphs 1-20, wherein the carrier is a polymer; a carboxylated polymer, a hydroxylated polymer, a polyethylene glycol; a carboxylated PEG, a fatty acid comprising a $C_6$-$C_{26}$ alkyl, which can be optionally substituted and/or interspersed with a heteroatom, aryl, heteroaryl, cyclyl, or heterocyclyl; an amino acid; a peptide; a nucleic acid; a glycerol, substituted glycerol, an antibacterial agent, an antifungal agent; a alpha-hydroxy acid, a beta-hydroxy acid, a dicarboxylic acid, oxadiacid, and any combinations thereof.

22. The conjugate-based prodrug of any of paragraphs 1-21, wherein the carrier is a fatty acid selected from the group consisting of Caprylic acid, Pelargonic acid, Capric acid, Undecylic acid, Lauric acid, Tridecylic acid, Myristic acid, Pentadecylic acid, Palmitic acid, Heptadecanoic acid, Stearic acid, Nonadecylic acid, Arachidic acid, Heneicosylic acid, Behenic acid, Tricosylic acid, Lignoceric acid, Pentacosylic acid, Cerotic acid, Heptacosylic acid, Montanic acid, Myristoleic acid, Palmitoleic acid, Sapienic acid, Oleic acid, Elaidic acid, Vaccenic acid, Linoleic acid, Linoelaidic acid, α-Linolenic acid, γ-Linolenic acid, Arachidonic acid, Eicosapentaenoic acid, Erucic acid, Docosahexaenoic acid, cis-11-octadecenoic acid, cis-11-eicosenoic acid, undecylenic acid, cis-β-docosenoic acid, neoheptanoic acid, neononanoic acid, neodecanoic acid, isostearic acid, 10-undecaenoic acid, adapalene.

23. The conjugate-based prodrug of any of paragraphs 1-21, wherein the carrier is polymer selected from the group consisting of PLGA, PLA, PEG, chitosan, pullulan, polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, polymethyl methacrylate, chitin, chitosan, copolymers of polylactic acid and polyglycolic acid, poly(glycerol sebacate) (PGS), and copolymers, terpolymers, gelatin, collagen, silk, chitosan, alginate, cellulose, poly-nucleic acids, cellulose acetates (including cellulose diacetate), polyethylene, polypropylene, polybutylene, polyethylene terphthalate (PET), polyvinyl chloride, polystyrene, polyamides, nylon, polycarbonates, polysulfides, polysulfones, hydrogels (e.g., acrylics), polyacrylonitrile, polyvinylacetate, cellulose acetate butyrate, nitrocellulose, copolymers of urethane/carbonate, copolymers of styrene/maleic acid, poly(ethylenimine), Pluronic (Poloxamers 407, 188), Hyaluron, heparin, agarose, Pullulan, ethylene/vinyl alcohol copolymers (EVOH), and copolymers including one or more of the foregoing.

24. The conjugate-based prodrug of any of paragraphs 1-21, wherein the carrier is selected from the group consisting of undecylenic acid; palmitic acid; oleaic acid, linoleic acid, lauric acid, lys-his-lys-his-lys-his hexapeptide; L- or D-tyrosine; L- or D-serine; L- or D-threonine; a peptide of 2-10 amino acids; chitosan, and pullulan.

25. The conjugate-based prodrug of any of paragraphs 1-24, wherein the conjugate is etoconazole methylene palmitate, ketoconazole 1-ethylene palmitate, ketoconazole methylene laurate, ketoconazole 1-ethylene laurate, ketoconazole methylene undecylenate, ketoconazole 1-ethylene undecylenate, ketoconazole methylene oleate, ketoconazole 1-ethylene oleate, ketoconazole methylene linolate, ketoconazole 1-ethylene linolate, ketoconazole-methylene-PLGA, ketoconazole-pyridoxine-undecylenic acid, ketoconazole-pamthenol dimer, ketoconazole-propylene glycol-hexapeptide, ketoconazole-lactic acid-chitosan, ketoconazole-methylene-oxaacid acid-chitosan, ketoconazole-methylene-oxadiacid dimer, ketoconazole-methylene-glutamic acid dimer, clindamycin lauric acid conjugate, clindamycin-glycolic acid-PLGA conjugate, clindamycin-succinic acid-PLGA conjugate, clindamycin-adapalene conjugate, erythromycin-lauric acid conjugate, erythromycin-lactic-lauric acid conjugate, lauric acid-PLGA-erythromycin conjugate, adapalene-triethyleneglycon-erythromycin conjugate, clindamycin dimer, clindamycin dimer with azelaic acid, clindamycin dimer with carboxylated PEG, clindamycin dimer with glutamic acid, clindamycin dimer with oxydiacetic acid, clindamycin triclosan conjugate, clindamycin-glutamic acid-triclosan conjugate, or clindamycin-oxydiacetic acid-triclosan conjugate 26. A nanoparticle comprising: (i) a first component selected from antifungal agents, antibacterial agents, or a combination thereof; and (ii) a second component select from a lipid, a polymer or a combination thereof 27. The nanoparticle of paragraph 26, wherein the first component is from about 0.01 wt % to about 99 wt % based on the total weight of the nanoparticle.

28. The nanoparticle of paragraph 26 or 27, wherein the lipid is from about 0.01 wt % to about 99 wt % based on the total weight of the nanoparticle.

29. The conjugate of any of paragraphs 26-28, wherein the first component and the second component are not covalently linked to each other.

30. The nanoparticle of any of paragraphs 26-29, wherein the nanoparticle is selected from the group consisting of liposomes, polymeric nanoparticles, nanoemulsions, self-microemulsifying drug delivery systems (SMEDDS), solid-lipid nanoparticles (SLNs), nano-structured liquid crystals, albumin based nanoparticles, dendrimers, carbon nanotubes, nano-structured lipid carriers (NLCs), polymersomes, nanocrystals, nanoemulsion, and the like.

31. The nanoparticle of any of paragraphs 26-30, wherein nanoparticle is of size about 1 nm to about 1000 nm.

32. The nanoparticle of any of paragraphs 26-31, wherein the nanoparticle is of size about 20 nm to about 500 nm.

33. The nanoparticle of any of paragraphs 26-32, wherein the nanoparticle comprises further comprises a surfactant.

34. The method of paragraph 33, wherein the surfactant is from about 0.01 wt % to about 30 wt % based on the total weight of the nanoparticle.

35. The nanoparticle of any of paragraphs 26-34, wherein the nanoparticle further comprises a carrier or excipient.

36. The nanoparticle of paragraph 35, wherein the excipient is from about 0.01 wt % to about 30 wt % based on the total weight of the nanoparticle.

37. The nanoparticle of any of paragraphs 26-36, wherein the lipid is selected from the group consisting of fatty acids, fatty alcohols, glycerolipids (e.g., monoglycerides, diglycerides, and triglycerides), phospholipids, glycerophospholipids, sphingolipids, sterol lipids, prenol lipids, saccharolipids, polyketides, and any combination thereof.

38. The nanoparticle of any of paragraphs 26-37, wherein the lipid is selected from the group consisting of glyceryl tripalmitate (Tripalm), Ceteth-10, egg lecithin, soy lecithin, glyceryl monocaprylate (Capmul MCM C8 EP), Capmul MCM C10, Glycerol Tricaprylate/Caprate (CAPTEX® 355 EP/NF), glycerol distearate (type I) EP (Precirol ATO 5), Lauric acid, Tridecylic acid, Myristic acid, Pentadecylic acid, Palmitic acid, Margaric acid, Stearic acid, Nonadecylic acid, Arachidic acid, Heneicosylic acid, Behenic acid, Tricosylic acid, Lignoceric acid, Pentacosylic acid, Cerotic acid, Heptacosylic acid, Montanic acid, Nonacosylic acid, Melissic acid, Henatriacontylic acid, Lacceroic acid, Psyllic acid, Geddic acid, Ceroplastic acid, Hexatriacontylic acid, α-Linolenic, Stearidonic, Eicosapentaenoic, Docosahexaenoic, Linoleic, γ-Linolenic, Dihomo-γ-linolenic, Arachidonic, Oleic, Elaidic, Eicosenoic, Erucic, Nervonic, Mead, Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid, Caprylic acid, Pelargonic acid, Capric acid, Undecylic acid, Laurie acid, Tridecylic acid, Myristic acid, Pentadecylic acid, Palmitic acid, Heptadecanoic acid, Stearic acid, Nonadecylic acid, Arachidic acid, Heneicosylic acid, Behenic acid, Tricosylic acid, Lignoceric acid, Pentacosylic acid, Cerotic acid, Heptacosylic acid, Montanic acid, Myristoleic acid, Palmitoleic acid, Sapienic acid, Oleic acid, Elaidic acid, Vaccenic acid, Linoleic acid, Linoelaidic acid, α-Linolenic acid, γ-Linolenic acid, Arachidonic acid, Eicosapentaenoic acid, Erucic acid, Docosahexaenoic acid, cis-11-octadecenoic acid, cis-11-eicosenoic acid, undecylenic acid, cis-β-docosenoic acid, neoheptanoic acid, neononanoic acid, neodecanoic acid, isostearic acid, 10-undecenoic acid, Phosphatidic acid (phosphatidate, PA), Phosphatidylethanolamine (cephalin, PE), Phosphatidylcholine (lecithin, PC), Phosphatidylserine (PS), Phosphatidylinositol (PI), Phosphatidylinositol phosphate (PIP), Phosphatidylinositol bisphosphate (PIP2), Phosphatidylinositol triphosphate (PIP3), Ceramide phosphorylcholine (Sphingomyelin, SPH), Ceramide phosphorylethanolamine (Sphingomyelin, Cer-PE), Ceramide phosphorylglycerol, Cholestanes, Cholanes, Pregnanes, Androstanes, Estranes, cholesterol, capryl alcohol, 2-ethyl hexanol, pelargonic alcohol, capric alcohol, Undecyl alcohol, Lauryl alcohol, Tridecyl alcohol, Myristyl alcohol, Pentadecyl alcohol, cetyl alcohol, palmitoleyl alcohol, Heptadecyl alcohol, stearyl alcohol, isostearyl alcohol, elaidyl alcohol, oleyl alcohol, linoleyl alcohol, elaidolinoleyl alcohol, linolenyl alcohol, elaidolinolenyl alcohol, ricinoleyl alcohol, Nonadecyl alcohol, arachidyl alcohol, Heneicosyl alcohol, behenyl alcohol, erucyl alcohol, lignoceryl alcohol, ceryl alcohol, 1-heptacosanol, montanyl alcohol, cluytyl alcohol, 1-nonacosanol, myricyl alcohol, melissyl alcohol, 1-dotriacontanol, geddyl alcohol, Cetearyl alcohol, Propylene Glycol Dicaprate, 1,3-Propanediol Dicaprylate, Caprylic/Capric Acid Ester of Saturated Fatty Alcohol C12-C18, Propylene Glycol Dicaprylocaprate, Propylene Glycol Dicaprylocaprate, 1,3-Propanediol Dicaprylate/Dicaprate, Glyceryl Tricaprylate/Tricaprate, Caprylic/Capric Triglyceride, Glyceryl Tricaprylate/Caprate/Laurate, Glyceryl Tricaprylate/Tricaprate, Caprylic/Capric Triglyceride, Glycerol Tricaprylate/Caprate, Glyceryl Triacetate, Glyceryl Tricaprylate, Triolein, and any combinations thereof.

39. The conjugate of any of paragraphs 26-38, wherein the antifungal agent is selected from the group consisting of zinc pyrithione, piroctone olamine, Abafungin, Albaconazole, Allicin, Amorolfin, Anidulafungin, Benzoic acid with a keratolytic agent, Butenafine, Butoconazole, Caspofungin, Ciclopirox (ciclopirox olamine), Citronella oil, Clotrimazole, Coconut oil, Crystal violet, Econazole, Fenticonazole, Fluconazole, Flucytosine or 5-fluorocytosine, Griseofulvin, Haloprogin, Iodine, Isavuconazole, Isoconazole, Itraconazole, Ketoconazole, lemon myrtle, Micafungin, Miconazole, Naftifine, Neem Seed Oil, Olive leaf extract, Omoconazole, Orange oil, Oxiconazole, palmarosa oil, patchouli, Polygodial, Posaconazole, Ravuconazole, Selenium, Sertaconazole, Sulconazole, Tea tree oil—ISO 4730 ("Oil of *Melaleuca*, Terpinen-4-ol type"), Terbinafine, Terconazole, Tioconazole, Tolnaftate, Undecylenic acid, Voriconazole, Zinc Selenium sulfide, Fluconazole, Isavuconazole, Itraconazole, Ketoconazole, Miconazole, Clortrimazole, Voriconazole, Posaconazole, Ravuconazole, natamycin, lucensomycin, nystatin, amphotericin B, echinocandins, Cancidas, pradimicins, beanomicins, nikkomycins, sordarins, allylamines, Triclosan, Piroctone, phenpropimorph, terbinafine, antifungal peptide, and derivatives and analogs thereof.

40. The conjugate of any of paragraphs 26-39, wherein the antibacterial agent is selected from the group consisting of macrolides orketolides such as erythromycin, azithromycin, clarithromycin and telithromycin; beta-lactams including penicillin, cephalosporin, and carbapenems such as carbapenem, imipenem, and meropenem; monobactams such as penicillin G, penicillin V, methicillin, oxacillin, cloxacillin, dicloxacillin, nafcillin, ampicillin, amoxicillin, carbenicillin, ticarcillin, meziocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, and astreonam; quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; antibacterial sulfonamides and antibacterial sulphanilamides, including para-aminobenzoic acid, sulfadiazine, sulfisoxazole, sulfamethoxazole and sulfathalidine; aminoglycosides such as streptomycin, neomycin, kanamycin, paromycin, gentamicin, tobramycin, amikacin, netilmicin, spectinomycin, sisomicin, dibekalin and isepamicin; tetracyclines such as tetracycline, chlortetracycline, demeclocycline, minocycline, oxytetracycline, methacycline, doxycycline, rifamycins such as rifampicin (also called rifampin), rifapentine, rifabutin, bezoxazinorifamycin and rifaximin; lincosamides such as lincomycin and clindamycin; glycopeptides such as vancomycin and teicoplanin; streptogramins such as quinupristin and dafloprustin; oxazolidinones such as linezolid; polymyxin, colistin and colymycin; and trimethoprim and bacitracin.

41. A personal care composition comprising an effective amount of a conjugate-based prodrug of any of paragraphs 1-25 or a nanoparticle of any of paragraphs 26-40.

42. The personal care composition of paragraph 41, wherein the composition further comprises a pharmaceutical or a topical agent.

43. The personal care composition of paragraph 42, wherein the pharmaceutical or the topical is selected from the group consisting of those that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotionsickness agents; antiinflammatory agents; antihyperkeratolytic agents; antiperspirants; antipsoriatic agents; antiseborrheic agents; hair conditioners and hair treatment agents; antiaging and antiwrinkle agents; sunblock and sunscreen agents; skin lightening agents; depigmenting agents; vitamins; corticosteroids; tanning agents; humectants; hormones; retinoids; gum disease or oral care agents; topical cardiovascular agents; corn, callus and wart removing agents; depilating agents; and any combinations thereof.

44. The personal care composition of paragraph 42 or 43, wherein the pharmaceutical or the topical agent is selected from the group consisting of azelaic acid, triclosan, alpha-hydroxy acids, glycolic acid, mandelic acid, beta-hydroxy acids, salicylic acid, polyhydroxy acids, lactobionic acid, galactose, gluconic acid, adapalene, abacavir, acebutolol, acetaminophen, acetaminosalol, acetazolamide, acetohydroxamic acid, acetylsalicylic acid, acitretin, aclovate, acrivastine, actiq, acyclovir, adapalene, adefovir dipivoxil, adenosine, albuterol, alfuzosin, allopurinol, alloxanthine, almotriptan, alprazolam, alprenolol, aluminum acetate, aluminum chloride, aluminum chlorohydroxide, aluminum hydroxide, amantadine, amiloride, aminacrine, aminobenzoic acid (PABA), aminocaproic acid, aminosalicylic acid, amiodarone, amitriptyline, amlodipine, amocarzine, amodiaquin, amorolfine, amoxapine, amphetamine, ampicillin, anagrelide, anastrozole, anthralin, apomorphine, aprepitant, arbutin, aripiprazole, ascorbic acid, ascorbyl palmitate, atazanavir, atenolol, atomoxetine, atropine, azathioprine, azelaic acid, azelastine, azithromycin, bacitracin, beclomethasone dipropionate, bemegride, benazepril, bendroflumethiazide, benzocaine, benzonatate, benzophenone, benztropine, bepridil, betamethasone dipropionate, betamethasone valerate, brimonidine, brompheniramine, bupivacaine, buprenorphine, bupropion, burimamide, butenafine, butoconazole, cabergoline, caffeic acid, caffeine, calcipotriene, camphor, candesartan cilexetil, capsaicin, carbamazepine, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clomiphene, clonidine, clopidogrel, clotrimazole, clozapine, cocaine, codeine, cromolyn, crotamiton, cyclizine, cyclobenzaprine, cycloserine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamnide, dopamine, dorzolamide, doxepin, doxorubicin, doxycycline, doxylamine, doxypin, duloxetine, dyclonine, econazole, eflormthine, eletriptan, emtricitabine, enalapril, ephedrine, epinephrine, epinine, epirubicin, eptifibatide, ergotarnine, erythromycin, escitalopram, esmolol, esomeprazole, estazolam, estradiol, ethacrynic acid, ethinyl estradiol, etidocaine, etomidate, famciclovir, famotidine, felodipine, fentanyl, ferulic acid, fexofenadine, flecainide, fluconazole, flucytosiine, fluocinolone acetonide, fluocinonide, 5-fluorouracil, fluoxetine, fluphenazine, flurazepam, fluvoxamine, formoterol, furosemide, galactarolactone, galactonic acid, galactonolactone, galantamine, gatifloxacin, gefitinib, gemcitabine, gemifloxacin, glycolic acid, griseofulvin, guaifenesin, guanethidine, N-guanylhistamine, haloperidol, haloprogin, hexylresorcinol, homatropine, homosalate, hydralazine, hydrochlorothiazide, hydrocortisone, hydrocortisone 21-acetate, hydrocortisone 17-butyrate, hydrocortisone 17-valerate, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loperamide, losartan, loxapine, lysergic diethylamide, mafenide, malic acid, maltobionic acid, mandelic acid, maprotiline, mebendazole, mecamylamine, meclizine, meclocycline, memantine, menthol, meperidine, mepivacaine, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, nicardipine, nicotine, nifedipine, nimodipine, nisoldipine, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate O, palonosetron, pantothenic acid, pantoyl lactone, paroxetine, pemoline, penciclovir, penicillamine, penicillins, pentazocine, pentobarbital, pentostatin, pentoxifylline, pergolide, perindopril, permethrin, phencyclidine, phenelzine, pheniramine, phenmetrazine, phenobarbital, phenol, phenoxybenzamine, phentolamine, phenylephrine, phenylpropanolamine, phenytoin, physostigmine, pilocarpine, pimozide, pindolol, pioglitazone, pipamazine, piperonyl butoxide, pirenzepine, podofilox, podophyllin, pratipexole, pramoxine, prazosin, prednisone, prenalterol, prilocaine, procainamide, procaine, procarbazine, promazine, promethazine, promethazine propionate, propafenone, propoxyphene, propranolol, propylthiouracil, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivasfigmine, rizatriptan, ropinirole, ropivacaine, salicylamide, salicylic acid, salmeterol, scopolamine, selegiline, selenium sulfide, serotonin, sertindole, sertraline, sibutramine, sildenafil, sotalol, streptomycin, strychnine, sulconazole, sulfabenz, sulfabenzamide, sulfabromomethazine, sulfacetamide, sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, tadalafil, tamsulosin, tartaric acid, tazarotene, tegaserol, telithromycin, telmisartan, temozolomide, tenofovir disoproxil, terazosin, terbinafine, terbutaline, terconazole, terfenadine, tetracaine, tetracycline, tetrahydrozoline, theobromine, theophylline, thiabendazole, thioridazine, thiothixene, thymol, tiagabine, timolol, tinidazole, tioconazole, tirofiban, tizanidine, tobramycin, tocainide, tolazoline, tolbutamide, tolnaftate, tolterodine, tramadol, tranylcypromine, trazodone, triamcinolone acetonide, triamcinolone diacetate, triamcinolone hexacetonide, triamterene, triazolam, triclosan, triflupromazine, trimethoprim, trimipramine, tripelennamine, triprolidine, tromethamine, tropic acid, tyramine, undecylenic acid, urea, urocanic acid, ursodiol, vardenafil, venlafaxine, verapamil, vitamin E acetate, voriconazole, warfarin, xanthine, zafirlukast, zaleplon, zinc pyrithione, ziprasidone, zolmitriptan, Zolpidem, and any combinations thereof.

45. The personal care composition of any of paragraphs 41-44, wherein the composition further comprises at least one cosmetic raw material or adjuvant selected from the group consisting of antioxidants, preserving agents, fillers, surfactants, UVA and/or UVB sunscreens, fragrances, viscosifying agents, wetting agents, anionic polymers, nonionic polymers, amphoteric polymers, viscosity/foam stabilizers, opacifying/pearlizing agents, sequestering agents, stabilizing agents, hair conditioning agents, humectants, anti-static agents, anti-freezing agents, buffering agents, dyes, pigments, hydrocarbons, esters, fatty alcohols, fatty acids, emulsifying agents, viscosity modifiers, silicone based materials, surfactants, emollients, moisturizers, stabilizers, film-forming substances, fragrances, colorants, chelating agents, preservatives, antioxidants, pH adjusting agents, water-proofing agents, dry feel modifiers, vitamins, plant extracts, hydroxy acids, organic sunscreen agents, inorganic sunscreen agents, peptide-based inorganic sunscreen agents, and sunless tanning agents.

46. The personal care composition of any of paragraphs 41-45, wherein the personal care composition is a hair care composition selected from the group consisting of a shampoo, a conditioner, a rinse, a lotion, an aerosol, a gel, a mousse, and a hair dye.

47. A method for treating or preventing dandruff, the method comprising the step of applying a composition of any of paragraph 41-46 to the scalp of a subject in need thereof.

48. The personal care composition of any of paragraphs 41-45, wherein the personal care composition is a skin care composition selected from the group consisting of lotions, creams, gels, sticks, sprays, ointments, cleansing liquid washes, cleansing solid bars, pastes, foams, powders, shaving creams, and wipes.
49. A method for treating or preventing acne in a subject, the method comprising the step of applying a composition of any of paragraph 41-46 or 48 to the skin of a subject in need thereof.
50. A method of treating or preventing a fungal or bacterial infection in a subject, the method comprising administering to a composition of any of paragraphs 1-25 or 26-40.
51. The method of paragraph 50, wherein said administering is topical or systemic.
52. The method of paragraph 50 or 51, wherein the fungal or bacterial infection is selected from the group consisting of oral/vaginal candidiasis, ring worm (e.g., tinea infections of the body, scalp, beard,jock itch, athlete's foot), nail infections, ear infections, and any combinations thereof.
53. The method of any of paragraphs 50-52, wherein the subject is a mammal.
54. The method of any of paragraphs 50-53, wherein the subject is a human.
55. The method of any of paragraphs 50-53, wherein the subject is non-human mammal.
56. Use of a composition of any of paragraphs 1-25 or 26-40 for treatment or prevention of a fungal or bacterial infection in a subject.
57. The use of paragraph 56, wherein the composition is applied topically or administered systemically.
58. The use of paragraph 56 or 57, wherein the fungal or bacterial infection is selected from the group consisting of oral/vaginal candidiasis, ring worm (e.g., tinea infections of the body, scalp, beard,jock itch, athlete's foot), nail infections, ear infections, and any combinations thereof.
59. The use of any of paragraphs 56-58, wherein the subject is a mammal.
60. The use of any of paragraphs 56-59, wherein the subject is a human.
61. The use of any of paragraphs 56-59, wherein the subject is non-human mammal.

Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a staticatly significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

By "treatment", "prevention" or "amelioration" is meant delaying or preventing the onset of a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least 5%, at least 10%, at least 20%, at least 30%, at least 40%, or at least 50%.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "halogen" refers to any radical of fluorine, chlorine, bromine or iodine.

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions.

The term "alkyl" refers to saturated or non-saturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkoxy" refers to an —O-alkyl radical.

The term "aminoalkyl" refers to an alkyl substituted with an amino.

The term "mercapto" refers to an —SH radical.

The term "thioalkoxy" refers to an —S-alkyl radical.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "arylalkyl" refers to alkyl substituted with an aryl.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The teen "heteroarylalkyl" refers to an alkyl substituted with a heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "haloalkyl" refers to an alkyl group having one, two, three or more halogen atoms attached thereto. Exemplary haloalkyl groups include, but are not limited to chloromethyl, bromoethyl, trifluoromethyl, and the like.

The term "optionally substituted" means that the specified group or moiety, such as an alkyl group, alkenyl group, alkynyl group, cyclyl group, heterocyclyl group, aryl group, heteroaryl group and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, or heteroaryl group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

In many cases, protecting groups are used during preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative protecting groups are disclosed in Greene and Wuts, *Protective Groups in Organic Synthesis*, Chapter 2, 2d ed., John Wiley & Sons, New York, 199. Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Exemplary amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R and S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction $F_{(+)}$ and $F_{(−)}$ (where the sum of $F_{(+)}$ and $F_{(−)}=1$). The enantiomeric excess is defined as $*F_{(+)}-F_{(−)}*$ and the percent enantiomeric excess by $100\times *F_{(+)}-F_{(−)}*$. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non optically active starting material, substrate, or intimidate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereo preferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A nonselective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

As used herein, the term "pharmaceutically-acceptable salts" refers to the conventional nontoxic salts or quaternary ammonium salts of a compound, e.g., from non-toxic organic or inorganic acids. These salts can be prepared in situ in the administration vehicle or the dosage form manufacturing process, or by separately reacting a purified compound in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1: Synthesis of Ketoconazole-Methylene-Fatty Acid Ester Conjugates

Ketoconazole-methylene-fatty acid conjugates (3a-3h) were synthesized as shown in scheme 1.

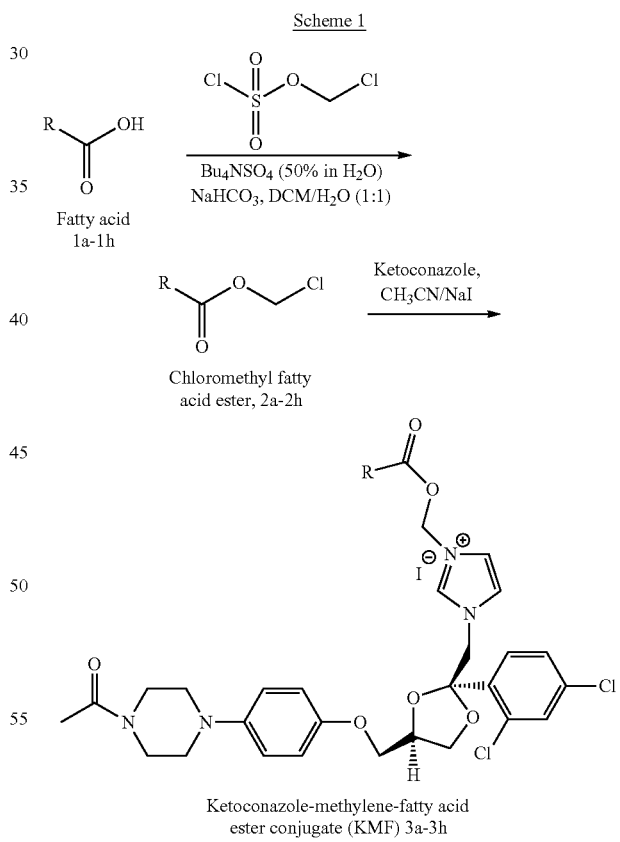

1a = Lauric acid
1b = Palmitic acid
1c = Stearic acid
1d = 10-Undecylenic acid
1e = Oleic acid
1f = Linoleic acid
1g = Caprylic acid
1h = mPEG-Succinic acid

Ketoconazole-Methylene-Palmitate Conjugate (3b)

Step-1 Synthesis of Chloromethyl Palmitate (2b)

Palmitic acid (0.3 g, 1.17 mmol) was dissolved in 5 ml dichloromethane (DCM) followed by addition of sodium bicarbonate (0.4 g, 4.68 mmol), 5 ml water and tetrabutylammonium sulfate (0.135 ml, 0.117 mmol). The resultant solution was stirred vigorously at 0° C. After 10 min, chloromethyl chlorosulfate (0.14 ml, 1.4 mmol) in DCM was added into the reaction mixture and the resultant solution was allowed to stir vigorously until room temperature was achieved. The organic layer was extracted with DCM, washed with brine and finally dried over sodium sulfate to obtain pure chloromethyl palmitate (0.3 g, 85% yield).

Step-2: Synthesis of Ketoconazole-methylene-palmitate Conjugate (3b)

Ketoconazole (0.26 g, 0.49 mmol), chloromethyl palmitate (0.3 g, 0.98 mmol), sodium iodide (0.147 g, 0.98 mmol), were suspended in acetonitrile and the resultant solution was refluxed for 4 hr under argon atmosphere. The reaction mixture was filtered, concentrated and the residue was triturated with diethyl ether to obtain a crude product. The crude product was purified by silica (60-120 mesh) column chromatography eluting with 4-5% MeOH/DCM to give yellow colored solid compound (0.3 gm, 65% yield). $^1$H-NMR (500 MHz, CDCl$_3$): $\delta_H$ 0.885 (t, 3H), 1.24-1.25 (bs, 24H), 1.668-1.73 (m, 2H), 2.157 (s, 3H), 2.28-2.31 (t, 2H), 3.07-3.14 (dd, 4H), 3.667-3.71 (d, 3H), 3.74-3.75 (d, 2H), 3.72 (m, 1H), 3.81-4.11 (m, 2H), 4.12-4.413 (m, 1H), 4.856 (s, 2H), 6.0-6.117 (dd, 2H), 6.84 (d, J=9 Hz, 2H), 6.93 (d, J=9 Hz, 2H), 7.31-7.36 (m, 2H), 7.48 (s, 2H), 7.7-7.72 (d, J=8.5 Hz, 1H), 9.9 (s, 1H). ESI-MS, m/z observed 799.5 (M), calculated 799.4 (M).

Similarly, other methylene fatty acid ester conjugates were also synthesized from ketoconazole using a similar procedure as described above for 3b. Mass spectrometry data for some of the Ketoconazole-methylene-fatty acid conjugates synthesized are shown in Table 1.

TABLE 1

| Compound name | Mass Calculated | Mass Observed |
|---|---|---|
| Ketoconazole-methylene-laureate, 3a | 743.33 | 743.58 (M) |
| Ketoconazole-methylene-10-undecylenate, 3d | 727.3 | 727.4 (M), 462.2 (M/2) |
| Ketoconazole-methylene-oleate, 3e | 825.41 | 825.7 (M), 412.2 (M/2) |
| Ketoconazole-methylene-linoleate, 3f | 823.39 | 823.71 (M) |
| Ketoconazole-methylene-caprylate, 3g | 687.27 | 687.2, 343.83 (M/2), 366.29 (M/2 + 23) |

Example 2: Synthesis of Ketoconazole-1-ethylene-fatty acid ester Conjugates

Ketoconazole-1-ethylene-fatty acid ester conjugates (6a-6g) were synthesized as shown in Scheme 2.

Scheme 2

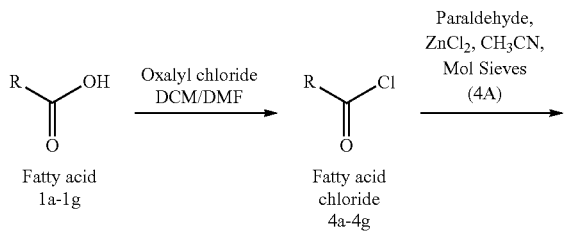

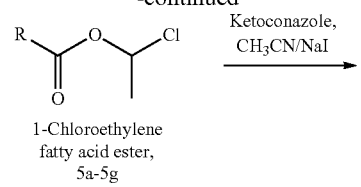

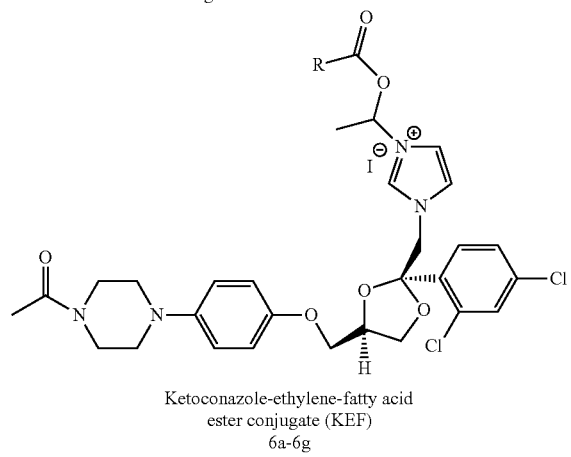

1a = Lauric acid
1b = Palmitic acid
1c = Myristic acid
1d = 10-Undecylenic acid
1e = Oleic acid
1f = Linoleic acid
1g = Caprylic acid

Ketoconazole-1-ethylene-palmitate Conjugate (6b)

Step 1: Synthesis of Palmitoyl Chloride (4b)

To a stirred solution of palmitic acid (0.2 g, 0.78 mmol) in 6-7 ml DCM, one drop of dimethylformamide (DMF) followed by oxalyl chloride (0.087 ml, 1.014 mmol) was added. The reaction mixture was stirred at room temperature for 3 hrs. The solvent was removed in vacuo and the resulting product (85-90% isolated yield) used in the next step without further purification.

Step 2: Synthesis of 1-Chloroethyl Palmitate (5b)

Palmitoyl chloride (2.0 ml, 6.6 mmol) was dissolved in minimum amount of acetonitrile and paraldehyde (0.3 ml, 2.2 mmol), zinc chloride (anhy) (0.027 g, 0.199 mmol) along with 4 Å molecular sieves were added to the resultant reaction mixture. The reaction mixture was heated at 60-65° C. for 2 hr and allowed to cool to room temperature. The resultant mixture was diluted with dichloromethane and filtered through celite. The filtrate was concentrated and the residue was purified by flash silica column chromatography (60-120 mesh). The required semisolid white product (0.84 gm, 40% yield) was obtained while eluting with 1-2% EtOAC/Hexane.

Step 3: Synthesis of Ketoconazole-1-ethylene-palmitate Conjugate (6b)

Ketoconazole (0.1 g, 0.19 mmol), 1-chloroethyl palmitate (0.121 g, 0.38 mmol), sodium iodide (NaI, 0.057 g, 0.38 mmol), were suspended in 10 ml acetonitrile and the resultant solution was refluxed for 4 hr under argon atmosphere. The reaction mixture was cooled, filtered and concentrated to obtain the crude residue. The residue was triturated with diethyl ether and was purified by flash silica (60-120 mesh) column chromatography, eluting with 4-6% MeOH/DCM to give yellow colored solid compound (0.1 g, 60% yield). $^1$H-NMR (500 MHz, CDCl$_3$): $\delta_H$ 0.894 (t, 3H), 1.24-1.3 (bs, 24H), 1.67 (m, 2H), 1.89-192 (m, 3H), 2.16 (s, 3H), 2.27-2.31 (m, 2H), 3.03-3.1 (dd, 4H), 3.62-3.65 (m, 2H), 3.77-3.808 (m, 4H), 3.81-3.942 (m, 2H), 4.3-4.45 (m, 1H), 4.94-5.07 (m, 2H), 6.84 (d, J=9 Hz, 2H), 6.93 (d, J=9 Hz, 2H), 7.31-7.36 (m, 2H), 7.48 (s, 2H), 7.7-7.72 (d, J=8.5 Hz, 1H), 9.9 (s, 1H). ESI-MS, m/z observed 813.73 (M), 407.3 (M/2), 428.18 (M/2+23), calculated 813.41 (M).

Similarly, other ethylene fatty acid ester conjugates were also synthesized from ketoconazole using a similar procedure as described above for 6b. Mass spectrometry data for some of the Ketoconazole-ethylene-fatty acid conjugates synthesized are shown in Table 2.

TABLE 2

| Compound name | Mass Observed | Mass Calculated |
| --- | --- | --- |
| Ketoconazole-1-ethylene-laurate, 6a | 757.35 | 757.58 |
| Ketoconazole-1-ethylene-myristate, 6c | 785.38 | 785.35 |
| Ketoconazole-1-ethylene-10-undecylenate, 6d | 741.32 | 741.45, 371.55 (M/2), 391.69 (M/2 + 23) |
| Ketoconazole-1-ethylene-oleate, 6e | 839.43 | 839.7, 419.31 (M/2), 440.59 (M/2 + 23) |
| Ketoconazole-1-ethylene-linoleate, 6f | 837.41 | 837.24 |
| Ketoconazole-1-ethylene-caprylate, 6g | 701.3 | 701.26 |

Example 3: Synthesis of Ketoconazole-N-hexadecyl-acetamide Conjugate (8)

Ketoconazole-N-hexadecyl-acetamide conjugate (8) was as shown in Scheme 3. It was considered as a negative control compound for comparison to methylene and ethylene fatty acid ester prodrug conjugates. The biological efficacy of this compound, 8 was compared with respect to the other prodrug ester and carbonate conjugates.

Scheme 3

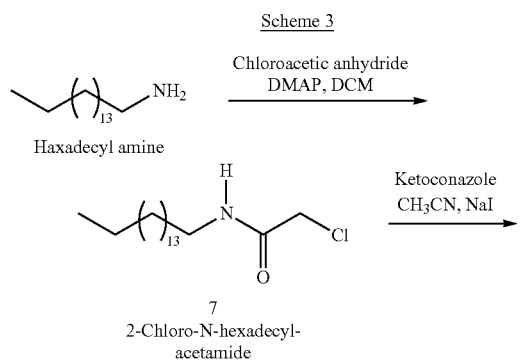

2-Chloro-N-hexadecyl-acetamide

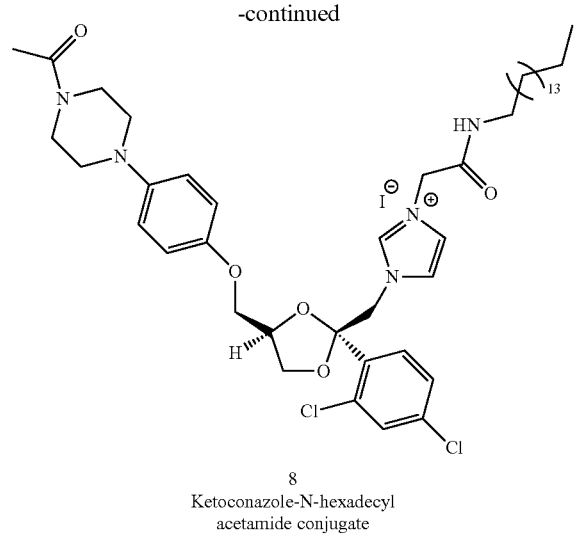

8
Ketoconazole-N-hexadecyl acetamide conjugate

Step-1: Synthesis of 2-Chloro-N-hexadecyl-acetamide (7)

To a stirred solution of hexadecyl amine (0.4 g, 1.65 mmol) in 10 ml DCM, 4-Dimethylaminopyridine (DMAP, 0.243 g, 1.98 mmol) was added. The solution was cooled at −15° C. and DCM solution of chloroacetic anhydride (0.24 g, 1.98 mmol) was added dropwise into the reaction mixture by maintaining the temperature at −15° C. The resultant solution was allowed to reach room temperature after stirring for 5-6 hr. The reaction mixture was diluted with ethylacetate, washed with water, 1N HCl and finally with brine. The combined organic layer was dried over sodium sulfate and evaporated to get the crude brown solid. The obtained solid is almost pure and directly used for the next step without further purification.

Step-2: Synthesis of Ketoconazole-N-hexadecyl-acetamide Conjugate (8)

Ketoconazole (0.15 g, 0.28 mmol), 2-Chloro-N-hexadecyl-acetamide (0.3 g, 0.946 mmol), sodium iodide (0.142 g, 0.946 mmol), were suspended in 10 ml acetonitrile and the resultant solution was refluxed for 4 hr under argon atmosphere. The reaction mixture was filtered, concentrated and the residue was triturated with diethyl ether to obtain a crude product. The crude product was purified by silica column chromatography eluting with 4-6% MeOH/DCM to give yellow colored solid compound (0.17 g, 65% yield). $^1$H-NMR (500 MHz, CDCl$_3$): $\delta_H$ 0.87 (t, 3H), 1.23-1.25 (bs, 26H), 1.44-1.46 (m, 2H), 2.16 (s, 3H), 3.08 (q, 2H), 3.21-

3.36 (m, 4H), 3.67-4.07 (m, 8H), 4.39-4.43 (m, 1H), 4.81 (s, 2H), 5.98 (s, 2H), 6.84 (d, J=9 Hz, 2H), 6.93 (d, J=9 Hz, 2H), 7.31-7.36 (m, 2H), 7.48 (s, 2H), 7.7-7.72 (d, J=8.5 Hz, 1H), 9.9 (s, 1H). ESI-MS, m/z observed 812.54 (M), 406.84 (M/2), 427.17 (M/2+23), calculated 812.43 (M).

Example 4: Synthesis of Ketoconazole-1-ethylene-fatty acid Carbonate Conjugates Ketoconazole-1-ethylene-fatty acid carbonate conjugates (11a-e) were synthesized as shown in scheme 4.

Scheme 4

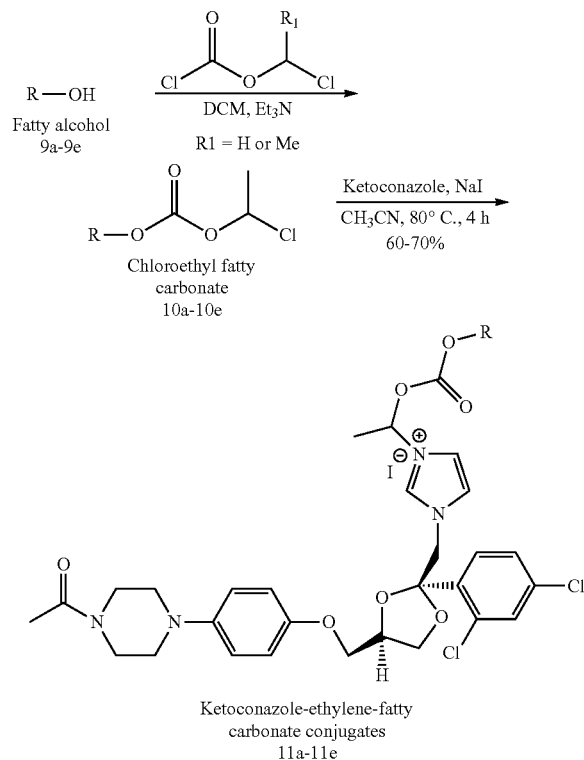

1a = Undecanol
1b = Lauryl alcohol
1c = Myristyl alcihol
1c = Cetyl alcohol
1d = Oleyl alcohol
1e = mPEG

Synthesis of Ketoconazole-1-ethylene-lauryl Carbonate Conjugate (11b)

Step-1: Synthesis of 1-Chloroethyl-laurylcarbonate (10b)

Lauryl alcohol (1 g, 5.36 mmol) was dissolved in 6 ml DCM and triethylamine (1.2 ml, 8.58 mmol) was added into it. The resultant solution was allowed to cool at −15° C. and chloroethylchloroformate (0.75 ml, 6.97 mmol) in DCM was added slowly into the reaction mixture. The resultant solution was stirred until it reached room temperature. At the end of 8 hr, the reaction mixture was diluted with DCM, washed with water and brine solution and finally dried over sodium sulfate. The crude liquid was directly used for the next step for quaternization with ketoconazole.

Step-2: Synthesis of Ketoconazole-1-ethylene-laurylcarbonate (11b)

Ketoconazole (0.7 g, 1.32 mmol), 1-Chloroethyl-laurylcarbonate (1.1 g, 3.95 mmol) and sodium iodide (0.6 g, 3.95 mmol) were suspended in 15 ml acetonitrile and the resultant solution was refluxed for 4 hr under argon atmosphere. The reaction mixture was filtered, concentrated and the residue was triturated with diethyl ether to obtain a crude product. The crude product was purified by silica column (60-120 mesh) chromatography eluting with 4-5% MeOH/DCM to give yellow colored solid compound (0.72 g, 60% yield). $^1$H-NMR (500 MHz, CDCl$_3$): $\delta_H$ 0.9 (t, 3H), 1.27 (bs, 16H), 1.61-1.63 (m, 2H), 1.92-196 (dd, 3H), 2.18 (s, 3H), 3.17-3.23 (m, 4H), 3.82-4.20 (m, 11H), 4.4-4.43 (m, 1H), 4.89-5.06 (m, 2H), 6.84 (d, J=9 Hz, 2H), 6.93 (d, J=9 Hz, 2H), 7.31-7.36 (m, 2H), 7.48 (s, 2H), 7.7-7.72 (d, J=8.5 Hz, 1H), 9.9 (s, 1H). ESI-MS, m/z observed 787.58 (M), calculated 787.36 (M).

Similarly, other fatty acid carbonate conjugates were also synthesized from ketoconazole using a similar procedure as described above for 11b. Mass spectrometry data for some of the Ketoconazole-carbonate-fatty acid conjugates synthesized are shown in Table 3.

TABLE 3

| Compound name | Mass Observed | Mass Calculated |
|---|---|---|
| Ketoconazole-1-ethylene-hexadecylcarbonate conjugate, 11c | 843.42 | 843.73 (M), 674.22 (Fragmented). |
| Ketoconazole-1-ethylene-oleylcarbonate conjugate, 11d | 869.44 | 869.5 (M), 434.8 (M/2). |

Example 5: Synthesis of Ketoconazole-1-ethylene-DEG/TEG/PEG-Fatty Acid Carbonate Conjugates 18a-d, 19a-d, and 20a-d Ketoconazole-1-ethylene-DEG/TEG/PEG-fatty acid carbonate conjugates 18a-d, 19a-d, and 20a-d were synthesized as shown in Scheme 5.

Scheme 5

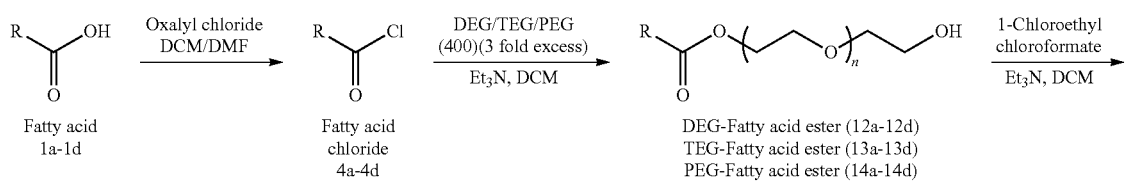

Fatty acid
1a-1d

Fatty acid chloride
4a-4d

DEG-Fatty acid ester (12a-12d)
TEG-Fatty acid ester (13a-13d)
PEG-Fatty acid ester (14a-14d)

-continued

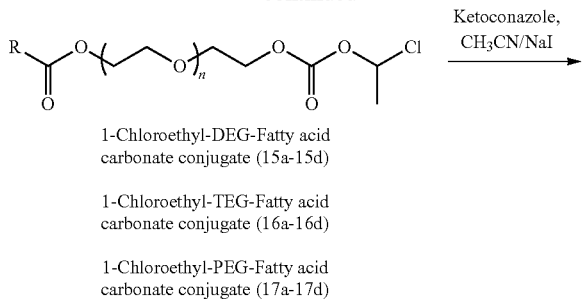

1-Chloroethyl-DEG-Fatty acid carbonate conjugate (15a-15d)

1-Chloroethyl-TEG-Fatty acid carbonate conjugate (16a-16d)

1-Chloroethyl-PEG-Fatty acid carbonate conjugate (17a-17d)

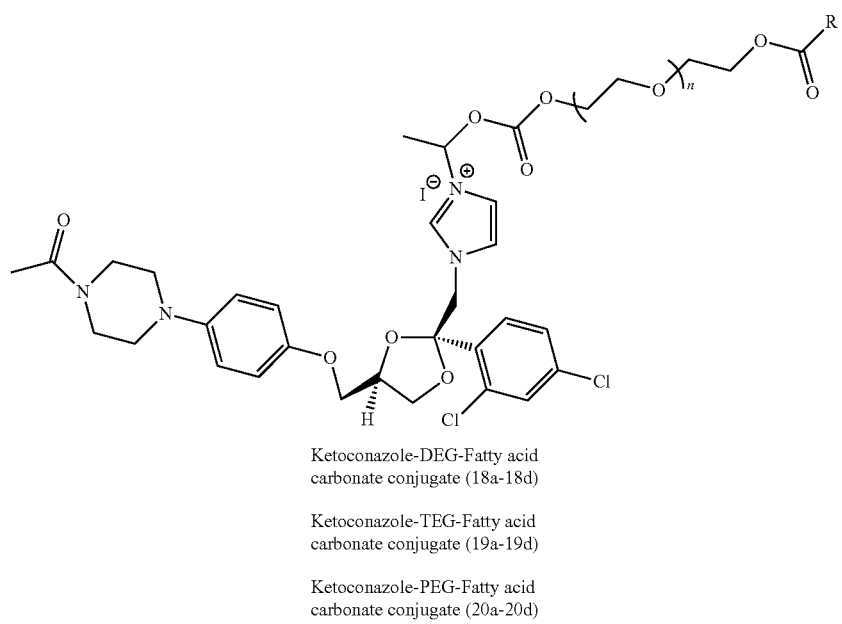

Ketoconazole-DEG-Fatty acid carbonate conjugate (18a-18d)

Ketoconazole-TEG-Fatty acid carbonate conjugate (19a-19d)

Ketoconazole-PEG-Fatty acid carbonate conjugate (20a-20d)

1a = Caprylic acid
1b = Lauric acid
1c = Palmitic acid
1d = Oleic acid

Synthesis of Ketoconazole-lauryltriethyleneglyceryl-carbonate Conjugate (19b)

Step-1: Synthesis of Lauryl Chloride (4b)

To a stirred solution of Lauric acid (1 g, 5.0 mmol) in 10 ml dichloromethane, one drop of dimethylformamide followed by oxalyl chloride (0.556 ml, 6.48 mmol) was added. The reaction mixture was allowed to stir at room temperature for 3 hrs. The solvent was removed in vacuo and the resulting product, 0.98 g (85-90% yield) used in the next step without further purification.

Step-2: Synthesis of Triethyleneglyceryl-laurate (13b)

Triethylene glycol (TEG, 1.65 ml, 12.36 mmol) was dissolved in 10 ml DCM and triethylamine (0.7 ml, 4.94 mmol) was added into it. Lauric acid chloride (0.9 g, 4.12 mmol) was dissolved in minimum DCM and added slowly into the reaction mixture. The resultant solution was allowed to stir at room temperature for overnight under argon atmosphere. The reaction mixture was diluted with DCM and washed successively with water (2×10 ml), 0.5N HCl (10 ml×2) and finally dried over sodium sulfate to obtain crude pure solid product (0.9 g, 70% yield) which was directly used for chloroethylation reaction. $^1$H-NMR (500 MHz, CDCl$_3$): $\delta_H$ 0.874 (t, 3H), 1.25 (bs, 16H), 1.59-1.64 (m, 2H), 2.31-2.35 (m, 2H), 2.96-2.98 (m, 1H), 3.62-3.77 (m, 10H), 4.23 and 4.31-4.32 (bs, 2H). ESI-MS, m/z observed 332.5 (M), calculated 332.2 (M).

Step-3: Synthesis of 1-Chloroethyl-lauryltriethyleneglyceryl-carbonate (16b)

To a stirred solution of 1-chloroethylchloroformate (0.2 ml, 1.95 mmol) in 6 ml DCM, the mixture of Triethyleneglyceryl-laurate (0.5 g, 1.5 mmol) and triethylamine (0.3 ml, 2.1 mmol) in 10 ml DCM was added dropwise by maintaining the temperature at −15° C. The reaction was stirred until room temperature was reached. The reaction mixture was diluted with DCM, washed successively with water, 0.5N HCl, brine solution and finally dried over sodium sulfate. The crude oily product (0.46 g, 70%) was directly used for the next step for quaternization with ketoconazole.

Step-4: Synthesis of Ketoconazole-lauryltriethyleneglyceryl-carbonate Conjugate (19b)

Ketoconazole (0.454 g, 0.85 mmol), 1-Chloroethyl-lauryltriethyleneglyceryl-carbonate (1.12 g, 2.55 mmol) and sodium iodide (0.39 g, 2.6 mmol), were suspended in 15 ml acetonitrile and the resultant solution was refluxed for 3-4 hr under argon atmosphere. The reaction mixture was filtered, concentrated and the residue was triturated with diethyl ether to obtain the crude product. The crude product was purified by silica column chromatography eluting with 4-5% MeOH/DCM to give yellow colored pure solid compound (0.5 g, 55% yield). $^1$H-NMR (500 MHz, CDCl$_3$): $\delta_H$ 0.875 (t, 3H), 1.25 (bs, 16H), 1.57-1.61 (m, 2H), 1.92-1.96 (dd, 3H), 2.18 (s, 3H), 2.3 (t, 2H), 3.07-3.13 (m, 4H), 3.63-4.04 (m, 12H), 4.14-4.45 (m, 12H), 4.89-5.06 (m, 2H), 6.84 (d, J=9 Hz, 2H), 6.93 (d, J=9 Hz, 2H), 7.31-7.36 (m, 2H), 7.48 (s, 2H), 7.7-7.72 (d, J=8.5 Hz, 1H), 9.9 (s, 1H). ESI-MS, m/z observed 933.8 (M), calculated 933.42 (M).

Example 6: Synthesis of Di-(ketoconazole-1-ethylene)]-DEG/TEG/PEG-Dicarbonate Conjugates 23a-c Di-(ketoconazole-1-ethylene)]-DEG/TEG/PEG-dicarbonateconjugates (23a-c) were synthesized as shown in Scheme 6.

Synthesis of [Di-(ketoconazole-1-ethylene)]-triethyleneglyceryl-dicarbonate Conjugate (23b)

Step-1: Synthesis of (Di-1-chloroethyl)-triethyleneglyceryl-dicarbonate (22b)

To a stirred solution of 1-chloroethylchloroformate (5.6 ml, 52 mmol) in 10 ml DCM was added the mixture of triethyleneglycol (3.0 g, 20 mmol) and triethylamine (6.9 ml, 50.0 mmol) dropwise by maintaining the temp at −15° C. The reaction mixture was allowed to reach room temperature and stirred for 6-8 h. After completion the reaction mixture was diluted with DCM, washed with water, brine and finally dried over sodium sulfate. The organic layer was evaporated to get the crude mass. The crude (4.1 gm, 65%) was used directly for the next step without further purification.

Step-2: Synthesis of [Di-(ketoconazole-1-ethylene)]-triethyleneglyceryl-dicarbonate Conjugate (23b)

To a stirred solution of Di-[1-chloroethyl-triethyleneglycerylcarbonate] (0.3 g, 0.94 mmol) in 10 ml acetonitrile was added sodium iodide (0.35 g, 2.35 mmol) and ketoconazole (1.0 g, 1.88 mmol). The reaction mixture was heated at 85° C. for 4-5 hr. The resultant solution was cooled to room

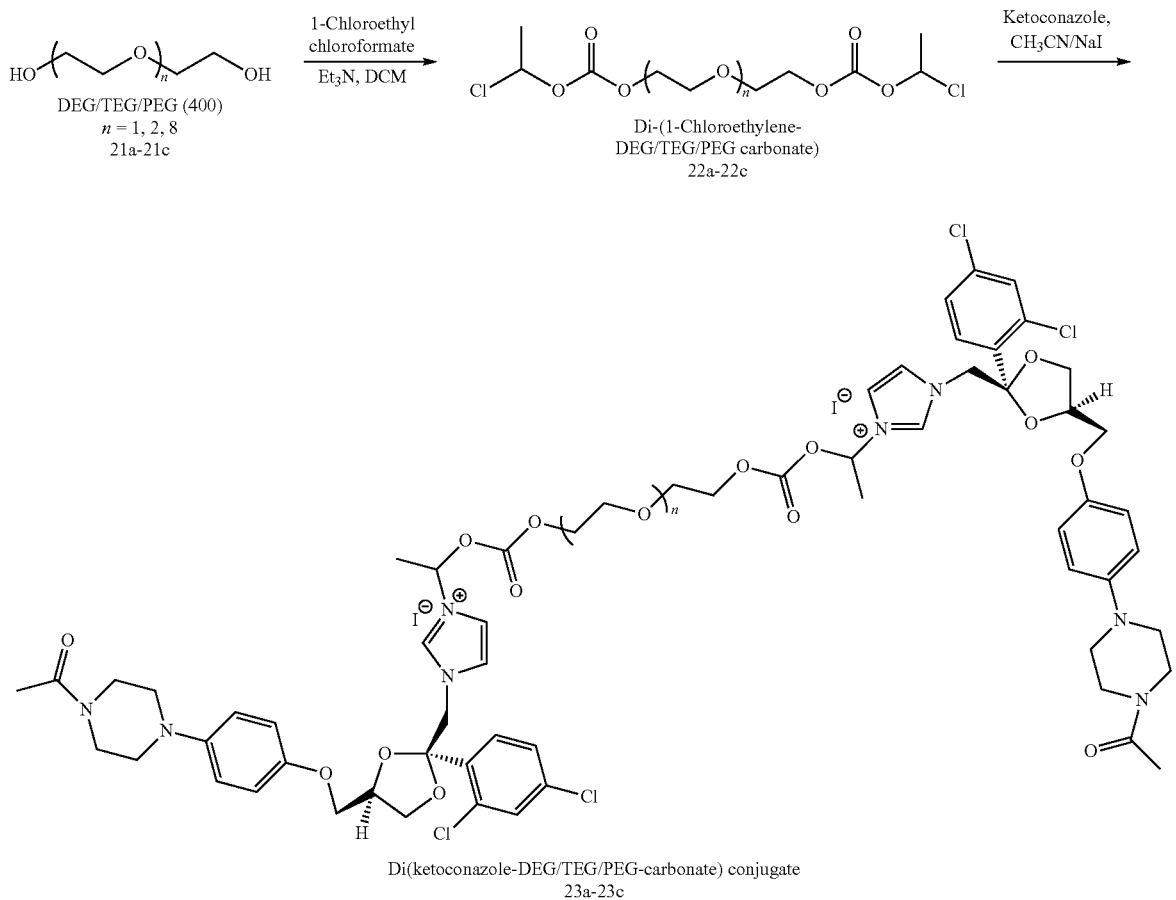

Di(ketoconazole-DEG/TEG/PEG-carbonate) conjugate
23a-23c temperature, filtered and concentrated to get the crude mass. The crude was purified by flash silica column chromatography and eluted with 5-6% MeOH/DCM to obtain yellow colored pure solid compound with 50% (0.75 gm) isolated yield. $^1$H-NMR (500 MHz, CDCl$_3$): $\delta_H$ 1.86-1.93 (t, 6H), 2.15 (s, 6H), 3.09-3.27 (dd, 8H), 3.62-3.97 (m, 32H), 4.15-4.367 (m, 4H), 4.86-5.0 (m, 4H), 6.6-6.67 (d, 2H), 6.84 (d, J=9 Hz, 4H), 6.93 (d, J=9 Hz, 4H), 7.31-7.36 (m, 4H), 7.48 (s, 4H), 7.7-7.72 (d, J=8.5 Hz, 2H), 9.9 (s, 2H). MALDI-TOF, m/z observed 1479.4 (M+Iodide counter ion), calculated 1352.4 (M).

Example 7: Synthesis of Di-(ketoconazole-methylene-acid ester) Conjugates

Di-(ketoconazole-methylene-acid ester) conjugate (26) was synthesized as shown in Scheme 7.

finally dried over sodium sulfate to obtain pure Di-(1-chloromethyl)-nonane-diacid ester (3.8 g, 85% yield).

Step-2: Synthesis of [Di-(Ketoconazole-methylene)]-nonane-diester Conjugate)(26)

Ketoconazole (7.48 g, 14.08 mmol), (Di-1-chloromethyl)-nonane-diester (2.0 g, 7.04 mmol), sodium iodide (2.1 g, 14.08 mmol), were suspended in acetonitrile and the resultant solution was refluxed for 4 hr under argon atmosphere. The reaction mixture was filtered, concentrated and the residue was triturated with diethyl ether to obtain a crude product. The crude product was purified by silica (60-120 mesh) column chromatography eluting with 4-5% MeOH/DCM to give yellow colored solid compound (5 gm, 50% yield). $^1$H-NMR (500 MHz, CDCl$_3$): $\delta_H$ 1.23-1.26 (m, 3H),

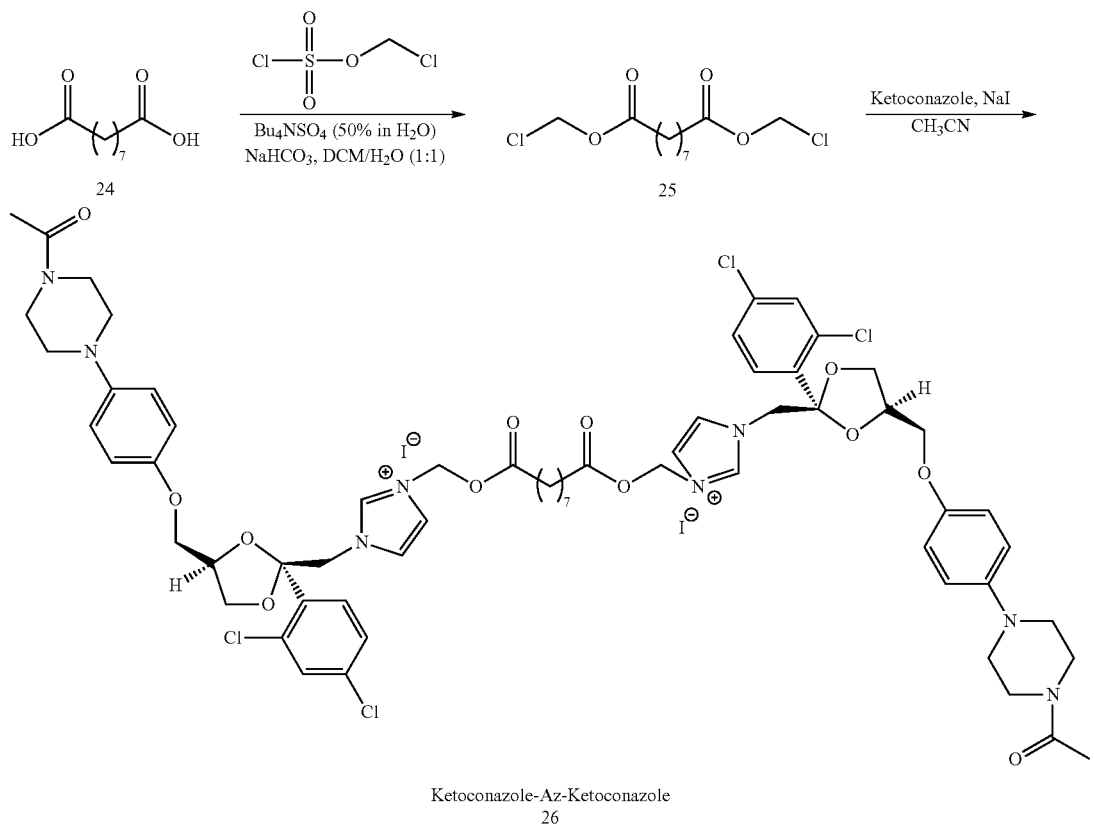

Scheme 7

Ketoconazole-Az-Ketoconazole
26

Step-1: Synthesis of (Di-1-chloromethyl)-nonane-diester (25)

Azelaic acid (3.0 g, 15.94 mmol) was dissolved in 50 ml DCM followed by addition of sodium bicarbonate (10.71 g, 127.52 mmol), 50 ml water and tetrabutylammonium sulfate (3.7 ml, 3.19 mmol). The resultant solution was stirred vigorously at 0° C. After 10 min, chloromethyl chlorosulfate (3.9 ml, 38.25 mmol) in DCM was added into the reaction mixture and the resultant solution was allowed to stir vigorously until room temperature was reached. The organic layer was extracted with DCM, washed with brine and 1.52-1.61 (m, 2H), 2.16 (s, 3H), 2.29 (q, 2H), 3.07-3.14 (dd, 4H), 3.667-3.71 (d, 3H), 3.74-3.75 (d, 2H), 3.72 (m, 1H), 3.81-4.11 (m, 2H), 4.12-4.413 (m, 1H), 4.856 (s, 2H), 6.0-6.117 (dd, 2H), 6.84 (d, J=9 Hz, 2H), 6.93 (d, J=9 Hz, 2H), 7.31-7.36 (m, 2H), 7.48 (s, 2H), 7.7-7.72 (d, J=8.5 Hz, 1H), 9.9 (s, 1H).

Example 8: Synthesis of Itraconazole-Methylene-Fatty Acid Ester Conjugates

Itraconazole-methylene-fatty acid ester conjugates (27a-g) were synthesized as shown in Scheme 8.

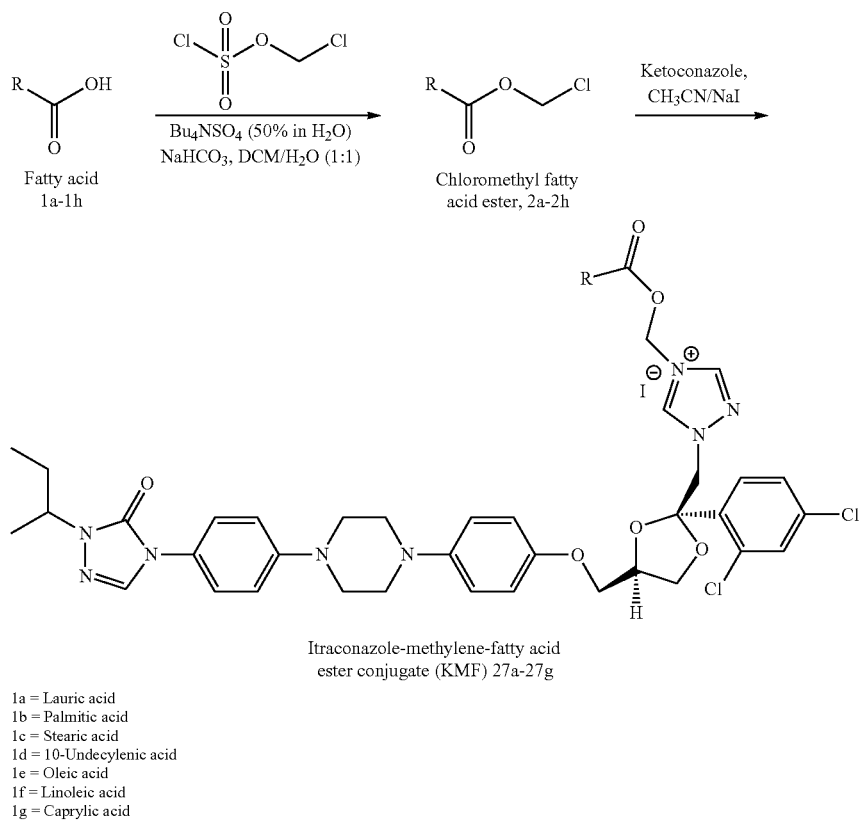

Scheme 8

1a = Lauric acid
1b = Palmitic acid
1c = Stearic acid
1d = 10-Undecylenic acid
1e = Oleic acid
1f = Linoleic acid
1g = Caprylic acid Synthesis of Itraconazole-methylene-caprylate Conjugates (27g)

Step-1: Synthesis of Chloromethyl Caprylate (2g)

Caprylic acid (5.0 g, 34.7 mmol) was dissolved in 40 ml DCM followed by addition of sodium bicarbonate (11.66 g, 138.8 mmol), 40 ml water and tetrabutylammonium sulfate (3.7 ml, 3.47 mmol). The resultant solution was stirred vigorously at 0° C. After 10 min, chloromethyl chlorosulfate (4.2 ml, 41.6 mmol) in DCM was added into the reaction mixture and the resultant solution was allowed to stir vigorously until room temperature was achieved. The organic layer was extracted with DCM, washed with brine and finally dried over sodium sulfate to obtain pure chloromethyl caprylate (5.3 g, 80% yield).

Step-2: Synthesis of Itraconazole-methylene-caprylate Conjugate (27G)

Itraconazole (3.67 g, 5.2 mmol), chloromethyl caprylate (2.0 g, 10.41 mmol), sodium iodide (1.56 g, 10.41 mmol), were suspended in acetonitrile and the resultant solution was refluxed for 4 hr under argon atmosphere. The reaction mixture was filtered, concentrated and the residue was triturated with diethyl ether to obtain a crude product. The crude product was purified by silica (60-120 mesh) column chromatography eluting with 4-5% MeOH/DCM to give yellow colored solid compound (2.7 gm, 60% yield). ESI-MS, m/z observed 861.7(M), calculated 861.36 (M).

Example 9: Nanoparticularization of Ketoconazole Prodrug Conjugates

The nanoparticularization of some of the ketoconazole-fatty acid conjugates were examined by two different methods: nanoprecipitation and nanoemulsion.

Nanoprecipitation:

In this method the prodrug conjugate and different external amphipathic carriers like lipid or polymer were initially dissolved in a mixture of tetrahydrofuran and acetone (1:3) solution and added dropwise into surfactant (0.1-0.25%) containing water under vigorous stirring condition. The final solution was then allowed to stir at room temperature for 18-20 hr to evaporate the organic solvent. The respected solution was then diluted, centrifuged and analyzed by zeta-sizer to obtain particle size and the homogeneity of the solution. Table 4 shows the compositions, sizes and polydispersity (PDI) of some of the nanoparticle prepared from ketoconazole-methylene-caprylate conjugate (KMC).

TABLE 4

| Prodrug conjugate | External carrier | Surfactant in $H_2O$ | $Z_{mg}$ nm (PDI) |
|---|---|---|---|
| KMC 15 mg | 15 mg Stearic acid-PEG-Stearic acid (SA-PEG-SA) | 0.25 % Polaxomer | 256.3-268.2 (0.142) |

TABLE 4-continued

| Prodrug conjugate | External carrier | Surfactant in H₂O | $Z_{mg}$nm (PDI) |
|---|---|---|---|
| | 15 mg SA-PEG-SA 30 mg PLGA | 0.5% PVA | 252.3-277.6 (0.15-0227.6) 213.3-230.2 (0.03-0.07) |
| | 0.1% Tween 80 | 0.25% Polaxomer | 185.5-210.4 (0.15-0.2) |
| | 30 mg Lecithin (from egg) | 0.25% Polaxomer | 178.2-190.8 (0.17-0.2) |

Nanoemulsion

In this process, prodrug was dissolved either in lauryl alcohol or a mixture of ethanol and captex 355 (Di/Triglyceride of caprylic acid). This lipid based solution was added into a particular percentage of surfactant, e.g. hydrogenated PEG 35 castor oil (Cremophor EL). The mixture of lipid and surfactant were then titrated against water until it forms cloudy liquids that apparently consist of coarse emulsion. The respected solution was analyzed by zeta-sizer to obtain particle size and the homogeneity of the solution. Table 5 shows the compositions and sizes of some of the nanoemulsion prepared from ketoconazole-methylene-caprylate conjugate (KMC).

TABLE 5

| Oil Phase | Surfactant | Oil:Surfactant | Water % | Droplet size (nm) |
|---|---|---|---|---|
| Lauryl alcohol | PEG-35 hydrogenated castor oil | 1:2 | 70 | 341 |
| | | | 80 | 273 |
| | | | 90 | 107 |
| Lauryl alcohol:Captex 355 (1:1) | PEG-35 hydrogenated castor oil | 1:2 | 70 | 1016 |
| | | | 80 | 274 |
| Captex 355:Ethanol (2:1) | PEG-35 hydrogenated castor oil | 1:2 | 70 | 140 |
| | | | 80 | 40 |
| | | | 90 | 33 |

Example 10: Synthesis of Antibacterial Clindamycin Conjugates

Clindamycin fatty acid conjugates, 32a-f, were synthesized as shown in Scheme 9.

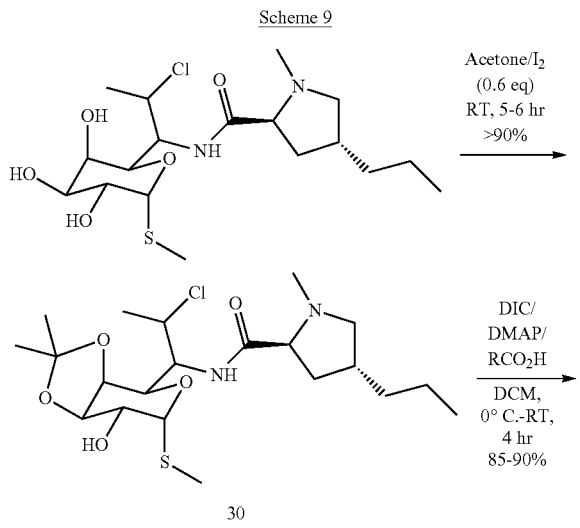

Scheme 9

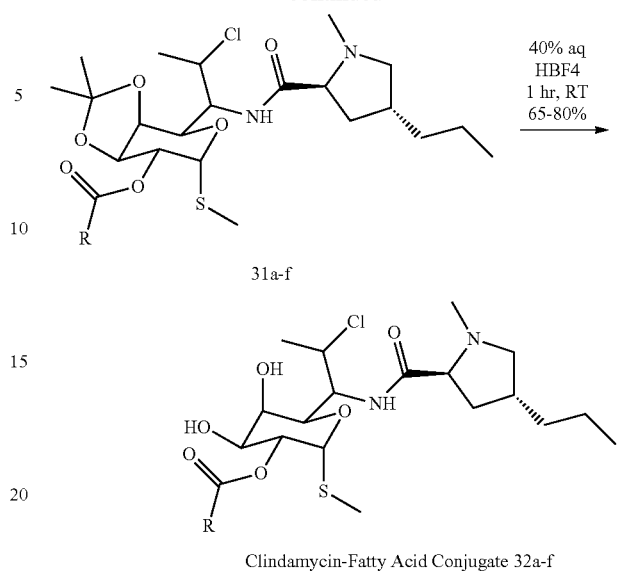

Clindamycin-Fatty Acid Conjugate 32a-f

Synthesis of Clindamycin Undecylenate (32a)

Step-1: Synthesis of Clindamycin Acetonide (30)

To a suspension of clindamycin hydrochloride (1 g, 2.167 mmol) in acetone (20 ml) was added iodine pellets (0.220 g, 0.866 mmol) under argon at RT. The reaction mixture was stirred at RT for 5-6 hrs. Iodine was then quenched with saturated aq. solution of Sodium thiosulphate and excess acetone was evaporated using rotary evaporator. The remaining aqueous phase was extracted with DCM (3×15 ml). The combined organics were washed with brine, dried with anhydrous sodium sulphate and concentrated in vacuo. The resulting residue was passed through a silica column (eluent—MeOH:DCM; 0.2:9.8) to obtain clindamycin acetonide as white fluffy powder. R$_f$0.6 (MeOH:DCM; 1:9)

Step-2: Synthesis of Clindamycin Acetonide Undecylenate (31a)

To a stirring solution of undecylenic acid (0.238 g, 1.292 mmol) in dry DCM was added DIC dropwise at 0° C. The reaction mixture was allowed to stir at RT for 15 min. Then a solution of clindamycin acetonide (0.5 g, 1.077 mmol) & DMAP (0.039 g, 0.323 mmol) in DCM was added dropwise at 0° C. and stirring was continued for further 4 hrs. The reaction mixture was diluted with DCM, quenched with saturated aq. solution of ammonium chloride and 1N HCl.

The combined organics were dried with anhydrous sodium sulphate and concentrated in vacuo. The resulting residue was passed through a silica column (eluent—MeOH:DCM; 0.1:9.9) to obtain clindamycin acetonide undecylenate as sticky yellow compound. $R_f$ 0.9 (MeOH:DCM; 1:9).

Step-3: Synthesis of Clindamycin Undecylenate (32a)

To a stirring solution of clindamycin acetonide undecylenate (0.713 g, 1.1308 mmol) in MeOH was added aq. $HBF_4$ (1.34 ml) dropwise at 0° C. The reaction mixture was allowed to stir at RT for 1 hr. Methanol was evaporated; aq. suspension of $NaHCO_3$ was added to the residue and then extracted with DCM (3×15 ml). The combined organics were dried with anhydrous sodium sulphate and concentrated in vacuo. The resulting residue was passed through a silica column (eluent—MeOH:DCM; 0.125:9.875) to obtain clindamycin undecylenate as syrupy pale yellow compound. $R_f$ 0.7 (MeOH:DCM; 1:9). $\delta_H$ (500 MHz, $CDCl_3$) 0.93 (3H, t, J 6.5), 1.25-1.45 (16H, m), 1.54 (3H, d, J 6.5), 1.66 (1H, m), 2.05 (2H, m), 2.11 (2H, m), 2.14 (3H, s), 2.41 (2H, t, J 7.5), 2.45 (3H, s), 2.75 (1H, d, J 10.5), 3.09 (1H, dd, J 7.0 and 3.0), 3.25 (1H, br s), 3.67-3.69 (2H, m), 3.87 (1H, dd, J 9.5 and 10.0), 4.10 (1H, d, J 9.5), 4.20 (1H, dd, J 9.5 and 10.0), 4.72 (1H, q, J 7.0), 4.94 (1H, d, J 10.5), 5.00 (1H, d, J 17.0), 5.13 (1H, br s), 5.16 (1H, dd, J 5.5 and 10.0), 5.56 (1H, d, J 5.5), 5.79-5.87 (1H, m), 8.13 (1H, d, J 9.0). HRMS, m/z observed 591.2728, $C_{29}H_{52}ClN_2O_6S^+$ (M+H)$^+$ calculated 591.3229.

Synthesis of Clindamycin Palmitate (32b)

Clindamycin palmitate was synthesized from clindamycin in a similar way as described for clindamycin undecylenate. $\delta_H$ (500 MHz, $CDCl_3$) 0.92 (6H, m, J 6.5), 1.25-1.52 (24H, m), 1.53 (3H, J 6.5), 1.67 (2H, m), 1.95 (2H, m), 2.11 (2H, m), 2.12 (3H, s), 2.38 (2H, t, J 7.5), 2.42 (3H, s), 2.73 (1H, d, J 10.5), 3.08 (1H, dd, J 10.5 and 3.5), 3.23 (1H, br s), 3.67 (1H, br s), 3.85 (1H, dd, J 10.5 and 10.0), 4.08 (1H, d, J 10), 4.19 (1H, dd, J 8.5 and 10.0), 4.72 (1H, q, J 6.5), 5.10 (1H, br s), 5.16 (1H, dd, J 5.5 and 10.0), 5.55 (1H, d, J 5.5), 8.115 (1H, d, J 9.5). HRMS, m/z Observed 663.6183, $C_{34}H_{64}ClN_2O_6S^+$ (M+H)$^+$ calculated 663.4168.

Similarly, other fatty acid conjugates were also synthesized from clindamycin using a similar procedure as shown above for 32b. Mass spectrometry data for some of the clindamycin conjugates fatty acid conjugates synthesized are shown in Table 6.

Example 11: Synthesis of Clindamycin Salicylic Acid Conjugate

Clindamycin salicylic acid conjugates was synthesized as shown in Scheme 10.

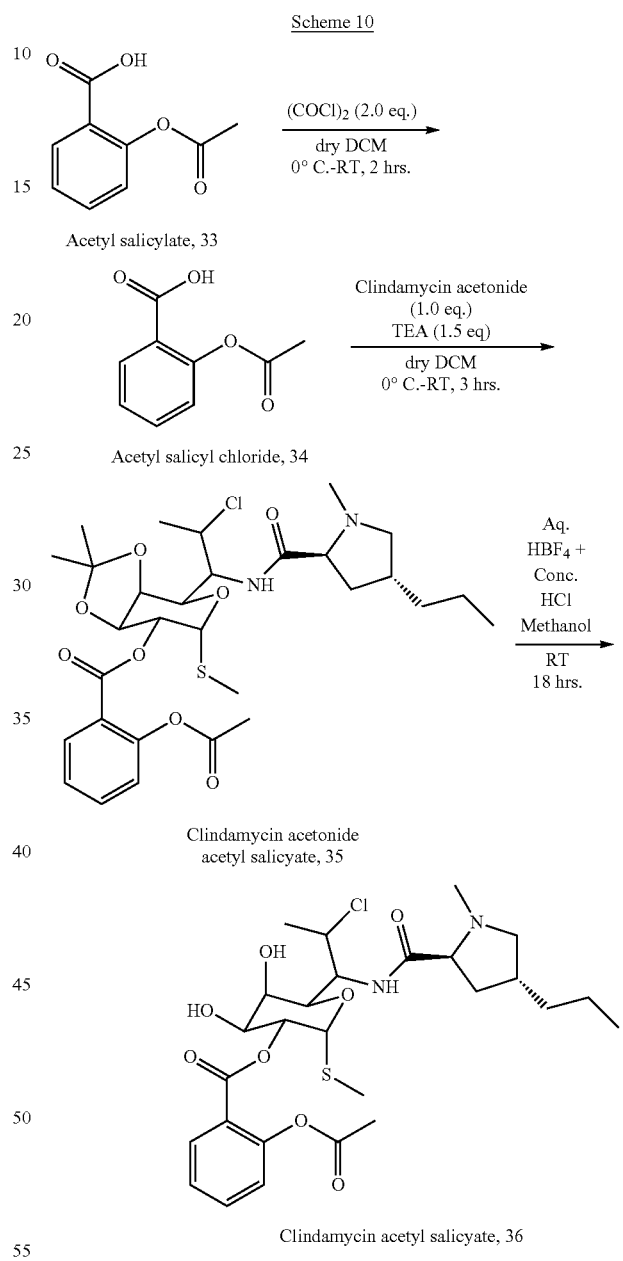

Scheme 10

Acetyl salicylate, 33

Acetyl salicyl chloride, 34

Clindamycin acetonide acetyl salicyate, 35

Clindamycin acetyl salicyate, 36

TABLE 6

| Compound name | Molecular formula | Mass Observed | Mass Calculated |
|---|---|---|---|
| Clindamycin laurate (32c) | $C_{30}H_{56}ClN_2O_6S^+$ [M + 1]$^+$ | 607.2750 | 607.3542 |
| Clindamycin stearate (32d) | $C_{36}H_{68}ClN_2O_6S^+$ [M + 1]$^+$ | 691.4557 | 691.4481 |
| Clindamycin oleate (32e) | $C_{36}H_{66}ClN_2O_6S^+$ [M + 1]$^+$ | 689.4393 | 689.4325 |
| Clindamycin linoleate (32f) | $C_{36}H_{64}ClN_2O_6S^+$ [M + 1]$^+$ | 687.4228 | 687.4168 |

Step-1: Synthesis of Clindamycin Acetonide (30)

To a suspension of clindamycin hydrochloride (1 g, 2.167 mmol) in acetone (20 ml) was added iodine pellets (0.220 g, 0.866 mmol) under argon at RT. The reaction mixture was stirred at RT for 5-6 hrs. Iodine was then quenched with saturated aq. solution of Sodium thiosulphate and excess acetone was evaporated using rotary evaporator. The remaining aqueous phase was extracted with DCM (3×15 ml). The combined organics were washed with brine, dried with anhydrous sodium sulphate and concentrated in vacuo. The resulting residue was passed through a silica column (eluent—MeOH:DCM; 0.2:9.8) to obtain clindamycin acetonide as white fluffy powder. $R_f$ 0.6 (MeOH:DCM; 1:9).

Step-2: Synthesis of Clindamycin Acetonide Acetyl Salicylate (35)

To the stirring reaction mixture containing oxalyl chloride (0.21 g, 1.666 mmol) in DCM, DMF (0.5 ml) was added dropwise at 0° C. After cessation of bubbling, this mixture was added to the stirring reaction mixture containing acetyl salicylate (aspirin) (0.15 g, 0.833 mmol) in DCM and allowed to stir for 2 hrs. The reaction mixture was added dropwise to the reaction mixture containing clindamycin acetonide (0.351 g, 0.7575 mmol), TEA (0.114 g, 1.1363 mmol) in dry DCM at 0° C. and stirred for 3 hrs. The reaction mixture was washed with 1N HCl and extracted with DCM. The combined organics were dried with anhydrous sodium sulphate and concentrated in vacuo to obtain yellowish powder. $R_f$ 0.4 (EtOAc:Hex; 1:1).

Step-3: Synthesis of Clindamycin Acetyl Salicylate (36)

To the stirring reaction mixture containing clindamycin acetonide acetyl salicylate (0.5 g, 0.7972 mmol) in MeOH, aq. $HBF_4$ (1.5 ml) was added dropwise at 0° C. and allowed to stir for 5 hrs. A few drops of Conc. HCl was added and stirred for 72 hrs. Methanol was evaporated and aq. suspension of $NaHCO_3$ was added and extracted with DCM (3×15 ml). The combined organics were dried with anhydrous sodium sulphate and concentrated in vacuo. The resulting residue was passed through a silica column (eluent—MeOH:DCM; 0.15:9.85) to obtain yellowish powder. $R_f$ 0.2 (MeOH:DCM; 0.2:9.8). $\delta_H$ (500 MHz, $CDCl_4$) 0.93 (6H, m), 1.250-1.411 (7H, m), 1.537 (3H, s), 2.005 (3H, s), 2.353-2.459 (1H, m), 2.485 (3H, br s), 3.014-3.038 (1H, m), 3.117 (1H, s), 3.298 (1H, m), 4.064-4.078 (1H, d, J 7), 4.437 (1H, m), 4.477 (1H, m), 4.553 (1H, m), 4.668 (1H, m), 4.668 (1H, m), 5.400-5.612 (2H, m), 6.886-6.917 (1H, m), 6.961-6.977 (1H, m), 7.14-7.19 (1H, m), 7.448-7.464 (1H, m), 7.859 (1H, br s), HRMS, m/z observed 545.2108, $C_{25}H_{38}ClN_2O_7S^+$ (M-Ac+H)$^+$ calculated 545.2083.

Similarly, other methylene fatty acid ester conjugates were also synthesized from ketoconazole using a similar procedure as described above for clindamycin acetyl salicylate 36.

Example 12: Synthesis of Clindamycin Dimer of Azelaic Acid

Clindamycin Dimer of Azelaic Acid (38) was carried out as shown in Scheme 11.

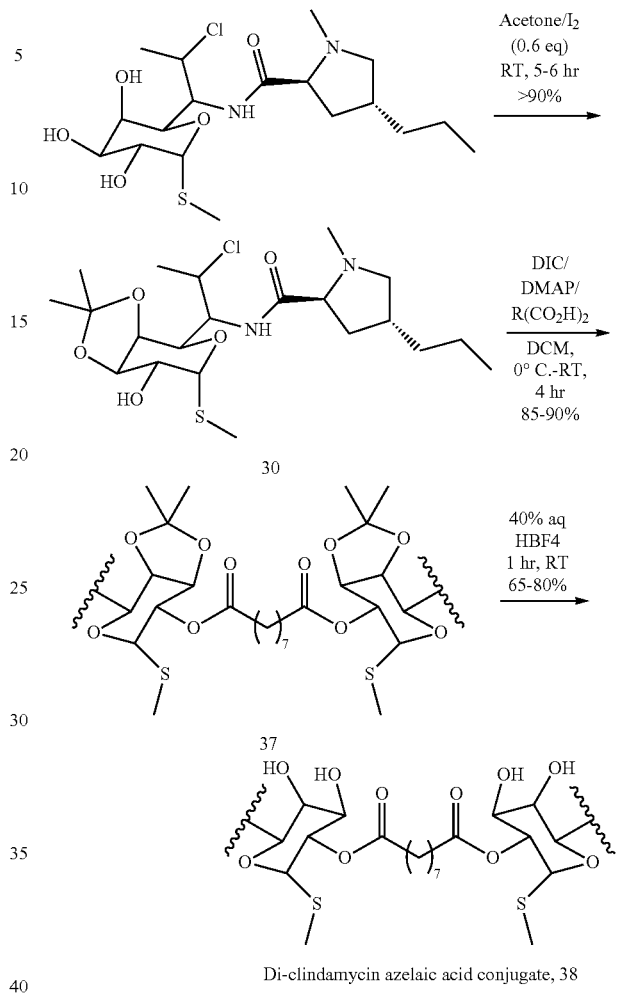

Scheme 11

Step-1: Synthesis of Clindamycin Acetonide (30)

To a suspension of clindamycin hydrochloride (1 g, 2.167 mmol) in acetone (20 ml) was added iodine pellets (0.220 g, 0.866 mmol) under argon at RT. The reaction mixture was stirred at RT for 5-6 hrs. Iodine was then quenched with saturated aq. solution of Sodium thiosulphate and excess acetone was evaporated using rotary evaporator. The remaining aqueous phase was extracted with DCM (3×15 ml). The combined organics were washed with brine, dried with anhydrous sodium sulphate and concentrated in vacuo. The resulting residue was passed through a silica column (eluent—MeOH:DCM; 0.2:9.8) to obtain clindamycin acetonide as white fluffy powder. $R_f$ 0.6 (MeOH:DCM; 1:9)

Step-2: Synthesis of Dimer of Clindamycin Acetonide with Azelaic Acid (37)

To a stirring solution of azelaic acid (0.202 g, 1.077 mmol) in dry DCM was added DIC (0.380 g, 3.015 mmol) dropwise at 0° C. The reaction mixture was allowed to stir at RT for 15 min. Then a solution of clindamycin acetonide (1.0 g, 2.154 mmol) & DMAP (0.078 g, 0.646 mmol) in DCM was added dropwise at 0° C. and stirring was continued for 4 hrs. The reaction mixture was quenched with saturated aq. solution of ammonium chloride and 1N HCl & extracted with DCM. The combined organics were dried with anhydrous sodium sulphate and concentrated in vacuo. The resulting residue was passed through a silica column (eluent—MeOH:DCM; 0.1:9.9) to obtain desired clindamycin derivative as solid colourless compound. $R_f$ 0.8 (MeOH:DCM; 1:9).

Step-3: Synthesis of Dimer of Clindamycin with Azelaic Acid (38)

To the stirring reaction mixture containing clindamycin acetonide dimer (0.690 g, 0.689 mmol) with azelaic acid in methanol, aq. $HBF_4$ (1.16 ml) was added dropwise at 0° C. and allowed to stir it for 2 hrs. Methanol was evaporated; aq. suspension of $NaHCO_3$ was added to the residue and then extracted with DCM (3×15 ml). The combined organics were dried with anhydrous sodium sulphate and concentrated in vacuo. The resulting residue was passed through a silica column (eluent—MeOH:DCM; 0.1:9.9) to obtain desired clindamycin dimer derivative as solid colourless compound. $R_f$ 0.6 (MeOH:DCM; 1:9). $\delta_H$ (500 MHz, $CDCl_3$) 0.93 (6H, t, J 6.5,), 1.27-1.35 (8H, m,), 1.44 (2H, d, J 11.5), 1.54 (6H, d, J 7.0,), 1.66 (2H, m,), 2.05 (4H, m,), 2.11 (4H, m), 2.13 (6H, s,), 2.41 (4H, t, J 7.5,), 2.45 (6H, br s,), 2.75 (2H, d, J 11,), 3.08 (2H, dd, J 10.0 and 3.0,), 3.25 (2H, br s,), 3.69 (2H, m,), 3.86 (2H, dd, J 10.0 and 10.0,), 4.10 (2H, d, J 9.5,), 4.19 (2H, dd, J 9.5 and 9.5,), 4.73 (2H, q, J 6.5,), 5.11 (2H, br s,), 5.16 (2H, dd, J 5.5 and 10.0,), 5.55-5.56 (2H, d, J 5.5,), 8.12 (2H, d, J 0.9). ESI-MS, m/z observed 501.73, $C_{45}H_{80}Cl_2N_4O_{12}S_2^{2+}$ $[M+2H)/2]^{+2}$ calculated 501.23.

Example 13: Synthesis of Clindamycin Triclosan Conjugate

Clindamycin triclosan conjugate (41) was synthesized as shown in Scheme 12.

Scheme 12
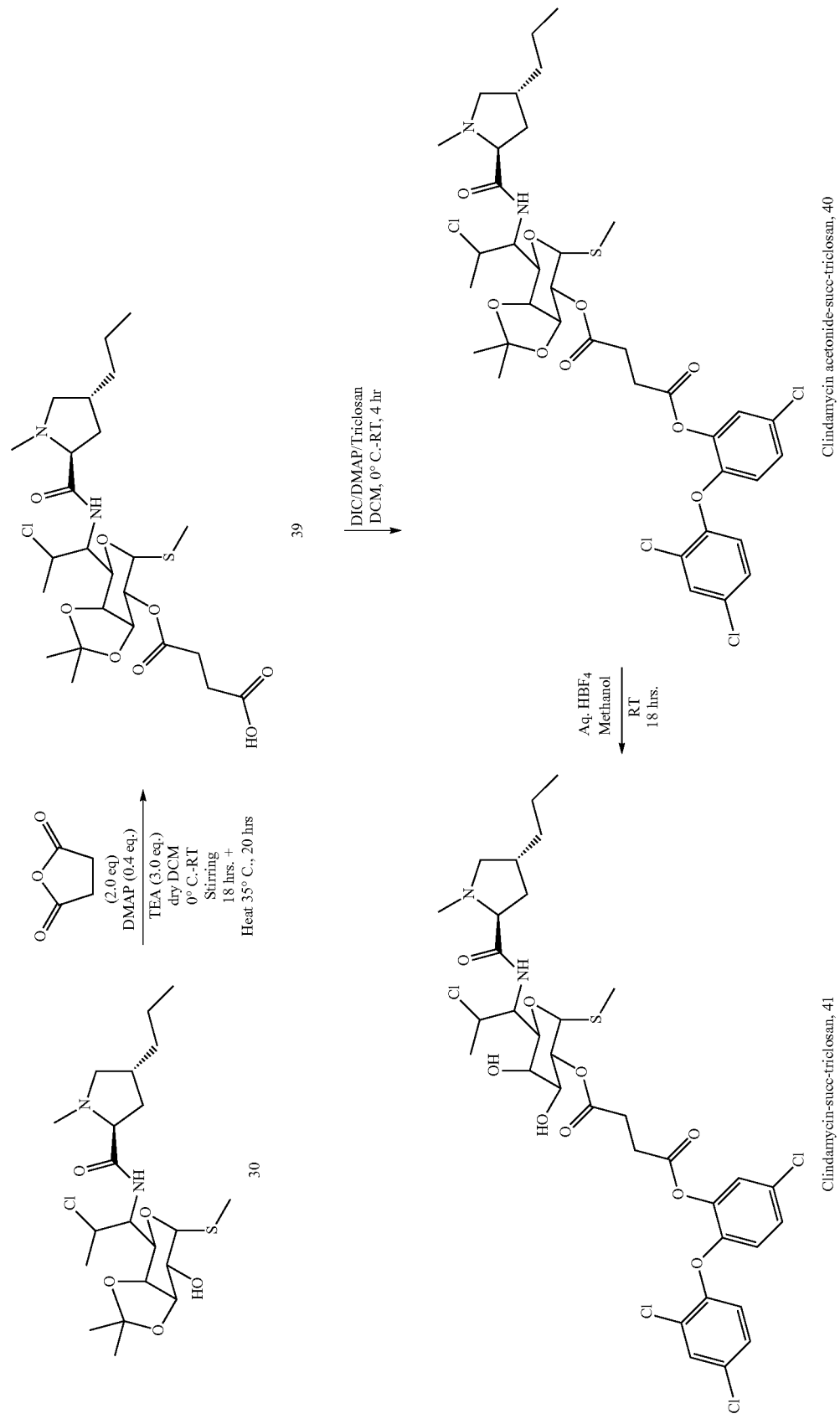

Step-1: Synthesis of Clindamycin Acetonide Succinate (39)

To the stirring reaction mixture containing succinic anhydride (0.214 g, 2.154 mmol) in THF, a solution of DMAP (N,N'-Dimethyl aminopyridine) (0.052 g, 0.4308 mmol) in THF was added dropwise at 0° C. and allowed to stir for 1 hr. To the above stirring reaction mixture, a solution of clindamycin acetonide (0.5 g, 1.077 mmol) and TEA in THF was added dropwise at 0° C. and allowed to stir for 18 hrs. Then it was heated at 35° C. for 20 hrs. The stirring reaction mixture was concentrated in vacuo. The residue was washed with 1N HCl and extracted with DCM (3×15 ml). The combined organics were dried with anhydrous sodium sulphate and concentrated in vacuo. $R_f$ 0.4 (MeOH:DCM; 1:9).

Step-2: Synthesis of Clindamycin Acetonide Succinate Triclosan (40)

To the stirring reaction mixture containing clindamycin acetonide succinate (0.323 g, 0.5715 mmol) in dry DCM, DIC (0.1 g, 0.8001 mmol) was added dropwise at 0° C. and allowed to stir for 10 minutes. To the above stirring reaction mixture, a solution of triclosan (0.165 g, 0.5715 mmol) and DMAP (N,N'-Dimethyl aminopyridine) (0.020 g, 0.1714 mmol) in dry DCM was added dropwise at 0° C. and allowed to stir for 3 hrs. The reaction mixture was quenched with saturated aq. solution of ammonium chloride and 1N HCl & extracted with DCM (3×15 ml). The combined organics were dried with anhydrous sodium sulphate and concentrated in vacuo to obtain a sticky yellow compound. $R_f$ 0.9 (MeOH:DCM; 1:9).

Step-3: Synthesis of Clindamycin Succinate Triclosan (41)

To the stirring reaction mixture containing clindamycin acetonide succinate triclosan (0.210 g, 0.2510 mmol) in MeOH, aq. $HBF_4$ (0.4 ml) was added dropwise at 0° C. and allowed to stir for 18 hrs. Methanol was evaporated; aq. suspension of $NaHCO_3$ was added and extracted with DCM (3×ml). The combined organics were dried with anhydrous sodium sulphate and concentrated in vacuo. The resulting residue was passed through a silica column (eluent—MeOH:DCM; 1:9) to obtain yellowish powder. $R_f$ 0.7 (MeOH:DCM; 0.2:9.8). $\delta_H$ (500 MHz, $CDCl_3$) 0.90 (3H, m), 1.135-1.467 (7H, m), 1.514 (3H, s), 2.160 (3H, s), 2.472 (3H, br s), 2.719-2.826 (3H, m), 3.039-3.077 (1H, m), 3.117 (1H, br s), 3.190-3.229 (1H, d, J 19.5), 3.663-3.688 (1H, m), 3.847 (1H, m), 3.979-4.011 (1H, m), 4.058-4.076 (1H, d, J 9), 4.152-4.169 (1H, d, J 8.5), 4.348-4.468 (2H, m), 4.686 (1H, br s), 5.159-5.149 (1H, br s), 5.489 (1H, m), 6.814-6.797 (1H, d, J 8.5), 6.875-6.857 (1H, d, J 9), 7.229-7.142 (3H, m), 7.449 (1H, s). ESI-MS, m/z observed 797.07, $C_{34}H_{43}Cl_4H_2O_9S^+$ $(M+H)^+$ calculated 797.14.

Example 14: Synthesis of Triclosan Fatty Acid Conjugate

Triclosan fatty acid conjugate (43) was synthesized as shown in Scheme 13.

Scheme 13

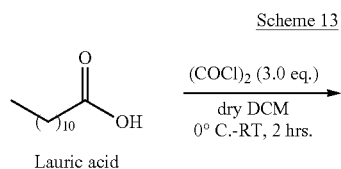

Lauric acid

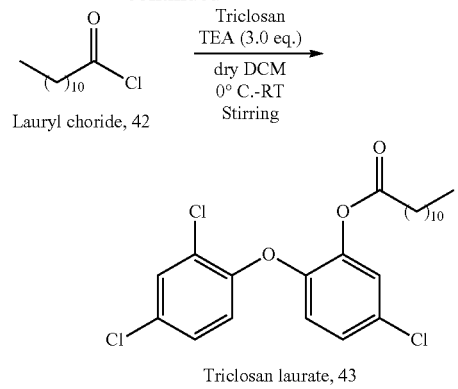

Lauryl choride, 42

Triclosan laurate, 43

Step-1: Synthesis of Triclosan Laurate (43)

To the stirring reaction mixture containing oxalyl chloride (2.534 g, 19.96 mmol) in DCM, DMF (0.6 ml) was added dropwise at 0° C. After cessation of bubbling, this mixture was added to the stirring reaction mixture containing lauric acid (2.0 g, 9.98 mmol) in DCM and allowed to stir for 2 hrs. The reaction mixture was added dropwise to the reaction mixture containing triclosan (2.64 g, 9.14 mmol), TEA (2.09 g, 20.72 mmol) in dry DCM at 0° C. and stirred for 3 hrs. The reaction mixture was washed with 1N HCl and extracted with DCM. The combined organics were dried with anhydrous sodium sulphate and concentrated in vacuo. The resulting residue was passed through a silica column (eluent—MeOH:DCM; 0:10) to obtain oily liquid. $R_f$ 0.9 (MeOH:DCM; 0.2:10). $\delta_H$ (500 MHz, $CDCl_3$) 0.881 (3H, t, J 6.5), 1.230-1.252 (16H, m), 1.632 (2H, quin, J 7, 7.5), 2.463 (2H, t, J 7.5), 6.838 (1H, d, J 3), 6.856 (1H, d, J 3.5), 7.149-7.157 (1H, m), 7.186-7.191 (1H, m), 7.444 (1H, d, J 2.5) ESI-MS, m/z observed $C_{24}H_{29}Cl_3O_3$ observed 501.73, $C_{24}H_{29}Cl_3O_3^+$ $[(M+2H)/2]^{2+}$ calculated 501.23.

Example 16: Preparation of Nanoparticles of Clindamycin Conjugates

Some of the clindamycin prodrug clindamycin conjugates were subjected to nanoparticles formation. The nanoparticles were formed by two techniques: polymeric nanoparticles by nanoprecipitation, and self-assembly nanoparticles by film-hydration method.

Polymeric Nanoparticles by Nanoprecipitation:

Clindamycin undecylenate (25 mg) was dissolved in THF (1.0 ml). This solution was then added dropwise to 1% PVA aqueous solution while stirring at 1200 rpm at RT. The stirring was continued for 24 hrs to get rid of THF. The dispersion was then centrifuged at 1000 rpm for 10 min to remove any larger particles. As shown in FIG. 23, the resulting dispersion had an average particle size of about 218 nm with a sharp distribution (PDI=0.149).

Self-Assembly Nanoparticles by Film-Hydration Method:

Egg lecithin (3 mg) and clindamycin laurate (10 mg) were dissolved in 4.0 ml dichloromethane. The solvent was removed under vacuum and the residue was hydrated with 1.0 ml of water. The resulting mixture was rotated on a rotary evaporator at atmospheric pressure at 60° C. for 1 hr to get crude self-assembled particles (or liposomes). The crude particles were passed through Sephadex G-25 column to remove any free clindamycin laurate. The initial turbid fractions were collected, pooled together and finally passed through a size extruder (30× to and fro) fixed with 200 nm membrane. The processed liposomal suspension was characterized by Malvern ZetaSizer to obtain the size distribution. The distribution obtained was narrow and the average size of the liposomes was about 158 nm as shown in FIG. 24.

Example 17: In Vitro Biological Efficacy Studies of Synthesized Antifungal Conjugates The efficacy of the antifungal conjugates of the present invention were investigated mainly by three methods:
(i) Determination of Minimum Inhibitory Concentration (MIC) by a) agar plate serial dilution and b) by broth macro and micro dilution method
(ii) Determination of Zone of Inhibition (ZOI) by a) agar well diffusion methods and b) Kirby Bauer disk diffusion methods
(iii) Time Kill Kinetics assay by Alamar blue and viable count method Minimum Inhibitory Concentration (MIC):

Here MIC is considered as the minimum inhibitory concentration that inhibits 100% growth of the fungus, which is equivalent to minimum fungicidal concentration (MFC).

*M. furfur* is grown on agar plates which are made with Leeming Notman (LN) medium [*Journal of Clinical Microbiology* (1987), 25:2017-9 and the references therein]. For MIC by agar dilution method, appropriate dilutions of solubilized antifungal compositions were added to the autoclaved cylinders containing molten LN medium. The solutions were vortexed and the contents poured into separate sterile petri dishes labeled accordingly. Once the plates were set, *M. furfur* innoculum adjusted to certain CFU/ml, was streaked on the agar plates and incubated for 2 days in $CO_2$ atmosphere. After incubation, the plates were observed visually to see *M. furfur* growth. The MIC is defined as the lowest tested dilution of antifungal active that yields no growth. Comparison of the MIC values of antifungal active to that of MIC value for control compound, ketoconazole was done. Potency of an antifungal active was indicated by the corresponding MIC value.

Equipment and Reagents:

Microbe: *Malassezia furfur* (MTCC 1374); agar medium: 60 ml Leeming Notman medium for each active to be tested at their respective concentrations; solvent: DMSO (Dimethylsulfoxide), water, other suitable for actives; Petri dishes: 3 dishes per anti-fungal active per concentration to be tested, sterilized, size=15 mm×100 mm.

Experimental Procedure:

Broth and agar dilution are routinely used methods for antimicrobial susceptibility testing. Accordingly, to study MIC, agar plate dilution method was employed with LN medium. Each experimental setup was done in triplicates and was performed as follows:
(i) LN medium was prepared according to the manufacturer's instructions.
(ii) The medium was autoclaved (121° C., 15 min), cooled to 50° C. Antibiotics chloramphenicol (working concentration 0.25 mg/ml) and cycloheximide (working concentration 0.04 mg/ml) and 2% olive oil were added accordingly.
(iii) Once the medium was cooled, the required amount of antifungal composition and control solutions were calculated. Stocks of antifungal composition and control were prepared with certain concentrations in DMSO. The range of concentrations was examined according to the MIC of an antifungal.
(iv) Appropriate volume (for the highest dilution) was taken from the stocks respectively and diluted further with the LN media to achieve the required range in the final volume.
(v) As an example, first dilution was made up to 120 ml and mixed in the 200 ml autoclaved cylinder under sterile conditions, vortexed for 20 sec and poured each 20 ml in appropriately labeled three sterile petri plates. Similarly, controls were also prepared with the above procedure. In this way all the dilutions were done and the agar plates with the antifungal composition and control were prepared.
(vi) The plates were left to solidify in the biosafety hood, after solidification, stacked and stored them for the contamination check which was done on the next day.
(vii) Preparation of innoculum was done on the next day, innoculum density was adjusted to $5.1 \times 10^3$ and the agar plates with the drug were streaked aseptically.
(viii) Plates were incubated in $CO_2$ incubator at $(30\pm2)°$ C. and 5% $CO_2$ and the readout was taken after every 24 hr for 6 days.

FIG. 25 shows representative photographs of MIC agar plate assay for the TEG based conjugates. FIG. 26 shows representative photographs of MIC agar plate assay for the methylene and ethylene based conjugates. FIG. 27 shows representative photographs of MIC agar plate assay for conjugates KMP and KAH.

MIC values for some of the exemplary ketoconazole prodrug conjugates are summarized in Table 7.

TABLE 7

MIC values of some exemplary conjugates of Ketoconazole.

| Conjugate | MIC (µM) |
|---|---|
| Ketoconazole-methylene-caprylate (KMC) | 0.94-3.7 |
| Ketoconazole-methylene-oleate (KMO) | 1.88-7.5 |
| Ketoconazole-methylene-linolate (KMLi) | 7.5 |
| Ketoconazole-methylene-laureate (KML) | 1.88-3.7 |
| Ketoconazole-methylene-undecylenate (KMU) | 3.7-7.5 |
| Ketoconazole-methylene-palmitate (KMP) | 1.88 |
| Ketoconazole-ethylene-caprylate (KEC) | 1.88 |
| Ketoconazole-1-ethylene-oleate (KEO) | 1.88-3.7 |
| Ketoconazole-1-ethylene-laureate (KEL) | 1.88-3.7 |
| Ketoconazole-1-ethylene-undecylenate (KEU) | 1.88-7.5 |
| Ketoconazole-1-ethylene-palmitate (KEP) | 3.7-7.5 |
| Ketoconazole-1-ethylene-myristate (KEM) | 1.88-3.7 |
| Ketoconazole-1-ethylene-oleylcarbonate (KCO) | 1.88 |
| Ketoconazole-triethyleneglyceryl-Ketoconazole | 0.94-3.7 |
| Ketoconazole-oleyl-triethyleneglycerylcarbonate | 7.5-15 |

Comparative Studies of Ketoconazole Conjugates by Zone of Inhibition (ZOI) Assay:

*Malassezia furfur* is a normal micro flora of the human skin secretes extracellular lipases which act on the ester/carbonate linkages of the fatty-acids in their surrounding environment and provide nutrition for their survival. A negative control compound, Keto-N-hexadecylacetamide (KAH), was synthesized as described in Example 3. KAH acts as a negative control as the linker between fatty acids and ketoconazole is an amide linkage. Lipases cannot act on the amide linkage and cleave the compound back to ketoconazole. Comparative biological efficacy studies were carried out with the ketoconazole conjugates (KMP) with negative control (KAH) and positive control ketoconazole.

Determination of ZOI by agar well diffusion method was employed to study the complete inhibition of the growth of microorganism.

Equipment and Reagents:

Microbe: *Malassezia furfur* (MTCC 1374); agar medium: 60 ml Leeming Notman medium for each active to be tested at their respective concentrations; solvent: DMSO, water and other suitable for actives; Petri dishes: 3 dishes per anti-fungal active per concentration to be tested, sterilized, size=15 mm×100 mm; and sterile straws for punching holes (6 mm diameter) into the agar plate Experimental Procedure:

Determination of ZOI by agar well diffusion method was employed to show the inhibition of the growth of microorganism. Experiments were performed as follows:
  (i) Sabaroud's Dextrose agar (SDA) medium was prepared according to the manufacturer's instructions.
  (ii) The SDA medium was autoclaved (121° C., 15 min), cooled to 50° C. Chloramphenicol (working concentration 0.25 mg/ml), cycloheximide (working concentration 0.04 mg/ml) and 2% olive oil were added accordingly.
  (iii) Preparation of Innoculum was done by hemocytometer, innoculum density was adjusted to $5.1 \times 10^3$ and the agar plates with the drug were streaked aseptically.
  (iv) Once the medium was cooled, sterile straws were used to punch the wells of 6 mm wide on the agar plates.
  (v) The amount of antifungal composition and control solutions was calculated as needed.

Stocks of antifungal composition and control were prepared in DMSO with certain concentrations.
  (vi) Appropriate volume of 60 µl was taken from the stocks with respective concentrations of the prodrugs along with the negative control compounds.
  (vii) Plates were incubated in $CO_2$ incubator at $(30\pm2)°$ C. and 5% $CO_2$ and the readout was taken after every 24 hr for 6 days. ZOI is defined as the lowest concentration of the drug where complete inhibition of *M. furfur* was noticed around the well.

FIG. 28 shows a photograph of a representative ZOI as determined by agar well diffusion method. As the data summarized in FIG. 29 shows, inhibition zone sizes for the ketoconazole-fatty acid conjugates and the ketoconazole were similar. However, the inhibition zone size for the negative control KAH was non-existent.

Time Kill Kinetics Assay:

Experiments were conducted to show the inhibition of growth of microorganisms. Determination of the killing of a yeast isolate by one or more antifungal agents under controlled conditions is known as Time Kill assay. The time kill kinetics results are an indicative measure for anti-fungal/bacterial efficacy. Generally the inhibition of the fungal growth is directly proportional to the anti-fungal efficacy of the prodrug compounds tested.

A flask containing the media Sabouraud's Dextrose Broth (SDB) with 2% olive oil was innoculated with *Malassezia furfur*. Specific concentrations of the active prodrug compounds along with control compound, ketoconazole was then added to the broth medium. Samples were withdrawn from the flask at predetermined time points, diluted with sterile water and streaked on SDA agar plates. Visual growth of the *M. furfur* colonies was observed after incubation of the plates at certain temperature. The number of colonies observed were counted and converted the numbers into Colony Forming Units per ml i.e. CFU/ml of SDB medium. Therefore lower the CFU/ml value, better the antifungal effect of the compounds tested.

Equipment and Reagents:

Microbe: *Malassezia furfur* (MTCC 1374); agar medium: 60 ml Leeming Notman medium for each active to be tested at their respective concentrations; solvent: DMSO, water, and other suitables for actives; Petri dishes: 3 dishes per anti-fungal active per concentration per active to be tested, sterilized, size=15 mm×100 mm; and tubes: 15 ml falcon sterile tubes.

Experimental Procedure:

The experiment was performed as follow:
  (i) *M. furfur* was brought to log phase by culturing it overnight on SDA agar plates. Cell concentration was determined by hemocytometer for the starting innoculum density of the experiment, 1 ml of the adjusted innoculum was added to 9 ml of SDB with 2% olive oil that has cycloheximide and chloramphenicol antibiotics.
  (ii) After adding the broth, innoculum density was reduced to dilution factor 1:10, for instance starting innoculum was $5 \times 10^5$ CFU/ml which was diluted to $5 \times 10^4$ CFU/ml.
  (iii) 1.5 ml each of the broth-diluted innoculum was added to 15 ml falcon tubes. These reaction tubes were prepared for 0.25×MIC, 0.5×MIC, 1×MIC, 2×MIC, and 4×MIC and 8×MIC concentrations of the prodrug compounds and the tubes were vortexed gently.
  (iv) Predetermined points were selected accordingly. At every time interval 100 µl each was pipette out and vortexed for 30 seconds. The reaction tubes were returned back to the incubator at 30° C., 5% $CO_2$ as soon as possible.
  (v) From 100 µl solution, 30 µl each was plated on to the SDA agar plates. Once the plates were streaked and incubated, the colonies were counted manually after 48 h Standardized parameters for the antifungal time-kill testing of yeasts are shown in Table 8. Results of time kill kinetic assay are shown in Table 9 and FIGS. 30-31B. Data in FIG. 30 Time Kill curves at 4 hr with 0.25 µg/ml showed better uptake of KMC as compared to ketoconazole. Thus, KMC was found to be faster acting at 0.25 µg/ml than ketoconazole This observation is valid for range of concentrations (0.125 to 1.0 µg/ml) of both ketoconazole and KMCs as demonstrated in FIGS. 31A and 31B.

TABLE 8

| Standardized protocol of time-kill assay of yeasts for antifungals | |
|---|---|
| Test method | Macrodilution (10 ml) time-kill |
| Medium | Sabouraud's Dextrose Broth (SDB) with 2% olive oil |
| Innoculum size | $5 \times 10^5$ CFU/ml |
| Incubation conditions (broth) | |
| Temp (° C.) | 35 |
| Duration (hr) | 24 |
| Sample times (hr) | 0, 2, 4, 8, 12, and 24 |
| Transfer vol (µl) | 30 |
| Vortex prior to sampling | Yes |
| Agar medium | Sabouraud's dextrose agar |
| Incubation conditions (agar) | |
| Temp (° C.) | 35 |
| Duration (h) | 48 |
| Limit of quantitation (CFU/ml) | 50 Interpretation |
| Fungicidal | 99.9% or 3-$\log_{10}$-unit decrease in CFU/ml compared to starting inoculums |

TABLE 9

Data for the time kill kinetics assay for ketoconazole, KMC and in absence of drug

| Antimicrobial Concentrations-(µg/ml) | Plate Area Colonized (mm²) | | | |
|---|---|---|---|---|
| | 0 hr | 2 hr | 4 hr | 6 hr |
| No drug | 1.00E+05 | 1.30E+06 | 2.30E+06 | 3.30E+06 |
| 0.125 µg/ml KMC | 1.00E+05 | 1.00E+06 | 6.60E+05 | 1.70E+05 |
| 0.125 µg/ml Ketoconazole | 1.00E+05 | 1.30E+06 | 6.80E+05 | 1.30E+05 |
| 0.25 µg/ml KMC | 1.00E+05 | 1.00E+06 | 1.00E+05 | 9.30E+04 |
| 0.25 µg/ml Ketoconazole | 1.00E+05 | 6.90E+05 | 6.10E+05 | 1.50E+05 |
| 0.5 µg/ml KMC | 1.00E+05 | 8.50E+05 | 4.30E+04 | 4.30E+04 |
| 0.5 µg/ml Ketoconazole | 1.00E+05 | 6.30E+05 | 8.50E+05 | 6.60E+04 |
| 1.0 µg/ml KMC | 1.00E+05 | 4.90E+05 | 6.00E+04 | 2.00E+04 |
| 1.0 µg/ml Ketoconazole | 1.00E+05 | 8.00E+05 | 7.60E+05 | 1.80E+05 |

Lipase Mediated Hydrolysis of Ketoconazole Conjugates:

In this study, lipase mediated hydrolysis of ketoconazole conjugates was studied.

Equipment and Reagents:

Microbe: *Malassezia furfur* (MTCC 1374); Medium: SDB 50 ml with two different concentrations (125 and 250 µg/ml) of actives to be tested; solvent: media, water, other suitable for actives; and tubes: 15 ml falcon sterile tubes.

Experimental Procedure:

The experiment was performed as follow:

(i) *M. furfur* was brought to log phase by culturing it overnight on SDA agar plates. Cell concentration was determined by hemocytometer for obtaining the starting innoculum density of the experiment.

(ii) 1 ml of the adjusted innoculum $10^5$ CFU/ml was added into 10 ml of SDB with 2% olive oil which has cycloheximide and chloramphenicol antibiotics along with the prodrug at 250 µg/ml concentration. The final mixture was vortexed for 30 sec.

(iii) 5 ml of the above mixture was pipetted out into a 15 ml falcon tube and 5 ml SDBO (SDB with olive oil) was added serially to make 125 µg/ml concentration of prodrug and the resulting solution was vortexed.

(iv) Similarly negative control KAH was taken in SDBO medium with the same conc. of prodrug without the innoculum. The tubes were later incubated at 32° C., 5% $CO_2$ On Day 3, 1 ml of the reaction mixture including that with KAH solution was taken out and extracted with with ethyl acetate for three times to quantitatively measure both the remaining prodrug and the converted drug under the same experimental conditions.

(v) The samples were concentrated and analyzed by HPLC.

As seen from the data in Table 10, the ketoconazole conjugates were sensitive to lipases secreted by the fungus with respect to amide conjugate, KAH. The determination of percentage cleavage of prodrug to drug was analyzed by HPLC. The test organism was *Malassezia furfur* and the testing principle was undertaken as the evaluation of the hydrolysis rate of the prodrugs.

TABLE 10

Lipase mediated cleavage of prodrugs to drug by HPLC analysis.

| | 125 µg/ml | | 250 µg/ml | |
|---|---|---|---|---|
| KAH + Innoculum | Keto = 19% | KAH = 80.4% | N/A | N/A |
| KAH (No innoculum) | Keto = 17.3% | KAH = 82.6% | N/A | N/A |
| KEC + Innoculum | Keto = 77.0% | KEC = 23% | Keto = 74.05% | KEC = 25.95% |
| KEC (Noinnoculum) | Keto = 21.8% | KEC = 78.19% | Keto = 16.8% | KEC = 83.2% |
| KMC + Innoculum | Keto = 78.0% | KMC = 21.0% | Keto = 71.7% | KMC = 28.2% |
| KMC (No innoculum) | Keto = 22.8% | KMC = 77.1% | Keto = 20.47% | KMC = 79.5% |

Example 18: In Vitro Efficacy Studies of Synthesized Antibacterial Conjugates

*S. aureus* causes skin infections in addition to much other type of infections. It can cause cellulitis (infection of the skin and tissue that lie immediately beneath the skin), boils (pus filled infections of hair follicles), abscesses (collection of pus in or under the skin), carbuncles (infections larger than an abscess, usually with several openings to the skin), impetigo (skin infection with pus-filled blisters), and rash (skin appears to be reddish or red-colored areas). To investigate the efficacy of the synthesized conjugates of the present invention experiments were conducted to show the complete inhibition of growth of the microorganisms. In this experiment, MIC was determination by agar plate serial dilution method to evaluate the efficacy of the synthesized conjugates.

Minimum Inhibitory Concentration (MIC):

MIC is an index which measures the anti-acne efficacy. Generally, lower the MIC values of the composition higher its antibacterial efficacy, because of its inherent ability to inhibit the growth of the bacteria.

In this experiment, *S. aureus* was grown on agar plates, which were made with Chapman Medium [*American Veterinary Research* (1947) 8:173]. For MIC by agar dilution method, appropriate dilutions of solubilized antibacterial compositions were added to autoclaved measuring cylinders containing molten Chapman Medium (CM). The cylinders were vortexed and the contents were poured into separate sterile petri dishes labeled accordingly. Once the plates were set, *S. aureus* innoculum adjusted to certain CFU/ml, was streaked on the agar plates and incubated for 2 days in an anaerobic jar. After incubation, the plates were observed for visible *S. aureus* growth. The MIC was defined as the lowest tested dilution of antibacterial active that yielded no growth. Comparison of the MIC values of antibacterial actives to that of MIC value of control compound clindamycin was done. Potency of an antibacterial active is indicated by the MIC value.

Equipment and Reagents:

Microbe: *S. aureus* (MTCC 3160); Agar medium: 60 ml Chapman medium for each active to be tested at their respective concentrations; solvent: DMSO (Dimethylsulfoxide), water, other suitable for actives; and sterilized petri dishes in triplicates per anti-fungal active per concentration to be tested.

Experimental Procedure:

Broth and agar dilution are routinely used methods for antimicrobial susceptibility testing. To study minimum inhibitory concentration, agar Plate dilution method was employed with Chapman medium. Each experiment setup was done in triplicates. The experiment was performed as follow:

(i) Chapman medium was prepared according to the manufacturer's instructions.
(ii) The medium was autoclaved (121° C., 15 min), cooled to 50° C. followed by addition of antibiotics.
(iii) Once the medium was cooled, the amount of antibacterial composition and control solutions were calculated as needed. Stocks of antibacterial composition and control were prepared in DMSO with required concentrations.
(iv) Appropriate volume was taken from the stocks respectively and diluted further with the Chapman media to achieve the required concentration range in the final volume.
(v) As an example, first dilution was made up to 120 ml and mixed under sterile conditions, vortexed for 20 sec and poured 20 ml each in appropriately labeled three sterile petri plates. Similarly, controls were also prepared with the above procedure.
(vi) The plates were left to solidify in the biosafety hood; after solidification, stacked and stored the plates.
(vii) Preparation of innoculum was done on the next day, innoculum density was adjusted and the agar plates with the drug were streaked aseptically.
(viii) Plates were incubated in incubator at (36±2)° C. under anaerobic conditions and the readout was taken after every 24 hr for 6 days. MIC is defined as the lowest concentration of the drug where complete inhibition of *S. aureus* is was noticed.

MIC values for some of the clindamycin prodrug conjugates are shown in Table 11.

TABLE 11

MIC values of different conjugates of clindamycin in µg/ml concentrations.

| Conjugate | MIC (µg/ml) |
| --- | --- |
| Clindamycin-palmitate | 128 |
| Clindamycin-laureate | 128 |
| Clindamycin-stearate | 32 |
| Clindamycin-10-undecylenate | 128 |
| Clindamycin-succinate-triclosan | 32 |

Example 19: Nanotization of Antifungal and Antibacterial Agents

Some of the antifungal and antibacterial agents for topical use were subjected to nanotization. The nanoparticles were formed using two approaches: nanoprecipitation using single polymer, and using combination of polymers. Polymeric nanoparticle formation using nanoprecipitaion and further processing of the resulting dispersions was exemplified using zinc pyrithione as antifungal agent.

Preparation of Polymeric Nanoparticles of ZPTO

Zinc pyrithione, along with combination of different polymers and fatty acid(s)/lipid(s), was used to prepare several nanoparticle dispersions, some of which were subjected to further processing to finally get free flowing powder with stable nanoparticles and appreciable drug content.

Nanoprecipitates of ZPTO with Poly(Vinyl Alcohol) (PVA):

A solution of zinc pyrithione, DMSO and THF was added dropwise to 1% aq. solution of PVA (80% Hydrolyzed) while stirring at about 1200 rpm. The dispersion was continued to stir for 24 hrs in order to get rid of THF, and then centrifuged at 1000 rpm for 10 minutes to remove bigger particles if any. Then preparation was subjected to Dynamic Light Scattering (DLS) analysis [$Z_{avg}$: 337 nm, PDI: 0.165] using Malvern ZetaSizer ZS90.

Nanoprecipitates of ZPTO with Tripalmitin (Glyceryl Tripalmitate) and PVA:

A solution of zinc pyrithione, tripalmitin, DMSO and THF was added dropwise to 1% aq. solution of PVA (80% Hydrolyzed) while stirring at about 1200 rpm. The dispersion was continued to stir for 24 hrs in order to get rid of THF, and then centrifuged at 1000 rpm for 10 minutes to remove bigger particles if any. Then preparation was subjected to DLS analysis [$Z_{avg}$: 526 nm, PDI: 0.221].

Nanoprecipitates of ZPTO with Capmul MCM C8 EP (Glyceryl Monocaprylate) and PVA:

A solution of zinc pyrithione, capmul MCM C8 EP (from Abitec), DMSO and THF was added dropwise to 1% aq. solution of PVA (80% Hydrolyzed) while stirring at about 1200 rpm. The dispersion was continued to stir for 24 hrs and then centrifuged at 1000 rpm for 10 minutes to remove bigger particles if any. The supernatant was concentrated by centrifugal filter units (50 KD; from Millipore). The concentrated dispersion was then subjected to DLS analysis [$Z_{avg}$: 731 nm, PDI: 0.349], drug loading efficiency (90%), bioactivity in comparison to non-nanoformulated ZPTO. The concentrated dispersion was finally lyophilized with sucrose as cryoprotectant (5%) and the drug content (7%) was also determined.

Nanoprecipitates of ZPTO with PLGA, Capmul MCM C8 EP and PVA:

A solution of zinc pyrithione, PLGA, capmul MCM C8 EP (from Abitec) and DMSO was added dropwise to 1% aq. solution of PVA (80% Hydrolyzed) while stirring at about 1200 rpm. The dispersion was continued to stir for 24 hrs and then centrifuged at 1000 rpm for 10 minutes to remove bigger particles if any. Then preparation was subjected to DLS analysis [$Z_{avg}$: 330 nm, PDI: 0.176].

Nanoprecipitates of ZPTO with PLGA, Capmul MCM C8 EP and SLES (Sodium Laureth Sulphate):

A solution of zinc pyrithione, PLGA, capmul MCM C8 EP and DMSO was added dropwise to 0.1% aq. solution of SLES while stirring at about 1200 rpm. The dispersion was continued to stir for further 48 hrs and then centrifuged at 1000 rpm for 10 minutes to remove bigger particles if any. The supernatant was concentrated by centrifugal filter units (50 KD; from Millipore). The concentrated dispersion was then subjected to DLS analysis [$Z_{avg}$: 140 nm, PDI: 0.231], drug loading efficiency (48%), bioactivity in comparison to non-nanoformulated ZPTO. The concentrated dispersion was finally lyophilized with mannitol as cryoprotectant (2-5%) and the drug content (8%) was also determined.

Table 12 summarizes the data for some of the exemplary nano-preparations of zinc pyrithione.

TABLE 12

Average size distribution ($Z_{avg}$), polydispersity index (PDI) and major composition of some of the nano-preparations for zinc pyrithione.

| Preparation Code | $Z_{avg}$ (nm) | PDI | Prep-Components |
|---|---|---|---|
| VZP-NP-028 | 337 | 0.165 | (ZPTO:DMSO:THF) + 1% PVA |
| VZP-NP-054 | 526 | 0.221 | (ZPTO:DMSO:THF:Tripalm) + 1% PVA |
| VZP-NP-063 | 569 | 0.177 | (ZPTO:DMSO:THF Ceteth-10) + 1% PVA |
| VZP-NP-068 | 362 | 0.213 | (ZPTO:DMSO:THF:Capmul MCM C10) + 1% PVA |
| VZP-NP-070 | 476 | 0.264 | (ZPTO:DMSO:THF:Capmul MCM C8 EP + Precirol ATO 5) + 1% PVA |
| VZP-NP-072 | 480 | 0.241 | (ZPTO:DMSO:THF:Captex 355 EP/NP) + 1% PVA |
| VZP-NP-083 | 676 | 0.251 | (ZPTO:DMSO:THF:Tripalm) + 1% Poloxamer 188 |
| VZP-NP-092 | 445 | 0.273 | (ZPTO:DMSO:THF:Captex 355 EP/NP + Stearic acid) + 1% Poloxamer 188 |
| VZP-NP-100 | 434 | 0.211 | (ZPTO:DMSO:THF:Egg Lecithin in THF) + 1% PVA |
| VZP-NP-108 | 462 | 0.181 | (ZPTO:DMSO:THF:Soya Lecithin in THF) + 1% PVA |
| VZP-NP-112 | 492 | 0.249 | (ZPTO:DMSO:THF:Capmul MCM C8 EP) + 1% PVA |
| VZP-NP-115 | 788 | 0.298 | (ZPTO:DMSO:THF:Capmul MCM C8 EP + Stearic acid) + 1% PVA |
| VZP-NP-120 | 463 | 0.348 | (ZPTO:DMSO:THF:Capmul MCM C8 EP + Capmul MCM C10) + 1% PVA |
| VZP-NP-148 | 65.3 | 0.282 | (ZPTO:DMSO:PLGA:Capmul MCM C8 EP) + 1% PVA |

We claim:

1. A conjugate-based antifungal prodrug of formula: [(AFA)$_{m'}$-X]$_p$-L, wherein AFA is an antifungal agent; L is a fatty acid comprising a $C_{11}$-$C_{28}$ alkyl; X is a linker; m' is 1 to 10; and p is 1, 3, 4, or 5; wherein the linker is selected from group consisting of —CH(R$^1$)—, wherein R$^1$ is H or $C_1$-$C_6$ alkyl; and wherein the antifungal agent is selected from the group consisting of Fluconazole, Isavuconazole, Itraconazole, Ketoconazole, Miconazole, Clortrimazole, Voriconazole, Posaconazole, Ravuconazole, natamycin, lucensomycin, nystatin, amphotericin B, echinocandins, Cancidas, pradimicins, beanomicins, nikkomycins, sordarins, allylamines, Triclosan, Piroctone, phenpropimorph, terbinafine, antifungal peptide, and derivatives and analogs thereof.

2. The conjugate-based prodrug of claim 1, wherein m' and p are independently 1.

3. The conjugate-based prodrug of claim 1, wherein the conjugate-based prodrug is formulated as a nanoparticle.

4. The conjugate-based prodrug of claim 1, wherein the prodrug is formulated as a liposome, polymeric nanoparticle, nanoemulsion, self-microemulsifying drug delivery system (SMEDD), solid-lipid nanoparticle, nano-structured liquid crystal, or any combination thereof.

5. The conjugate-based prodrug of claim 1, wherein the linker is a cleavable linker.

6. The conjugate-based prodrug of claim 5, wherein the linker is cleaved by an esterase.

7. The conjugate-based prodrug of claim 1, wherein the antifungal agent comprises an azole moiety or a hydroxyl group.

8. The conjugate-based prodrug of claim 1, wherein the antifungal agent is selected from the group consisting of Fluconazole, Isavuconazole, Itraconazole, Ketoconazole, Miconazole, Clortrimazole, Voriconazole, Posaconazole, Ravuconazole, and derivatives and analogs thereof.

9. The conjugate-based prodrug of claim 1, wherein the carrier is a fatty acid selected from the group consisting of Undecylic acid, Lauric acid, Tridecylic acid, Myristic acid, Pentadecylic acid, Palmitic acid, Heptadecanoic acid, Stearic acid, Nonadecylic acid, Arachidic acid, Heneicosylic acid, Behenic acid, Tricosylic acid, Lignoceric acid, Pentacosylic acid, Cerotic acid, Heptacosylic acid, Montanic acid, Myristoleic acid, Palmitoleic acid, Sapienic acid, Oleic acid, Elaidic acid, Vaccenic acid, Linoleic acid, Linoelaidic acid, α-Linolenic acid, γ-Linolenic acid, Arachidonic acid, Eicosapentaenoic acid, Erucic acid, Docosahexaenoic acid, cis-11-octadecenoic acid, cis-11-eicosenoic acid, undecylenic acid, isostearic acid, and any combinations thereof.

10. The conjugate-based prodrug of claim 1, wherein the conjugate is ketoconazole methylene palmitate, ketoconazole 1-ethylene palmitate, ketoconazole methylene laurate, ketoconazole 1-ethylene laurate, ketoconazole methylene undecylenate, ketoconazole 1-ethylene undecylenate, ketoconazole methylene oleate, ketoconazole 1-ethylene oleate, ketoconazole methylene linolate, or ketoconazole 1-ethylene linolate.

11. A personal care composition comprising an effective amount of a conjugate-based prodrug of claim 1.

12. The personal care composition of claim 11, wherein the composition further comprises a pharmaceutical or a topical agent.

13. A method of inhibiting a fungal or bacterial infection in a subject, the method comprising administering to the subject in need thereof a composition of claim 11.

14. The conjugate-based prodrug of claim 1, wherein the conjugate is [(AFA)$_{m'}$-X]$_p$-L, wherein:
m' and p are 1;
X is —CH(R$^1$)—, where R$^1$ is H or $C_1$ alkyl;
L is a fatty acid comprising a $C_{11}$-$C_{28}$ alkyl; and
AFA is an antifungal agent comprising an azole moiety.

15. The conjugate-based prodrug of claim 14, wherein the linker is —CH$_2$—; the antifungal agent is ketoconazole, clotrimazole, luliconazole or efinaconazole; and the carrier is a fatty acid selected from the group consisting of undecylic acid, lauric acid, tridecylic acid, myristic acid, pentadecylic acid, palmitic acid, heptadecanoic acid, stearic acid, myristoleic acid, palmitoleic acid, sapienic acid, oleic acid, elaidic acid, vaccenic acid, linoleic acid, linoelaidic acid, α-linolenic acid and γ-linolenic acid.

16. A conjugate-based prodrug of formula: $[(AFA)_{m'}\text{-}X]_p L$, wherein AFA ketoconazole; X is -CH$_2$-; m' is 1 to 10; and p is 1, 3, 4, or 5; and L is palmitic acid or oleic acid.

* * * * *